US010604583B2

(12) United States Patent
Orentas et al.

(10) Patent No.: US 10,604,583 B2
(45) Date of Patent: *Mar. 31, 2020

(54) ANTI-CD276 POLYPEPTIDES, PROTEINS, AND CHIMERIC ANTIGEN RECEPTORS

(71) Applicants: THE UNITED STATES OF AMERICA, AS PRESENTED BY THE SECRETARY, DEPARTMENT OF HEALTH AND HUMAN SERVICES, Bethesda, MD (US); BIOMED VALLEY DISCOVERIES, INC., Kansas City, MO (US)

(72) Inventors: Rimas J. Orentas, Chevy Chase, MD (US); Zhongyu Zhu, Frederick, MD (US); Crystal L. Mackall, Bethesda, MD (US); Dimiter S. Dimitrov, Frederick, MD (US); Bradley St. Croix, Frederick, MD (US); Saurabh Saha, Leawood, KS (US)

(73) Assignees: The United States of America, as represented by the Secretary, Department of Health and Human Services, Bethesda, MD (US); Biomed Valley Discoveries, Inc., Kansas City, MO (US)

( * ) Notice: Subject to any disclaimer, the term of this patent is extended or adjusted under 35 U.S.C. 154(b) by 94 days.

This patent is subject to a terminal disclaimer.

(21) Appl. No.: 15/699,419

(22) Filed: Sep. 8, 2017

(65) Prior Publication Data
US 2017/0369585 A1 Dec. 28, 2017

Related U.S. Application Data

(63) Continuation of application No. 14/779,586, filed as application No. PCT/US2014/031543 on Mar. 24, 2014, now Pat. No. 9,790,282.

(60) Provisional application No. 61/805,001, filed on Mar. 25, 2013.

(51) Int. Cl.
*C07K 16/30* (2006.01)
*C07K 16/28* (2006.01)
*G01N 33/574* (2006.01)

(52) U.S. Cl.
CPC .......... *C07K 16/30* (2013.01); *C07K 16/2827* (2013.01); *G01N 33/57492* (2013.01); *C07K 2317/21* (2013.01); *C07K 2317/33* (2013.01); *C07K 2317/622* (2013.01); *C07K 2317/73* (2013.01); *C07K 2317/92* (2013.01); *C07K 2319/00* (2013.01)

(58) Field of Classification Search
None
See application file for complete search history.

(56) References Cited

U.S. PATENT DOCUMENTS

| | | |
|---|---|---|
| 3,832,253 A | 8/1974 | DiPalma et al. |
| 3,854,480 A | 12/1974 | Zaffaroni |
| 4,235,871 A | 11/1980 | Papahadjopoulos et al. |
| 4,450,150 A | 5/1984 | Sidman |
| 4,452,775 A | 6/1984 | Kent |
| 4,501,728 A | 2/1985 | Geho et al. |
| 4,667,014 A | 5/1987 | Nestor, Jr. et al. |
| 4,748,034 A | 5/1988 | de Rahm |
| 4,837,028 A | 6/1989 | Allen |
| 4,892,827 A | 1/1990 | Pastan et al. |
| 5,019,369 A | 5/1991 | Presant et al. |
| 5,075,109 A | 12/1991 | Tice et al. |
| 5,225,539 A | 7/1993 | Winter |
| 5,239,660 A | 8/1993 | Ooi |
| 5,449,752 A | 9/1995 | Fujii et al. |
| 5,512,658 A | 4/1996 | Pastan et al. |
| 5,545,806 A | 8/1996 | Lonberg et al. |
| 5,569,825 A | 10/1996 | Lonberg et al. |
| 5,585,089 A | 12/1996 | Queen et al. |
| 5,602,095 A | 2/1997 | Pastan et al. |
| 5,608,039 A | 3/1997 | Pastan et al. |
| 5,639,641 A | 6/1997 | Pedersen et al. |
| 5,693,761 A | 12/1997 | Queen et al. |
| 5,714,352 A | 2/1998 | Jakobovits |
| 5,821,238 A | 10/1998 | Pastan et al. |
| 5,854,044 A | 12/1998 | Pastan et al. |

(Continued)

FOREIGN PATENT DOCUMENTS

| | | | |
|---|---|---|---|
| EP | 0239400 A2 | 9/1987 | |
| EP | 2703486 A1 | 5/2014 | |
| GB | 2188638 A | 10/1987 | |
| WO | 2008116219 A2 | 9/2008 | |
| WO | 2011109400 A2 | 9/2011 | |
| WO | 2012079000 A1 | 6/2012 | |
| WO | 2012147713 A1 | 11/2012 | |
| WO | 2013059593 A1 | 4/2013 | |
| WO | 2014011518 A1 | 1/2014 | |
| WO | WO-2014160627 A1 * | 10/2014 | ......... C07K 16/2827 |

OTHER PUBLICATIONS

Choi, N. W., et al. Synthesis and assembly of a cholera toxin B subunit-rotavirus VP7 fusion protein in transgenic potato, Mal. Biotechnol. 31: 193-202 (2005).

(Continued)

*Primary Examiner* — Peter J Reddig
(74) *Attorney, Agent, or Firm* — Bryan Cave Leighton Paisner LLP

(57) ABSTRACT

Polypeptides and proteins that specifically bind to and immunologically recognize CD276 are disclosed. Chimeric antigen receptors (CARs), anti-CD276 binding moieties, nucleic acids, recombinant expression vectors, host cells, populations of cells, and pharmaceutical compositions relating to the polypeptides and proteins are also disclosed. Methods of detecting the presence of cancer in a mammal and methods of treating or preventing cancer in a mammal are also disclosed.

22 Claims, 8 Drawing Sheets

Specification includes a Sequence Listing.

(56) References Cited

U.S. PATENT DOCUMENTS

| | | |
|---|---|---|
| 6,265,150 B1 | 7/2001 | Terstappen et al. |
| 9,790,282 B2 * | 10/2017 | Orentas .............. C07K 16/2827 |
| 2002/0197266 A1 | 12/2002 | Debinski |
| 2003/0198638 A1 | 10/2003 | Watkins |
| 2010/0215656 A1 | 8/2010 | Pastan et al. |
| 2012/0294796 A1 | 11/2012 | Johnson et al. |

OTHER PUBLICATIONS

Kohler, G., et al., Derivation of specific antibody-producing tissue culture and tumor lines by cell fusion, Eur. J. Immunol. Jul. 1976;6(7):511-9.

Greenfield, E. A. (ed.), Antibodies: A Laboratory Manual, Second Edition: Generating Monoclonal Antibodies Successful Plating Strategies, CSH Press (2013).

Murphy, K., et al., (ed) Janeway's Immunobiology, 8th Ed., Taylor & Francis, Ind, NY, NY (2011).

Haskard, D.O., et al., The production of human monoclonal autoantibodies from patients with rheumatoid arthritis by the EBV-hybridoma technique, Journal of Immunology Methods, vol. 74, Issue 2, 361-637 (1984).

Green, M. R., et al., Molecular Cloning: A Laboratory Manual, 4th Ed., vol. 1, CSH Lab Press, New York (2012).

Ausubel, F. M., et al., Current Protocols in Molecular Biology, Green Publishing Associates and John Wiley & Sons, NY (2007).

Pedersen, J. T., et al., Comparison of Surface Accessible Residues in Human and Murine Immunoglobulin Fv Domains: Implication for Humanization of Murine Antibodies, Journal of Molecular Biology, vol. 235, Issue 3, 959-973 (1994).

Chan, W. C. et al., Fmoc Solid phase peptide synthesis, A Practical Approach, Oxford Univ. Press, Oxford, UK 2001.

Reid, R. E., et al., Peptide and Protein Drug Analysis, ed., New York : M. Dekker, 2000.

Westwood, O.M.R., et al., An Introduction to Epitope Mapping, ed., Oxford Univ. Press UK 2000.

Hudecz, F., Peptide Synthesis and Applications, Methods in Mol. Bio., 298: 209-223 (2005).

Kirin, S. I., et al., Amino Acid and Peptide Bioconjugates of Copper(II) and Zinc(II) Complexes with a Modified N,N-Bis(2-picolyl)amine Ligand, Inorg. Chem., 2005, 44 (15), pp. 5405-5415.

Graham, F. L., et al., A technique for the assay of infectivity of human adenovirus 5 DNA, Virology, 52: 456-467 (1973).

Davis, L.G. et al., Basic Methods in Molecular Biology, Elsevier (1986).

Chu, G., et al., SV40 DNA transfection of cells in suspension: analysis of the efficiency of transcription and translation of T-antigen, Gene, 13 (1981) 197-202.

Capecchi, M. R., High efficiency transformation by direct microinjection of DNA into cultured mammalian cells. Cell, 22:479-488 (1980).

Shigekawa, Electroporation of eukaryotes and prokaryotes: A general approach to the introduction of macromolecules into cells. BioTechniques, 6 (8):742-751 (1988).

Mannino, RJ, et al., Liposome mediated gene transfer, BioTechniques, Jul. 1, 1988, 6(7):682-690.

Felgner, P.L., et al., Lipofection: a highly efficient, lipid-mediated DNA-transfection procedure, Proc. Natl. Acad. Sci. USA, vol. 84, No. 21, pp. 7413-7417 (Nov. 1, 1987).

Klein, T.M. et al., High-velocity microprojectiles for delivering nucleic acids into living cells, Nature 327, 70-73, (1987).

Springer, C.J., et al., Suicide Gene Therapy: Methods and Reviews, (Cancer Research UK Centre for Cancer Therapeutics at the Institute of Cancer Research, Humana Press 2004.

Remington, The Science and practice of pharmacy, 21 Ed., Lippincott Williams and Wilkins, Philadelphia, PA, 2005.

Thompson, J.E. et al., A Practical Guide to Contemporary Pharmacy Practice, Lippincott Williams & Wilkins, Phil., PA, 2009.

Trissel, L. A., Handbook on Injectable Drugs, 16th Ed., 2010.

Szoka, F., Jr., et al., Comparative Properties and Methods of Preparation of Lipid Vesicles (Liposomes), Annu. Rev. Biophys. Bioeng. 1980, 9:467-508.

Clay, T.M., et al., Efficient Transfer of a Tumor Antigen-Reactive TCR to Human Peripheral Blood Lymphocytes Confers Anti-Tumor Reactivity, Journal of Immunology, J Immunol 1999; 163:507-513.

Zhao, Y., et al., Primary human lymphocytes transduced with NY-ESO-1 antigen-specific TCR genes recognize and kill diverse human tumor cell lines, Journal of Immunology, vol. 174, Issue 7, Apr. 1, 2005, pp. 4415-4423.

Roder, JC., et al., The EBV-hybridoma technique, Methods Enzymol. 1986;121:140-67.

Reiter, Y., et al., Engineering interchain disulfide bonds into conserved framework regions of Fv fragments: improved biochemical characteristics of recombinant immunotoxins containing disulfide-stabilized Fv, Protein Engineering, vol. 7, Issue 5, pp. 697-704, May 1994.

International Search Report for PCT/US2014/031543, dated Jul. 21, 2014.

Written Opinion of the International Searching Authority for PCT/US2014/031543, dated Jul. 21, 2014.

Jemal, A.,et al. Cancer statistics, 2007. CA Cancer J Clin. Jan.-Feb. 2007;57(1):43-66.

Loo, D., et al. Development of an Fc-enhanced anti-B7-H3 monoclonal antibody with potent antitumor activity. Clin Cancer Res. Jul. 15, 2012;18(14):3834-45.

Orentas, R.J., et al. Identification of cell surface proteins as potential immunotherapy targets in 12 pediatric cancers. Front Oncol. Dec. 17, 2012;2:194.

Rudikoff, S., et al. Single amino acid substitution altering antigen-binding specificity. Proc Natl Acad Sci U S A. Mar. 1982; 79(6): 1979-1983.

Colman, P.M., Effects of amino acid sequence changes on antibody-antigen interactions. Res Immunol. Jan. 1994;145(1):33-36.

Abaza, M.S., et al. Effects of amino acid substitutions outside an antigenic site on protein binding to monoclonal antibodies of predetermined specificity obtained by peptide immunization: demonstration with region 94-100 (antigenic site 3) of myoglobin. J Protein Chem. Oct. 1992;11(5):433-444.

Gussow, D. and Seemann, G., Humanization of monoclonal antibodies. Methods in Enzymology (1991) 203:99-121.

Ibragimova, G.T. and Wade, R.C., Stability of the beta-sheet of the WW domain: A molecular dynamics simulation study. Biophys J. Oct. 1999;77(4):2191-8.

Gura, T., Systems for identifying new drugs are often faulty. Science. Nov. 7, 1997;278(5340):1041-2.

Chames, P., et al. Therapeutic antibodies: successes, limitations and hopes for the future. Br J Pharmacol. May 2009;157(2):220-33.

Byers, T., What can randomized controlled trials tell us about nutrition and cancer prevention? CA Cancer J Clin. Nov.-Dec. 1999;49(6):353-61.

Violette, P.D. and Saad, F., Chemoprevention of prostate cancer: myths and realities. J Am Board Fam Med. Jan.-Feb. 2012;25(1):111-9.

\* cited by examiner

SEQUENCE LISTING

```
<160> NUMBER OF SEQ ID NOS: 140

<210> SEQ ID NO 1
<211> LENGTH: 8
<212> TYPE: PRT
<213> ORGANISM: Artificial Sequence
<220> FEATURE:
<223> OTHER INFORMATION: Synthetic

<400> SEQUENCE: 1

Gly Gly Thr Phe Ser Ser Tyr Ala
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic

<400> SEQUENCE: 2

Ile Ile Pro Ile Leu Gly Ile Ala
1               5

<210> SEQ ID NO 3
<211> LENGTH: 12
<212> TYPE: PRT
<213> ORGANISM: Artificial Sequence
<220> FEATURE:
<223> OTHER INFORMATION: Synthetic

<400> SEQUENCE: 3

Ala Thr Gly Gly Ser Gly Arg Tyr Ala Leu Asp Ile
1               5                   10

<210> SEQ ID NO 4
<211> LENGTH: 6
<212> TYPE: PRT
<213> ORGANISM: Artificial Sequence
<220> FEATURE:
<223> OTHER INFORMATION: Synthetic

<400> SEQUENCE: 4

Gln Ser Val Ser Ser Tyr
1               5

<210> SEQ ID NO 5
<211> LENGTH: 3
<212> TYPE: PRT
<213> ORGANISM: Artificial Sequence
<220> FEATURE:
<223> OTHER INFORMATION: Synthetic

<400> SEQUENCE: 5

Asp Ala Ser
1
```

<210> SEQ ID NO 6
<211> LENGTH: 11
<212> TYPE: PRT
<213> ORGANISM: Artificial Sequence
<220> FEATURE:
<223> OTHER INFORMATION: Synthetic

<400> SEQUENCE: 6

```
Gln Gln Arg Ser Asn Trp Pro Pro Ser Tyr Thr
1               5                   10
```

<210> SEQ ID NO 7
<211> LENGTH: 119
<212> TYPE: PRT
<213> ORGANISM: Artificial Sequence
<220> FEATURE:
<223> OTHER INFORMATION: Synthetic

<400> SEQUENCE: 7

```
Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Gly Ser Gly Arg Tyr Ala Leu Asp Ile Trp Gly Gln Gly
            100                 105                 110

Thr Met Val Thr Val Ser Ser
        115
```

<210> SEQ ID NO 8
<211> LENGTH: 109
<212> TYPE: PRT
<213> ORGANISM: Artificial Sequence
<220> FEATURE:
<223> OTHER INFORMATION: Synthetic

<400> SEQUENCE: 8

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ser Tyr Thr Phe Gly Gln Gly Thr Lys Leu Glu Ile Lys
            100                 105
```

```
<210> SEQ ID NO 9
<211> LENGTH: 17
<212> TYPE: PRT
<213> ORGANISM: Artificial Sequence
<220> FEATURE:
<223> OTHER INFORMATION: Synthetic

<400> SEQUENCE: 9

Ser Ser Gly Gly Gly Ser Gly Gly Gly Ser Gly Gly Gly
1               5                   10                  15

Ser

<210> SEQ ID NO 10
<211> LENGTH: 244
<212> TYPE: PRT
<213> ORGANISM: Artificial Sequence
<220> FEATURE:
<223> OTHER INFORMATION: Synthetic

<400> SEQUENCE: 10

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Gly Ser Gly Arg Tyr Ala Leu Asp Ile Trp Gly Gln Gly
            100                 105                 110

Thr Met Val Thr Val Ser Ser Gly Gly Gly Ser Gly Gly Gly
        115                 120                 125

Ser Gly Gly Gly Ser Glu Ile Val Leu Thr Gln Ser Pro Ala Thr
    130                 135                 140

Leu Ser Leu Ser Pro Gly Glu Arg Ala Thr Leu Ser Cys Arg Ala Ser
145                 150                 155                 160

Gln Ser Val Ser Ser Tyr Leu Ala Trp Tyr Gln Gln Lys Pro Gly Gln
                165                 170                 175

Ala Pro Arg Leu Leu Ile Tyr Asp Ala Ser Asn Arg Ala Thr Gly Ile
            180                 185                 190

Pro Ala Arg Phe Ser Gly Ser Gly Ser Gly Thr Asp Phe Thr Leu Thr
        195                 200                 205

Ile Ser Ser Leu Glu Pro Glu Asp Phe Ala Val Tyr Tyr Cys Gln Gln
    210                 215                 220

Arg Ser Asn Trp Pro Pro Ser Tyr Thr Phe Gly Gln Gly Thr Lys Leu
225                 230                 235                 240

Glu Ile Lys Arg

<210> SEQ ID NO 11
<211> LENGTH: 8
<212> TYPE: PRT
<213> ORGANISM: Artificial Sequence
<220> FEATURE:
<223> OTHER INFORMATION: Synthetic
```

```
<400> SEQUENCE: 11

Gly Gly Thr Phe Ser Ser Tyr Ala
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic

<400> SEQUENCE: 12

Ile Ile Pro Ile Leu Gly Ile Ala
1               5

<210> SEQ ID NO 13
<211> LENGTH: 15
<212> TYPE: PRT
<213> ORGANISM: Artificial Sequence
<220> FEATURE:
<223> OTHER INFORMATION: Synthetic

<400> SEQUENCE: 13

Ala Arg Gly Gly Ala Gly Gly Ser Gly Ser Tyr Tyr Pro Leu Ile
1               5                   10                  15

<210> SEQ ID NO 14
<211> LENGTH: 7
<212> TYPE: PRT
<213> ORGANISM: Artificial Sequence
<220> FEATURE:
<223> OTHER INFORMATION: Synthetic

<400> SEQUENCE: 14

Gln Ser Val Ser Ser Ser Tyr
1               5

<210> SEQ ID NO 15
<211> LENGTH: 3
<212> TYPE: PRT
<213> ORGANISM: Artificial Sequence
<220> FEATURE:
<223> OTHER INFORMATION: Synthetic

<400> SEQUENCE: 15

Asp Ala Ser
1

<210> SEQ ID NO 16
<211> LENGTH: 11
<212> TYPE: PRT
<213> ORGANISM: Artificial Sequence
<220> FEATURE:
<223> OTHER INFORMATION: Synthetic

<400> SEQUENCE: 16

Gln Gln Arg Ser Ser Trp Pro Pro Thr Trp Thr
1               5                   10

<210> SEQ ID NO 17
<211> LENGTH: 122
<212> TYPE: PRT
<213> ORGANISM: Artificial Sequence
<220> FEATURE:
<223> OTHER INFORMATION: Synthetic

<400> SEQUENCE: 17
```

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Gly Gly Ala Gly Gly Ser Gly Ser Tyr Tyr Pro Leu Ile Trp
        100                 105                 110

Gly Gln Gly Thr Thr Val Thr Val Ser Ser
            115                 120

<210> SEQ ID NO 18
<211> LENGTH: 110
<212> TYPE: PRT
<213> ORGANISM: Artificial Sequence
<220> FEATURE:
<223> OTHER INFORMATION: Synthetic

<400> SEQUENCE: 18

Glu Ile Val Leu Thr Gln Ser Pro Ala Thr Leu Ser Leu Ser Pro Gly
1               5                   10                  15

Glu Arg Ala Thr Leu Ser Cys Gly Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Arg Ser Ser Trp Pro
            85                  90                  95

Pro Thr Trp Thr Phe Gly Gln Gly Thr Lys Leu Glu Ile Lys
        100                 105                 110

<210> SEQ ID NO 19
<211> LENGTH: 248
<212> TYPE: PRT
<213> ORGANISM: Artificial Sequence
<220> FEATURE:
<223> OTHER INFORMATION: Synthetic

<400> SEQUENCE: 19

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
50                  55                  60

Gln Gly Arg Val Thr Ile Thr Ala Asp Glu Ser Thr Ser Thr Ala Tyr

```
                65                  70                  75                  80
Met Glu Leu Ser Ser Leu Arg Ser Glu Asp Thr Ala Val Tyr Tyr Cys
                    85                  90                  95

Ala Arg Gly Gly Ala Gly Gly Ser Gly Ser Tyr Tyr Pro Leu Ile Trp
                100                 105                 110

Gly Gln Gly Thr Thr Val Thr Val Ser Ser Gly Gly Gly Gly Ser Gly
                115                 120                 125

Gly Gly Gly Ser Gly Gly Gly Ser Glu Ile Val Leu Thr Gln Ser
130                 135                 140

Pro Ala Thr Leu Ser Leu Ser Pro Gly Glu Arg Ala Thr Leu Ser Cys
145                 150                 155                 160

Gly Ala Ser Gln Ser Val Ser Ser Ser Tyr Leu Ala Trp Tyr Gln Gln
                165                 170                 175

Lys Pro Gly Gln Ala Pro Arg Leu Leu Ile Tyr Asp Ala Ser Ser Arg
                180                 185                 190

Ala Thr Gly Ile Pro Ala Arg Phe Ser Gly Ser Gly Ser Gly Thr Asp
                195                 200                 205

Phe Thr Leu Thr Ile Ser Ser Leu Glu Pro Glu Asp Phe Ala Val Tyr
                210                 215                 220

Tyr Cys Gln Gln Arg Ser Ser Trp Pro Pro Thr Trp Thr Phe Gly Gln
225                 230                 235                 240

Gly Thr Lys Leu Glu Ile Lys Arg
                245
```

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

```
Gly Gly Thr Phe Ser Ser Tyr Ala
1               5
```

<210> SEQ ID NO 21
<211> LENGTH: 8
<212> TYPE: PRT
<213> ORGANISM: Artificial Sequence
<220> FEATURE:
<223> OTHER INFORMATION: Synthetic

<400> SEQUENCE: 21

```
Ile Ile Pro Ile Leu Gly Thr Ala
1               5
```

<210> SEQ ID NO 22
<211> LENGTH: 10
<212> TYPE: PRT
<213> ORGANISM: Artificial Sequence
<220> FEATURE:
<223> OTHER INFORMATION: Synthetic

<400> SEQUENCE: 22

```
Ala Arg Trp Gly Gly Gly Ala Phe Asp Ile
1               5                   10
```

<210> SEQ ID NO 23
<211> LENGTH: 6
<212> TYPE: PRT
<213> ORGANISM: Artificial Sequence

```
<220> FEATURE:
<223> OTHER INFORMATION: Synthetic

<400> SEQUENCE: 23

Gln Ser Val Gly Gly Tyr
1               5

<210> SEQ ID NO 24
<211> LENGTH: 3
<212> TYPE: PRT
<213> ORGANISM: Artificial Sequence
<220> FEATURE:
<223> OTHER INFORMATION: Synthetic

<400> SEQUENCE: 24

Asp Ala Ser
1

<210> SEQ ID NO 25
<211> LENGTH: 11
<212> TYPE: PRT
<213> ORGANISM: Artificial Sequence
<220> FEATURE:
<223> OTHER INFORMATION: Synthetic

<400> SEQUENCE: 25

Gln Gln Arg Asn Asn Trp Pro Pro Met Tyr Thr
1               5                   10

<210> SEQ ID NO 26
<211> LENGTH: 117
<212> TYPE: PRT
<213> ORGANISM: Artificial Sequence
<220> FEATURE:
<223> OTHER INFORMATION: Synthetic

<400> SEQUENCE: 26

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Gly Gly Ala Phe Asp Ile Trp Gly Gln Gly Thr Met
            100                 105                 110

Val Thr Val Ser Ser
        115

<210> SEQ ID NO 27
<211> LENGTH: 109
<212> TYPE: PRT
<213> ORGANISM: Artificial Sequence
<220> FEATURE:
<223> OTHER INFORMATION: Synthetic

<400> SEQUENCE: 27

Glu Ile Val Leu Thr Gln Ser Pro Gly Thr Leu Ser Leu Ser Pro Gly
```

```
                 1               5                  10                 15
        Glu Arg Ala Thr Leu Ser Cys Arg Ala Ser Gln Ser Val Gly Gly Tyr
                        20                  25                 30

Leu Ala Trp Tyr Gln Gln Lys Pro Gly Gln Ala Pro Arg Leu Leu Ile
                        35                  40                 45

Tyr Asp Ala Ser Asn Arg Ala Thr Gly Ile Pro Ala Arg Phe Ser Gly
                        50                  55                 60

Ser Gly Ser Gly Thr Asp Phe Thr Leu Thr Ile Ser Ser Leu Glu Pro
        65                      70                  75                 80

Glu Asp Phe Ala Val Tyr Tyr Cys Gln Gln Arg Asn Asn Trp Pro Pro
                        85                  90                 95

Met Tyr Thr Phe Gly Gln Gly Thr Lys Leu Glu Ile Lys
                        100                 105

<210> SEQ ID NO 28
<211> LENGTH: 242
<212> TYPE: PRT
<213> ORGANISM: Artificial Sequence
<220> FEATURE:
<223> OTHER INFORMATION: Synthetic

<400> SEQUENCE: 28

Gln Val Gln Leu Val Gln Ser Gly Ala Glu Val Lys Lys Pro Gly Ser
        1               5                  10                 15

Ser Val Lys Val Ser Cys Lys Ala Ser Gly Gly Thr Phe Ser Ser Tyr
                        20                  25                 30

Ala Ile Ser Trp Val Arg Gln Ala Pro Gly Gln Gly Leu Glu Trp Met
                        35                  40                 45

Gly Gly Ile Ile Pro Ile Leu Gly Thr Ala Asn Tyr Ala Gln Lys Phe
                        50                  55                 60

Gln Gly Arg Val Thr Ile Thr Ala Asp Glu Ser Thr Ser Thr Ala Tyr
        65                      70                  75                 80

Met Glu Leu Ser Ser Leu Arg Ser Glu Asp Thr Ala Val Tyr Tyr Cys
                        85                  90                 95

Ala Arg Trp Gly Gly Gly Ala Phe Asp Ile Trp Gly Gln Gly Thr Met
                        100                 105                110

Val Thr Val Ser Ser Gly Gly Gly Ser Gly Gly Gly Gly Ser Gly
                        115                 120                 125

Gly Gly Gly Ser Glu Ile Val Leu Thr Gln Ser Pro Gly Thr Leu Ser
                        130                 135                140

Leu Ser Pro Gly Glu Arg Ala Thr Leu Ser Cys Arg Ala Ser Gln Ser
        145                     150                 155                160

Val Gly Gly Tyr Leu Ala Trp Tyr Gln Gln Lys Pro Gly Gln Ala Pro
                        165                 170                175

Arg Leu Leu Ile Tyr Asp Ala Ser Asn Arg Ala Thr Gly Ile Pro Ala
                        180                 185                190

Arg Phe Ser Gly Ser Gly Ser Gly Thr Asp Phe Thr Leu Thr Ile Ser
                        195                 200                 205

Ser Leu Glu Pro Glu Asp Phe Ala Val Tyr Tyr Cys Gln Gln Arg Asn
                        210                 215                 220

Asn Trp Pro Pro Met Tyr Thr Phe Gly Gln Gly Thr Lys Leu Glu Ile
        225                     230                 235                240

Lys Arg

<210> SEQ ID NO 29
```

<211> LENGTH: 84
<212> TYPE: PRT
<213> ORGANISM: Artificial Sequence
<220> FEATURE:
<223> OTHER INFORMATION: Synthetic

<400> SEQUENCE: 29

```
Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn Arg
```

<210> SEQ ID NO 30
<211> LENGTH: 67
<212> TYPE: PRT
<213> ORGANISM: Artificial Sequence
<220> FEATURE:
<223> OTHER INFORMATION: Synthetic

<400> SEQUENCE: 30

```
Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg
65
```

<210> SEQ ID NO 31
<211> LENGTH: 69
<212> TYPE: PRT
<213> ORGANISM: Artificial Sequence
<220> FEATURE:
<223> OTHER INFORMATION: Synthetic

<400> SEQUENCE: 31

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65
```

<210> SEQ ID NO 32
<211> LENGTH: 40
<212> TYPE: PRT

<213> ORGANISM: Artificial Sequence
<220> FEATURE:
<223> OTHER INFORMATION: Synthetic

<400> SEQUENCE: 32

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser
        35                  40

<210> SEQ ID NO 33
<211> LENGTH: 47
<212> TYPE: PRT
<213> ORGANISM: Artificial Sequence
<220> FEATURE:
<223> OTHER INFORMATION: Synthetic

<400> SEQUENCE: 33

Arg Phe Ser Val Val Lys Arg Gly Arg Lys Lys Leu Leu Tyr Ile Phe
1               5                   10                  15

Lys Gln Pro Phe Met Arg Pro Val Gln Thr Thr Gln Glu Glu Asp Gly
            20                  25                  30

Cys Ser Cys Arg Phe Pro Glu Glu Glu Glu Gly Gly Cys Glu Leu
        35                  40                  45

<210> SEQ ID NO 34
<211> LENGTH: 112
<212> TYPE: PRT
<213> ORGANISM: Artificial Sequence
<220> FEATURE:
<223> OTHER INFORMATION: Synthetic

<400> SEQUENCE: 34

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 35
<211> LENGTH: 40
<212> TYPE: PRT
<213> ORGANISM: Artificial Sequence
<220> FEATURE:
<223> OTHER INFORMATION: Synthetic

<400> SEQUENCE: 35

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro

```
                    20                  25                  30

Arg Asp Phe Ala Ala Tyr Arg Ser
            35                  40

<210> SEQ ID NO 36
<211> LENGTH: 112
<212> TYPE: PRT
<213> ORGANISM: Artificial Sequence
<220> FEATURE:
<223> OTHER INFORMATION: Synthetic

<400> SEQUENCE: 36

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 37
<211> LENGTH: 42
<212> TYPE: PRT
<213> ORGANISM: Artificial Sequence
<220> FEATURE:
<223> OTHER INFORMATION: Synthetic

<400> SEQUENCE: 37

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 38
<211> LENGTH: 112
<212> TYPE: PRT
<213> ORGANISM: Artificial Sequence
<220> FEATURE:
<223> OTHER INFORMATION: Synthetic

<400> SEQUENCE: 38

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80
```

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 39
<211> LENGTH: 703
<212> TYPE: PRT
<213> ORGANISM: Artificial Sequence
<220> FEATURE:
<223> OTHER INFORMATION: Synthetic

<400> SEQUENCE: 39

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Gly Ser Gly Arg Tyr Ala Leu Asp Ile Trp Gly Gln Gly
            100                 105                 110

Thr Met Val Thr Val Ser Ser Gly Gly Gly Gly Ser Gly Gly Gly Gly
            115                 120                 125

Ser Gly Gly Gly Gly Ser Glu Ile Val Leu Thr Gln Ser Pro Ala Thr
130                 135                 140

Leu Ser Leu Ser Pro Gly Glu Arg Ala Thr Leu Ser Cys Arg Ala Ser
145                 150                 155                 160

Gln Ser Val Ser Ser Tyr Leu Ala Trp Tyr Gln Gln Lys Pro Gly Gln
                165                 170                 175

Ala Pro Arg Leu Leu Ile Tyr Asp Ala Ser Asn Arg Ala Thr Gly Ile
            180                 185                 190

Pro Ala Arg Phe Ser Gly Ser Gly Ser Gly Thr Asp Phe Thr Leu Thr
        195                 200                 205

Ile Ser Ser Leu Glu Pro Glu Asp Phe Ala Val Tyr Tyr Cys Gln Gln
    210                 215                 220

Arg Ser Asn Trp Pro Pro Ser Tyr Thr Phe Gly Gln Gly Thr Lys Leu
225                 230                 235                 240

Glu Ile Lys Arg Ala Glu Pro Lys Ser Cys Asp Lys Thr His Thr Cys
                245                 250                 255

Pro Pro Cys Pro Ala Pro Glu Leu Leu Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

-continued

```
Thr Val Leu His Gln Asp Trp Leu Asn Gly Lys Glu Tyr Lys Cys Lys
            340                 345                 350
Val Ser Asn Lys Ala Leu Pro Ala Pro Ile Glu Lys Thr Ile Ser Lys
        355                 360                 365
Ala Lys Gly Gln Pro Arg Glu Pro Gln Val Tyr Thr Leu Pro Pro Ser
    370                 375                 380
Arg Asp Glu Leu Thr Lys Asn Gln Val Ser Leu Thr Cys Leu Val Lys
385                 390                 395                 400
Gly Phe Tyr Pro Ser Asp Ile Ala Val Glu Trp Glu Ser Asn Gly Gln
                405                 410                 415
Pro Glu Asn Asn Tyr Lys Thr Thr Pro Pro Val Leu Asp Ser Asp Gly
            420                 425                 430
Ser Phe Phe Leu Tyr Ser Lys Leu Thr Val Asp Lys Ser Arg Trp Gln
        435                 440                 445
Gln Gly Asn Val Phe Ser Cys Ser Val Met His Glu Ala Leu His Asn
    450                 455                 460
His Tyr Thr Gln Lys Ser Leu Ser Leu Ser Pro Gly Lys Lys Asp Pro
465                 470                 475                 480
Lys Ala Ala Ala Ile Glu Val Met Tyr Pro Pro Tyr Leu Asp Asn
                485                 490                 495
Glu Lys Ser Asn Gly Thr Ile Ile His Val Lys Gly Lys His Leu Cys
            500                 505                 510
Pro Ser Pro Leu Phe Pro Gly Pro Ser Lys Pro Phe Trp Val Leu Val
        515                 520                 525
Val Val Gly Gly Val Leu Ala Cys Tyr Ser Leu Leu Val Thr Val Ala
    530                 535                 540
Phe Ile Ile Phe Trp Val Arg Ser Lys Arg Ser Arg Leu Leu His Ser
545                 550                 555                 560
Asp Tyr Met Asn Met Thr Pro Arg Arg Pro Gly Pro Thr Arg Lys His
                565                 570                 575
Tyr Gln Pro Tyr Ala Pro Pro Arg Asp Phe Ala Ala Tyr Arg Ser Arg
            580                 585                 590
Val Lys Phe Ser Arg Ser Ala Asp Ala Pro Ala Tyr Gln Gln Gly Gln
        595                 600                 605
Asn Gln Leu Tyr Asn Glu Leu Asn Leu Gly Arg Arg Glu Glu Tyr Asp
    610                 615                 620
Val Leu Asp Lys Arg Arg Gly Arg Asp Pro Glu Met Gly Gly Lys Pro
625                 630                 635                 640
Arg Arg Lys Asn Pro Gln Glu Gly Leu Tyr Asn Glu Leu Gln Lys Asp
                645                 650                 655
Lys Met Ala Glu Ala Tyr Ser Glu Ile Gly Met Lys Gly Glu Arg Arg
            660                 665                 670
Arg Gly Lys Gly His Asp Gly Leu Tyr Gln Gly Leu Ser Thr Ala Thr
        675                 680                 685
Lys Asp Thr Tyr Asp Ala Leu His Met Gln Ala Leu Pro Pro Arg
    690                 695                 700

<210> SEQ ID NO 40
<211> LENGTH: 707
<212> TYPE: PRT
<213> ORGANISM: Artificial Sequence
<220> FEATURE:
<223> OTHER INFORMATION: Synthetic

<400> SEQUENCE: 40
```

```
Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Gly Ser Gly Arg Tyr Ala Leu Asp Ile Trp Gly Gln Gly
            100                 105                 110

Thr Met Val Thr Val Ser Ser Gly Gly Gly Gly Ser Gly Gly Gly Gly
        115                 120                 125

Ser Gly Gly Gly Gly Ser Glu Ile Val Leu Thr Gln Ser Pro Ala Thr
    130                 135                 140

Leu Ser Leu Ser Pro Gly Glu Arg Ala Thr Leu Ser Cys Arg Ala Ser
145                 150                 155                 160

Gln Ser Val Ser Ser Tyr Leu Ala Trp Tyr Gln Gln Lys Pro Gly Gln
            165                 170                 175

Ala Pro Arg Leu Leu Ile Tyr Asp Ala Ser Asn Arg Ala Thr Gly Ile
        180                 185                 190

Pro Ala Arg Phe Ser Gly Ser Gly Ser Gly Thr Asp Phe Thr Leu Thr
    195                 200                 205

Ile Ser Ser Leu Glu Pro Glu Asp Phe Ala Val Tyr Tyr Cys Gln Gln
210                 215                 220

Arg Ser Asn Trp Pro Pro Ser Tyr Thr Phe Gly Gln Gly Thr Lys Leu
225                 230                 235                 240

Glu Ile Lys Arg Ala Glu Pro Lys Ser Cys Asp Lys Thr His Thr Cys
            245                 250                 255

Pro Pro Cys Pro Ala Pro Glu Leu Leu Gly Gly Pro Ser Val Phe Leu
        260                 265                 270

Phe Pro Pro Lys Pro Lys Asp Thr Leu Met Ile Ser Arg Thr Pro Glu
    275                 280                 285

Val Thr Cys Val Val Val Asp Val Ser His Glu Asp Pro Glu Val Lys
290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
            325                 330                 335

Thr Val Leu His Gln Asp Trp Leu Asn Gly Lys Glu Tyr Lys Cys Lys
        340                 345                 350

Val Ser Asn Lys Ala Leu Pro Ala Pro Ile Glu Lys Thr Ile Ser Lys
    355                 360                 365

Ala Lys Gly Gln Pro Arg Glu Pro Gln Val Tyr Thr Leu Pro Pro Ser
370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
            405                 410                 415
```

```
Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys Lys Asp Pro
465                 470                 475                 480

Lys Ala Ala Ala Thr Thr Thr Pro Ala Pro Arg Pro Pro Thr Pro Ala
                485                 490                 495

Pro Thr Ile Ala Ser Gln Pro Leu Ser Leu Arg Pro Glu Ala Cys Arg
            500                 505                 510

Pro Ala Ala Gly Gly Ala Val His Thr Arg Gly Leu Asp Phe Ala Cys
        515                 520                 525

Asp Ile Tyr Ile Trp Ala Pro Leu Ala Gly Thr Cys Gly Val Leu Leu
    530                 535                 540

Leu Ser Leu Val Ile Thr Leu Tyr Cys Lys Arg Gly Arg Lys Lys Leu
545                 550                 555                 560

Leu Tyr Ile Phe Lys Gln Pro Phe Met Arg Pro Val Gln Thr Thr Gln
                565                 570                 575

Glu Glu Asp Gly Cys Ser Cys Arg Phe Pro Glu Glu Glu Glu Gly Gly
            580                 585                 590

Cys Glu Leu Arg Val Lys Phe Ser Arg Ser Ala Asp Ala Pro Ala Tyr
        595                 600                 605

Lys Gln Gly Gln Asn Gln Leu Tyr Asn Glu Leu Asn Leu Gly Arg Arg
    610                 615                 620

Glu Glu Tyr Asp Val Leu Asp Lys Arg Arg Gly Arg Asp Pro Glu Met
625                 630                 635                 640

Gly Gly Lys Pro Arg Arg Lys Asn Pro Gln Glu Gly Leu Tyr Asn Glu
                645                 650                 655

Leu Gln Lys Asp Lys Met Ala Glu Ala Tyr Ser Glu Ile Gly Met Lys
            660                 665                 670

Gly Glu Arg Arg Arg Gly Lys Gly His Asp Gly Leu Tyr Gln Gly Leu
        675                 680                 685

Ser Thr Ala Thr Lys Asp Thr Tyr Asp Ala Leu His Met Gln Ala Leu
    690                 695                 700

Pro Pro Arg
705

<210> SEQ ID NO 41
<211> LENGTH: 767
<212> TYPE: PRT
<213> ORGANISM: Artificial Sequence
<220> FEATURE:
<223> OTHER INFORMATION: Synthetic

<400> SEQUENCE: 41

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60
```

```
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Thr Gly Gly Ser Gly Arg Tyr Ala Leu Asp Ile Trp Gly Gln Gly
            100                 105                 110

Thr Met Val Thr Val Ser Ser Gly Gly Gly Ser Gly Gly Gly Gly
        115                 120                 125

Ser Gly Gly Gly Gly Ser Glu Ile Val Leu Thr Gln Ser Pro Ala Thr
130                 135                 140

Leu Ser Leu Ser Pro Gly Glu Arg Ala Thr Leu Ser Cys Arg Ala Ser
145                 150                 155                 160

Gln Ser Val Ser Ser Tyr Leu Ala Trp Tyr Gln Gln Lys Pro Gly Gln
                165                 170                 175

Ala Pro Arg Leu Leu Ile Tyr Asp Ala Ser Asn Arg Ala Thr Gly Ile
            180                 185                 190

Pro Ala Arg Phe Ser Gly Ser Gly Ser Gly Thr Asp Phe Thr Leu Thr
        195                 200                 205

Ile Ser Ser Leu Glu Pro Glu Asp Phe Ala Val Tyr Tyr Cys Gln Gln
210                 215                 220

Arg Ser Asn Trp Pro Pro Ser Tyr Thr Phe Gly Gln Gly Thr Lys Leu
225                 230                 235                 240

Glu Ile Lys Arg Ala Glu Pro Lys Ser Cys Asp Lys Thr His Thr Cys
                245                 250                 255

Pro Pro Cys Pro Ala Pro Glu Leu Leu Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
        355                 360                 365

Ala Lys Gly Gln Pro Arg Glu Pro Gln Val Tyr Thr Leu Pro Pro Ser
370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
450                 455                 460

His Tyr Thr Gln Lys Ser Leu Ser Leu Ser Pro Gly Lys Lys Asp Pro
465                 470                 475                 480

Lys Ala Ala Ala Phe Val Pro Val Phe Leu Pro Ala Lys Pro Thr Thr
```

```
                        485                 490                 495
Thr Pro Ala Pro Arg Pro Pro Thr Pro Ala Pro Thr Ile Ala Ser Gln
            500                 505                 510
Pro Leu Ser Leu Arg Pro Glu Ala Cys Arg Pro Ala Ala Gly Gly Ala
            515                 520                 525
Val His Thr Arg Gly Leu Asp Phe Ala Cys Asp Ile Tyr Ile Trp Ala
            530                 535                 540
Pro Leu Ala Gly Thr Cys Gly Val Leu Leu Ser Leu Val Ile Thr
545                 550                 555                 560
Leu Tyr Cys Asn His Arg Asn Arg Ser Lys Arg Ser Arg Leu Leu His
                565                 570                 575
Ser Asp Tyr Met Asn Met Thr Pro Arg Arg Pro Gly Pro Thr Arg Lys
                580                 585                 590
His Tyr Gln Pro Tyr Ala Pro Pro Arg Asp Phe Ala Ala Tyr Arg Ser
                595                 600                 605
Arg Phe Ser Val Val Lys Arg Gly Arg Lys Lys Leu Leu Tyr Ile Phe
            610                 615                 620
Lys Gln Pro Phe Met Arg Pro Val Gln Thr Thr Gln Glu Glu Asp Gly
625                 630                 635                 640
Cys Ser Cys Arg Phe Pro Glu Glu Glu Glu Gly Gly Cys Glu Leu Arg
                645                 650                 655
Val Lys Phe Ser Arg Ser Ala Asp Ala Pro Ala Tyr Gln Gln Gly Gln
                660                 665                 670
Asn Gln Leu Tyr Asn Glu Leu Asn Leu Gly Arg Arg Glu Glu Tyr Asp
                675                 680                 685
Val Leu Asp Lys Arg Arg Gly Arg Asp Pro Glu Met Gly Gly Lys Pro
            690                 695                 700
Arg Arg Lys Asn Pro Gln Glu Gly Leu Tyr Asn Glu Leu Gln Lys Asp
705                 710                 715                 720
Lys Met Ala Glu Ala Tyr Ser Glu Ile Gly Met Lys Gly Glu Arg Arg
                725                 730                 735
Arg Gly Lys Gly His Asp Gly Leu Tyr Gln Gly Leu Ser Thr Ala Thr
                740                 745                 750
Lys Asp Thr Tyr Asp Ala Leu His Met Gln Ala Leu Pro Pro Arg
                755                 760                 765

<210> SEQ ID NO 42
<211> LENGTH: 714
<212> TYPE: PRT
<213> ORGANISM: Artificial Sequence
<220> FEATURE:
<223> OTHER INFORMATION: Synthetic

<400> SEQUENCE: 42

Gln Val Gln Leu Gln Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
                20                  25                  30
Ala Ile Ser Trp Val Arg Gln Ala Pro Gly Gln Gly Leu Glu Trp Met
            35                  40                  45
Gly Gly Ile Ile Pro Ile Leu Gly Ile Ala Asn Tyr Ala Gln Lys Phe
        50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
```

```
                    85                  90                  95
Ala Arg Gly Gly Ala Gly Gly Ser Gly Ser Tyr Tyr Pro Leu Ile Trp
                100                 105                 110

Gly Gln Gly Thr Thr Val Thr Val Ser Ser Gly Gly Gly Gly Ser Gly
            115                 120                 125

Gly Gly Gly Ser Gly Gly Gly Ser Glu Ile Val Leu Thr Gln Ser
        130                 135                 140

Pro Ala Thr Leu Ser Leu Ser Pro Gly Glu Arg Ala Thr Leu Ser Cys
145                 150                 155                 160

Gly Ala Ser Gln Ser Val Ser Ser Ser Tyr Leu Ala Trp Tyr Gln Gln
                165                 170                 175

Lys Pro Gly Gln Ala Pro Arg Leu Leu Ile Tyr Asp Ala Ser Ser Arg
            180                 185                 190

Ala Thr Gly Ile Pro Ala Arg Phe Ser Gly Ser Gly Ser Gly Thr Asp
        195                 200                 205

Phe Thr Leu Thr Ile Ser Ser Leu Glu Pro Glu Asp Phe Ala Val Tyr
210                 215                 220

Tyr Cys Gln Gln Arg Ser Ser Trp Pro Pro Thr Trp Thr Phe Gly Gln
225                 230                 235                 240

Gly Thr Lys Leu Glu Ile Lys Arg Ala Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
450                 455                 460

Ala Leu His Asn His Tyr Thr Gln Lys Ser Leu Ser Leu Ser Pro Gly
465                 470                 475                 480

Lys Lys Asp Pro Lys Ala Ala Ile Glu Gly Ala Ala Ala Ile
                485                 490                 495

Glu Val Met Tyr Pro Pro Pro Tyr Leu Asp Asn Glu Lys Ser Asn Gly
            500                 505                 510
```

```
Thr Ile Ile His Val Lys Gly Lys His Leu Cys Pro Ser Pro Leu Phe
            515                 520                 525

Pro Gly Pro Ser Lys Pro Phe Trp Val Leu Val Val Val Gly Gly Val
530                 535                 540

Leu Ala Cys Tyr Ser Leu Leu Val Thr Val Ala Phe Ile Ile Phe Trp
545                 550                 555                 560

Val Arg Ser Lys Arg Ser Arg Leu Leu His Ser Asp Tyr Met Asn Met
                565                 570                 575

Thr Pro Arg Arg Pro Gly Pro Thr Arg Lys His Tyr Gln Pro Tyr Ala
            580                 585                 590

Pro Pro Arg Asp Phe Ala Ala Tyr Arg Ser Arg Val Lys Phe Ser Arg
            595                 600                 605

Ser Ala Asp Ala Pro Ala Tyr Gln Gln Gly Gln Asn Gln Leu Tyr Asn
            610                 615                 620

Glu Leu Asn Leu Gly Arg Arg Glu Glu Tyr Asp Val Leu Asp Lys Arg
625                 630                 635                 640

Arg Gly Arg Asp Pro Glu Met Gly Gly Lys Pro Arg Arg Lys Asn Pro
                645                 650                 655

Gln Glu Gly Leu Tyr Asn Glu Leu Gln Lys Asp Lys Met Ala Glu Ala
            660                 665                 670

Tyr Ser Glu Ile Gly Met Lys Gly Glu Arg Arg Arg Gly Lys Gly His
            675                 680                 685

Asp Gly Leu Tyr Gln Gly Leu Ser Thr Ala Thr Lys Asp Thr Tyr Asp
            690                 695                 700

Ala Leu His Met Gln Ala Leu Pro Pro Arg
705                 710

<210> SEQ ID NO 43
<211> LENGTH: 711
<212> TYPE: PRT
<213> ORGANISM: Artificial Sequence
<220> FEATURE:
<223> OTHER INFORMATION: Synthetic

<400> SEQUENCE: 43

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Leu Gly Ile Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Ala Gly Gly Ser Gly Ser Tyr Tyr Pro Leu Ile Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Gly Ser Glu Ile Val Leu Thr Gln Ser
    130                 135                 140

Pro Ala Thr Leu Ser Leu Ser Pro Gly Glu Arg Ala Thr Leu Ser Cys
145                 150                 155                 160
```

-continued

Gly Ala Ser Gln Ser Val Ser Ser Tyr Leu Ala Trp Tyr Gln Gln
                    165                 170                 175
Lys Pro Gly Gln Ala Pro Arg Leu Leu Ile Tyr Asp Ala Ser Ser Arg
                180                 185                 190
Ala Thr Gly Ile Pro Ala Arg Phe Ser Gly Ser Gly Ser Gly Thr Asp
                195                 200                 205
Phe Thr Leu Thr Ile Ser Ser Leu Glu Pro Glu Asp Phe Ala Val Tyr
            210                 215                 220
Tyr Cys Gln Gln Arg Ser Ser Trp Pro Pro Thr Trp Thr Phe Gly Gln
225                 230                 235                 240
Gly Thr Lys Leu Glu Ile Lys Arg Ala Glu Pro Lys Ser Cys Asp Lys
                245                 250                 255
Thr His Thr Cys Pro Pro Cys Pro Ala Pro Glu Leu Leu Gly Gly Pro
                260                 265                 270
Ser Val Phe Leu Phe Pro Pro Lys Pro Lys Asp Thr Leu Met Ile Ser
            275                 280                 285
Arg Thr Pro Glu Val Thr Cys Val Val Val Asp Val Ser His Glu Asp
290                 295                 300
Pro Glu Val Lys Phe Asn Trp Tyr Val Asp Gly Val Glu Val His Asn
305                 310                 315                 320
Ala Lys Thr Lys Pro Arg Glu Glu Gln Tyr Asn Ser Thr Tyr Arg Val
                325                 330                 335
Val Ser Val Leu Thr Val Leu His Gln Asp Trp Leu Asn Gly Lys Glu
            340                 345                 350
Tyr Lys Cys Lys Val Ser Asn Lys Ala Leu Pro Ala Pro Ile Glu Lys
        355                 360                 365
Thr Ile Ser Lys Ala Lys Gly Gln Pro Arg Glu Pro Gln Val Tyr Thr
    370                 375                 380
Leu Pro Pro Ser Arg Asp Glu Leu Thr Lys Asn Gln Val Ser Leu Thr
385                 390                 395                 400
Cys Leu Val Lys Gly Phe Tyr Pro Ser Asp Ile Ala Val Glu Trp Glu
                405                 410                 415
Ser Asn Gly Gln Pro Glu Asn Asn Tyr Lys Thr Thr Pro Pro Val Leu
                420                 425                 430
Asp Ser Asp Gly Ser Phe Phe Leu Tyr Ser Lys Leu Thr Val Asp Lys
            435                 440                 445
Ser Arg Trp Gln Gln Gly Asn Val Phe Ser Cys Ser Val Met His Glu
        450                 455                 460
Ala Leu His Asn His Tyr Thr Gln Lys Ser Leu Ser Leu Ser Pro Gly
465                 470                 475                 480
Lys Lys Asp Pro Lys Ala Ala Ala Thr Thr Thr Pro Ala Pro Arg Pro
                485                 490                 495
Pro Thr Pro Ala Pro Thr Ile Ala Ser Gln Pro Leu Ser Leu Arg Pro
                500                 505                 510
Glu Ala Cys Arg Pro Ala Ala Gly Gly Ala Val His Thr Arg Gly Leu
            515                 520                 525
Asp Phe Ala Cys Asp Ile Tyr Ile Trp Ala Pro Leu Ala Gly Thr Cys
530                 535                 540
Gly Val Leu Leu Leu Ser Leu Val Ile Thr Leu Tyr Cys Lys Arg Gly
545                 550                 555                 560
Arg Lys Lys Leu Leu Tyr Ile Phe Lys Gln Pro Phe Met Arg Pro Val
                565                 570                 575

```
Gln Thr Thr Gln Glu Glu Asp Gly Cys Ser Cys Arg Phe Pro Glu Glu
            580                 585                 590

Glu Glu Gly Gly Cys Glu Leu Arg Val Lys Phe Ser Arg Ser Ala Asp
        595                 600                 605

Ala Pro Ala Tyr Lys Gln Gly Gln Asn Gln Leu Tyr Asn Glu Leu Asn
    610                 615                 620

Leu Gly Arg Arg Glu Glu Tyr Asp Val Leu Asp Lys Arg Arg Gly Arg
625                 630                 635                 640

Asp Pro Glu Met Gly Gly Lys Pro Arg Arg Lys Asn Pro Gln Glu Gly
                645                 650                 655

Leu Tyr Asn Glu Leu Gln Lys Asp Lys Met Ala Glu Ala Tyr Ser Glu
            660                 665                 670

Ile Gly Met Lys Gly Glu Arg Arg Arg Gly Lys Gly His Asp Gly Leu
        675                 680                 685

Tyr Gln Gly Leu Ser Thr Ala Thr Lys Asp Thr Tyr Asp Ala Leu His
    690                 695                 700

Met Gln Ala Leu Pro Pro Arg
705                 710

<210> SEQ ID NO 44
<211> LENGTH: 771
<212> TYPE: PRT
<213> ORGANISM: Artificial Sequence
<220> FEATURE:
<223> OTHER INFORMATION: Synthetic

<400> SEQUENCE: 44

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Ala Gly Gly Ser Gly Ser Tyr Tyr Pro Leu Ile Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Ser Glu Ile Val Leu Thr Gln Ser
    130                 135                 140

Pro Ala Thr Leu Ser Leu Ser Pro Gly Glu Arg Ala Thr Leu Ser Cys
145                 150                 155                 160

Gly Ala Ser Gln Ser Val Ser Ser Ser Tyr Leu Ala Trp Tyr Gln Gln
                165                 170                 175

Lys Pro Gly Gln Ala Pro Arg Leu Leu Ile Tyr Asp Ala Ser Ser Arg
            180                 185                 190

Ala Thr Gly Ile Pro Ala Arg Phe Ser Gly Ser Gly Ser Gly Thr Asp
        195                 200                 205

Phe Thr Leu Thr Ile Ser Ser Leu Glu Pro Glu Asp Phe Ala Val Tyr
    210                 215                 220
```

-continued

Tyr Cys Gln Gln Arg Ser Ser Trp Pro Pro Thr Trp Thr Phe Gly Gln
225                 230                 235                 240

Gly Thr Lys Leu Glu Ile Lys Arg Ala Glu Pro Lys Ser Cys Asp Lys
            245                 250                 255

Thr His Thr Cys Pro Pro Cys Pro Ala Pro Glu Leu Leu Gly Gly Pro
        260                 265                 270

Ser Val Phe Leu Phe Pro Pro Lys Pro Lys Asp Thr Leu Met Ile Ser
    275                 280                 285

Arg Thr Pro Glu Val Thr Cys Val Val Val Asp Val Ser His Glu Asp
290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
            325                 330                 335

Val Ser Val Leu Thr Val Leu His Gln Asp Trp Leu Asn Gly Lys Glu
        340                 345                 350

Tyr Lys Cys Lys Val Ser Asn Lys Ala Leu Pro Ala Pro Ile Glu Lys
    355                 360                 365

Thr Ile Ser Lys Ala Lys Gly Gln Pro Arg Glu Pro Gln Val Tyr Thr
370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
            405                 410                 415

Ser Asn Gly Gln Pro Glu Asn Asn Tyr Lys Thr Thr Pro Pro Val Leu
        420                 425                 430

Asp Ser Asp Gly Ser Phe Phe Leu Tyr Ser Lys Leu Thr Val Asp Lys
    435                 440                 445

Ser Arg Trp Gln Gln Gly Asn Val Phe Ser Cys Ser Val Met His Glu
450                 455                 460

Ala Leu His Asn His Tyr Thr Gln Lys Ser Leu Ser Leu Ser Pro Gly
465                 470                 475                 480

Lys Lys Asp Pro Lys Ala Ala Ala Phe Val Pro Val Phe Leu Pro Ala
            485                 490                 495

Lys Pro Thr Thr Thr Pro Ala Pro Arg Pro Pro Thr Pro Ala Pro Thr
        500                 505                 510

Ile Ala Ser Gln Pro Leu Ser Leu Arg Pro Glu Ala Cys Arg Pro Ala
    515                 520                 525

Ala Gly Gly Ala Val His Thr Arg Gly Leu Asp Phe Ala Cys Asp Ile
530                 535                 540

Tyr Ile Trp Ala Pro Leu Ala Gly Thr Cys Gly Val Leu Leu Leu Ser
545                 550                 555                 560

Leu Val Ile Thr Leu Tyr Cys Asn His Arg Asn Arg Ser Lys Arg Ser
            565                 570                 575

Arg Leu Leu His Ser Asp Tyr Met Asn Met Thr Pro Arg Arg Pro Gly
        580                 585                 590

Pro Thr Arg Lys His Tyr Gln Pro Tyr Ala Pro Pro Arg Asp Phe Ala
    595                 600                 605

Ala Tyr Arg Ser Arg Phe Ser Val Val Lys Arg Gly Arg Lys Lys Leu
610                 615                 620

Leu Tyr Ile Phe Lys Gln Pro Phe Met Arg Pro Val Gln Thr Thr Gln
625                 630                 635                 640

Glu Glu Asp Gly Cys Ser Cys Arg Phe Pro Glu Glu Glu Glu Gly Gly

```
                      645                 650                 655
Cys Glu Leu Arg Val Lys Phe Ser Arg Ser Ala Asp Ala Pro Ala Tyr
            660                 665                 670

Gln Gln Gly Gln Asn Gln Leu Tyr Asn Glu Leu Asn Leu Gly Arg Arg
        675                 680                 685

Glu Glu Tyr Asp Val Leu Asp Lys Arg Arg Gly Arg Asp Pro Glu Met
    690                 695                 700

Gly Gly Lys Pro Arg Arg Lys Asn Pro Gln Glu Gly Leu Tyr Asn Glu
705                 710                 715                 720

Leu Gln Lys Asp Lys Met Ala Glu Ala Tyr Ser Glu Ile Gly Met Lys
                725                 730                 735

Gly Glu Arg Arg Arg Gly Lys Gly His Asp Gly Leu Tyr Gln Gly Leu
            740                 745                 750

Ser Thr Ala Thr Lys Asp Thr Tyr Asp Ala Leu His Met Gln Ala Leu
        755                 760                 765

Pro Pro Arg
    770

<210> SEQ ID NO 45
<211> LENGTH: 701
<212> TYPE: PRT
<213> ORGANISM: Artificial Sequence
<220> FEATURE:
<223> OTHER INFORMATION: Synthetic

<400> SEQUENCE: 45

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Gly Ala Phe Asp Ile Trp Gly Gln Gly Thr Met
            100                 105                 110

Val Thr Val Ser Ser Gly Gly Gly Ser Gly Gly Gly Gly Ser Gly
        115                 120                 125

Gly Gly Gly Ser Glu Ile Val Leu Thr Gln Ser Pro Gly Thr Leu Ser
    130                 135                 140

Leu Ser Pro Gly Glu Arg Ala Thr Leu Ser Cys Arg Ala Ser Gln Ser
145                 150                 155                 160

Val Gly Gly Tyr Leu Ala Trp Tyr Gln Gln Lys Pro Gly Gln Ala Pro
                165                 170                 175

Arg Leu Leu Ile Tyr Asp Ala Ser Asn Arg Ala Thr Gly Ile Pro Ala
            180                 185                 190

Arg Phe Ser Gly Ser Gly Ser Gly Thr Asp Phe Thr Leu Thr Ile Ser
        195                 200                 205

Ser Leu Glu Pro Glu Asp Phe Ala Val Tyr Tyr Cys Gln Gln Arg Asn
    210                 215                 220

Asn Trp Pro Pro Met Tyr Thr Phe Gly Gln Gly Thr Lys Leu Glu Ile
```

-continued

```
            225                 230                 235                 240

Lys Arg Ala Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
                260                 265                 270

Pro Lys Pro Lys Asp Thr Leu Met Ile Ser Arg Thr Pro Glu Val Thr
                275                 280                 285

Cys Val Val Val Asp Val Ser His Glu Asp Pro Glu Val Lys Phe Asn
        290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
                340                 345                 350

Asn Lys Ala Leu Pro Ala Pro Ile Glu Lys Thr Ile Ser Lys Ala Lys
                355                 360                 365

Gly Gln Pro Arg Glu Pro Gln Val Tyr Thr Leu Pro Pro Ser Arg Asp
        370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
                420                 425                 430

Phe Leu Tyr Ser Lys Leu Thr Val Asp Lys Ser Arg Trp Gln Gln Gly
                435                 440                 445

Asn Val Phe Ser Cys Ser Val Met His Glu Ala Leu His Asn His Tyr
        450                 455                 460

Thr Gln Lys Ser Leu Ser Leu Ser Pro Gly Lys Lys Asp Pro Lys Ala
465                 470                 475                 480

Ala Ala Ile Glu Val Met Tyr Pro Pro Tyr Leu Asp Asn Glu Lys
                485                 490                 495

Ser Asn Gly Thr Ile Ile His Val Lys Gly Lys His Leu Cys Pro Ser
                500                 505                 510

Pro Leu Phe Pro Gly Pro Ser Lys Pro Phe Trp Val Leu Val Val Val
                515                 520                 525

Gly Gly Val Leu Ala Cys Tyr Ser Leu Leu Val Thr Val Ala Phe Ile
        530                 535                 540

Ile Phe Trp Val Arg Ser Lys Arg Ser Arg Leu Leu His Ser Asp Tyr
545                 550                 555                 560

Met Asn Met Thr Pro Arg Arg Pro Gly Pro Thr Arg Lys His Tyr Gln
                565                 570                 575

Pro Tyr Ala Pro Pro Arg Asp Phe Ala Ala Tyr Arg Ser Arg Val Lys
                580                 585                 590

Phe Ser Arg Ser Ala Asp Ala Pro Ala Tyr Gln Gln Gly Gln Asn Gln
                595                 600                 605

Leu Tyr Asn Glu Leu Asn Leu Gly Arg Arg Glu Glu Tyr Asp Val Leu
        610                 615                 620

Asp Lys Arg Arg Gly Arg Asp Pro Glu Met Gly Gly Lys Pro Arg Arg
625                 630                 635                 640

Lys Asn Pro Gln Glu Gly Leu Tyr Asn Glu Leu Gln Lys Asp Lys Met
                645                 650                 655
```

```
Ala Glu Ala Tyr Ser Glu Ile Gly Met Lys Gly Glu Arg Arg Gly
            660                 665                 670

Lys Gly His Asp Gly Leu Tyr Gln Gly Leu Ser Thr Ala Thr Lys Asp
        675                 680                 685

Thr Tyr Asp Ala Leu His Met Gln Ala Leu Pro Pro Arg
    690                 695                 700

<210> SEQ ID NO 46
<211> LENGTH: 705
<212> TYPE: PRT
<213> ORGANISM: Artificial Sequence
<220> FEATURE:
<223> OTHER INFORMATION: Synthetic

<400> SEQUENCE: 46

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Gly Ala Phe Asp Ile Trp Gly Gln Gly Thr Met
            100                 105                 110

Val Thr Val Ser Ser Gly Gly Gly Gly Ser Gly Gly Gly Ser Gly
            115                 120                 125

Gly Gly Gly Ser Glu Ile Val Leu Thr Gln Ser Pro Gly Thr Leu Ser
    130                 135                 140

Leu Ser Pro Gly Glu Arg Ala Thr Leu Ser Cys Arg Ala Ser Gln Ser
145                 150                 155                 160

Val Gly Gly Tyr Leu Ala Trp Tyr Gln Gln Lys Pro Gly Gln Ala Pro
                165                 170                 175

Arg Leu Leu Ile Tyr Asp Ala Ser Asn Arg Ala Thr Gly Ile Pro Ala
            180                 185                 190

Arg Phe Ser Gly Ser Gly Ser Gly Thr Asp Phe Thr Leu Thr Ile Ser
        195                 200                 205

Ser Leu Glu Pro Glu Asp Phe Ala Val Tyr Tyr Cys Gln Gln Arg Asn
    210                 215                 220

Asn Trp Pro Pro Met Tyr Thr Phe Gly Gln Gly Thr Lys Leu Glu Ile
225                 230                 235                 240

Lys Arg Ala Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320
```

Glu Glu Gln Tyr Asn Ser Thr Tyr Arg Val Ser Val Leu Thr Val
                    325                 330                 335

Leu His Gln Asp Trp Leu Asn Gly Lys Glu Tyr Lys Cys Lys Val Ser
                340                 345                 350

Asn Lys Ala Leu Pro Ala Pro Ile Glu Lys Thr Ile Ser Lys Ala Lys
            355                 360                 365

Gly Gln Pro Arg Glu Pro Gln Val Tyr Thr Leu Pro Pro Ser Arg Asp
        370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys Lys Asp Pro Lys Ala
465                 470                 475                 480

Ala Ala Thr Thr Thr Pro Ala Pro Arg Pro Pro Thr Pro Ala Pro Thr
                485                 490                 495

Ile Ala Ser Gln Pro Leu Ser Leu Arg Pro Glu Ala Cys Arg Pro Ala
            500                 505                 510

Ala Gly Gly Ala Val His Thr Arg Gly Leu Asp Phe Ala Cys Asp Ile
        515                 520                 525

Tyr Ile Trp Ala Pro Leu Ala Gly Thr Cys Gly Val Leu Leu Leu Ser
    530                 535                 540

Leu Val Ile Thr Leu Tyr Cys Lys Arg Gly Arg Lys Lys Leu Leu Tyr
545                 550                 555                 560

Ile Phe Lys Gln Pro Phe Met Arg Pro Val Gln Thr Thr Gln Glu Glu
                565                 570                 575

Asp Gly Cys Ser Cys Arg Phe Pro Glu Glu Glu Glu Gly Gly Cys Glu
            580                 585                 590

Leu Arg Val Lys Phe Ser Arg Ser Ala Asp Ala Pro Ala Tyr Lys Gln
        595                 600                 605

Gly Gln Asn Gln Leu Tyr Asn Glu Leu Asn Leu Gly Arg Arg Glu Glu
    610                 615                 620

Tyr Asp Val Leu Asp Lys Arg Arg Gly Arg Asp Pro Glu Met Gly Gly
625                 630                 635                 640

Lys Pro Arg Arg Lys Asn Pro Gln Glu Gly Leu Tyr Asn Glu Leu Gln
                645                 650                 655

Lys Asp Lys Met Ala Glu Ala Tyr Ser Glu Ile Gly Met Lys Gly Glu
            660                 665                 670

Arg Arg Arg Gly Lys Gly His Asp Gly Leu Tyr Gln Gly Leu Ser Thr
        675                 680                 685

Ala Thr Lys Asp Thr Tyr Asp Ala Leu His Met Gln Ala Leu Pro Pro
690                 695                 700

Arg
705

<210> SEQ ID NO 47
<211> LENGTH: 765

```
<212> TYPE: PRT
<213> ORGANISM: Artificial Sequence
<220> FEATURE:
<223> OTHER INFORMATION: Synthetic

<400> SEQUENCE: 47

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Gly Ala Phe Asp Ile Trp Gly Gln Gly Thr Met
            100                 105                 110

Val Thr Val Ser Ser Gly Gly Gly Gly Ser Gly Gly Gly Gly Ser Gly
            115                 120                 125

Gly Gly Gly Ser Glu Ile Val Leu Thr Gln Ser Pro Gly Thr Leu Ser
    130                 135                 140

Leu Ser Pro Gly Glu Arg Ala Thr Leu Ser Cys Arg Ala Ser Gln Ser
145                 150                 155                 160

Val Gly Gly Tyr Leu Ala Trp Tyr Gln Gln Lys Pro Gly Gln Ala Pro
                165                 170                 175

Arg Leu Leu Ile Tyr Asp Ala Ser Asn Arg Ala Thr Gly Ile Pro Ala
            180                 185                 190

Arg Phe Ser Gly Ser Gly Ser Gly Thr Asp Phe Thr Leu Thr Ile Ser
        195                 200                 205

Ser Leu Glu Pro Glu Asp Phe Ala Val Tyr Tyr Cys Gln Gln Arg Asn
    210                 215                 220

Asn Trp Pro Pro Met Tyr Thr Phe Gly Gln Gly Thr Lys Leu Glu Ile
225                 230                 235                 240

Lys Arg Ala Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380
```

```
Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
            405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
            435                 440                 445

Asn Val Phe Ser Cys Ser Val Met His Glu Ala Leu His Asn His Tyr
        450                 455                 460

Thr Gln Lys Ser Leu Ser Leu Ser Pro Gly Lys Lys Asp Pro Lys Ala
465                 470                 475                 480

Ala Ala Phe Val Pro Val Phe Leu Pro Ala Lys Pro Thr Thr Thr Pro
            485                 490                 495

Ala Pro Arg Pro Pro Thr Pro Ala Pro Thr Ile Ala Ser Gln Pro Leu
            500                 505                 510

Ser Leu Arg Pro Glu Ala Cys Arg Pro Ala Ala Gly Gly Ala Val His
            515                 520                 525

Thr Arg Gly Leu Asp Phe Ala Cys Asp Ile Tyr Ile Trp Ala Pro Leu
530                 535                 540

Ala Gly Thr Cys Gly Val Leu Leu Leu Ser Leu Val Ile Thr Leu Tyr
545                 550                 555                 560

Cys Asn His Arg Asn Arg Ser Lys Arg Ser Arg Leu Leu His Ser Asp
            565                 570                 575

Tyr Met Asn Met Thr Pro Arg Arg Pro Gly Pro Thr Arg Lys His Tyr
            580                 585                 590

Gln Pro Tyr Ala Pro Pro Arg Asp Phe Ala Ala Tyr Arg Ser Arg Phe
            595                 600                 605

Ser Val Val Lys Arg Gly Arg Lys Lys Leu Leu Tyr Ile Phe Lys Gln
            610                 615                 620

Pro Phe Met Arg Pro Val Gln Thr Thr Gln Glu Glu Asp Gly Cys Ser
625                 630                 635                 640

Cys Arg Phe Pro Glu Glu Glu Glu Gly Gly Cys Glu Leu Arg Val Lys
            645                 650                 655

Phe Ser Arg Ser Ala Asp Ala Pro Ala Tyr Gln Gln Gly Gln Asn Gln
            660                 665                 670

Leu Tyr Asn Glu Leu Asn Leu Gly Arg Arg Glu Glu Tyr Asp Val Leu
            675                 680                 685

Asp Lys Arg Arg Gly Arg Asp Pro Glu Met Gly Gly Lys Pro Arg Arg
            690                 695                 700

Lys Asn Pro Gln Glu Gly Leu Tyr Asn Glu Leu Gln Lys Asp Lys Met
705                 710                 715                 720

Ala Glu Ala Tyr Ser Glu Ile Gly Met Lys Gly Glu Arg Arg Arg Gly
            725                 730                 735

Lys Gly His Asp Gly Leu Tyr Gln Gly Leu Ser Thr Ala Thr Lys Asp
            740                 745                 750

Thr Tyr Asp Ala Leu His Met Gln Ala Leu Pro Pro Arg
            755                 760                 765

<210> SEQ ID NO 48
<211> LENGTH: 2112
<212> TYPE: DNA
<213> ORGANISM: Artificial Sequence
<220> FEATURE:
<223> OTHER INFORMATION: Synthetic
```

<400> SEQUENCE: 48

```
caagtccaac ttcagcagtc aggggcggag gtgaagaagc cgggctcctc cgtaaaggtg      60
tcgtgcaaag catcgggcgg tacattctcc tcctatgcga tctcatgggt gcgacaggca     120
cccgggcagg ggttggaatg gatgggtggt atcattccca ttctcgggat cgcgaactac     180
gcgcagaagt ttcaaggcag agtaacaatt actgcagacg agtccacctc aaccgcctat     240
atggaactgt cgtcacttcg gtccgaagat acagccgtgt actattgtgc aacgggaggc     300
agcgggaggt atgcccttga catttgggga caggggacaa tggtcacagt aagctccgga     360
ggtgggggat caggaggcgg tggatcgggt ggggaggat cggaaattgt actcactcag      420
tcaccggcga ctctctccct cagcccggga gagcgggcca ccttgtcatg cagagccagc     480
cagagcgtat catcctatct tgcgtggtat cagcaaaaac ccgtcaggc cccaaggttg      540
ctgatctacg atgcgtcgaa tcgcgcgaca ggaatccctg ctaggttctc cgggtcgggc     600
tcggggaccg actttacgct tacgatcagc tcgctggaac cggaggactt cgccgtctac     660
tactgccagc agcggtcgaa ttggccgcct tcctacacat ttggacaagg aacaaagctg     720
gaaatcaaga gagcggaacc gaaatcatgc gacaaaacgc acacctgtcc cccttgtccc     780
gctcccgagt tgctgggagg accgtcggtg ttcctctttc cgccaaaacc caaagatacg     840
ttgatgatct cgcgcacgcc cgaggtgaca tgtgtggtag tcgatgtctc gcacgaggac     900
cccgaagtca agttcaattg gtacgtggac ggggtggaag tccataatgc caagacgaaa     960
cctcgggagg agcagtacaa ctccacatat cgcgtagtct cggtgctcac cgtactgcat    1020
caggactggc ttaacggaaa ggaatacaag tgcaaagtgt caaacaaggc gttgccggca    1080
ccgattgaga aaacgatctc caaagccaag gggcaacccc gcgagcccca ggtctatact    1140
ctccccgccgt cgcgagatga gctcacgaag aaccaagtct cgcttacgtg cctcgtgaag    1200
ggtttctacc caagcgatat tgcggtggag tgggagagca atggacagcc ggagaacaac    1260
tataagacta ccccaccccgt gcttgactcg gatggcagct ctttctgta ctcgaaactg    1320
accgtggaca aatcgagatg gcaacagggg aatgtctttt catgttccgt gatgcacgag    1380
gcgctccaca accactacac gcagaagagc ttgtcattga gcccagggaa gaaagaccca    1440
aaggcggccg caattgaagt tatgtatcct cctccttacc tagacaatga aagagcaat     1500
ggaaccatta tccatgtgaa agggaaacac ctttgtccaa gtccccctatt tcccggacct    1560
tctaagcccct tttgggtgct ggtggtggtt ggggagtcc tggcttgcta tagcttgcta    1620
gtaacagtgg cctttattat tttctgggtg aggagtaaga ggagcaggct cctgcacagt    1680
gactacatga acatgactcc ccgccgcccc gggcccaccc gcaagcatta ccagccctat    1740
gccccaccac gcgacttcgc agcctatcgc tccagtgta agttcagcag gagcgcagac    1800
gcccccgcgt accagcaggg ccagaaccag ctctataacg agctcaatct aggacgaaga    1860
gaggagtacg atgttttgga caagagacgt ggccgggacc ctgagatggg gggaaagccg    1920
agaaggaaga accctcagga aggcctgtac aatgaactgc agaaagataa gatggcggag    1980
gcctacagtg agattgggat gaaaggcgag cgccggaggg gcaagggca cgatggcctt    2040
taccagggtc tcagtacagc caccaaggac acctacgacg cccttcacat gcaggccctg    2100
ccccctcgct aa                                                       2112
```

<210> SEQ ID NO 49
<211> LENGTH: 2124
<212> TYPE: DNA

<213> ORGANISM: Artificial Sequence
<220> FEATURE:
<223> OTHER INFORMATION: Synthetic

<400> SEQUENCE: 49

```
caagtccaac ttcagcagtc aggggcggag gtgaagaagc cgggctcctc cgtaaaggtg      60
tcgtgcaaag catcgggcgg tacattctcc tcctatgcga tctcatgggt gcgacaggca     120
cccgggcagg ggttggaatg gatgggtggt atcattccca ttctcgggat cgcgaactac     180
gcgcagaagt ttcaaggcag agtaacaatt actgcagacg agtccacctc aaccgcctat     240
atggaactgt cgtcacttcg gtccgaagat acagccgtgt actattgtgc aacgggaggc     300
agcgggaggt atgcccttga catttgggga caggggacaa tggtcacagt aagctccgga     360
ggtgggggat caggaggcgg tggatcgggt ggggaggat cggaaattgt actcactcag     420
tcaccggcga ctctctccct cagcccggga gagcgggcca ccttgtcatg cagagccagc     480
cagagcgtat catcctatct tgcgtggtat cagcaaaaac ccggtcaggc cccaaggttg     540
ctgatctacg atgcgtcgaa tcgcgcgaca ggaatccctg ctaggttctc cgggtcgggc     600
tcggggaccg actttacgct tacgatcagc tcgctggaac cggaggactt cgccgtctac     660
tactgccagc agcggtcgaa ttggccgcct tcctacacat ttggacaagg aacaaagctg     720
gaaatcaaga gagcggaacc gaaatcatgc gacaaaacgc acacctgtcc cccttgtccc     780
gctcccgagt tgctgggagg accgtcggtg ttcctctttc cgccaaaacc caaagatacg     840
ttgatgatct cgcgcacgcc cgaggtgaca tgtgtggtag tcgatgtctc gcacgaggac     900
cccgaagtca agttcaattg gtacgtgac gggtgaag tccataatgc caagacgaaa     960
cctcgggagg agcagtacaa ctccacatat cgcgtagtct cggtgctcac cgtactgcat    1020
caggactggc ttaacggaaa ggaatacaag tgcaaagtgt caaacaaggc gttgccggca    1080
ccgattgaga aaacgatctc caaagccaag gggcaacccc gcgagcccca ggtctatact    1140
ctcccgccgt cgcgagatga gctcacgaag aaccaagtct cgcttacgtg cctcgtgaag    1200
ggtttctacc caagcgatat tgcggtggag tgggagagca atggacagcc ggagaacaac    1260
tataagacta ccccacccgt gcttgactcg gatggcagct tctttctgta ctcgaaactg    1320
accgtggaca aatcgagatg gcaacagggg aatgtctttt catgttccgt gatgcacgag    1380
gcgctccaca accactacac gcagaagagc ttgtcattga gcccagggaa gaaagaccca    1440
aaggcggccg caaccacgac gccagcgccg cgaccaccaa caccggcgcc caccatcgcg    1500
tcgcagcccc tgtccctgcg cccagaggcg tgccggccag cggcgggggg cgcagtgcac    1560
acgagggggc tggacttcgc ctgtgatatc tacatctggg cgcccttggc cgggacttgt    1620
ggggtccttc tcctgtcact ggttatcacc ctttactgca acggggcag aaagaaactc    1680
ctgtatatat tcaaacaacc atttatgaga ccagtacaaa ctactcaaga ggaagatggc    1740
tgtagctgcc gatttccaga agaagaagaa ggaggatgtg aactgagagt gaagttcagc    1800
aggagcgcag acgcccccgc gtacaagcag ggccagaacc agctctataa cgagctcaat    1860
ctaggacgaa gagaggagta cgatgttttg gacaagagac gtggccggga ccctgagatg    1920
ggggaaagc cgagaaggaa gaaccctcag gaaggcctgt acaatgaact gcagaaagat    1980
aagatggcgg aggcctacag tgagattggg atgaaggcg agcgccggag gggcaagggg    2040
cacgatggcc tttaccaggg tctcagtaca gccaccaagg acacctacga cgcccttcac    2100
atgcaggccc tgccccctcg ctaa                                          2124
```

```
<210> SEQ ID NO 50
<211> LENGTH: 2304
<212> TYPE: DNA
<213> ORGANISM: Artificial Sequence
<220> FEATURE:
<223> OTHER INFORMATION: Synthetic

<400> SEQUENCE: 50
caagtccaac ttcagcagtc aggggcggag gtgaagaagc cgggctcctc cgtaaaggtg      60
tcgtgcaaag catcgggcgg tacattctcc tcctatgcga tctcatgggt gcgacaggca     120
cccgggcagg ggttggaatg gatgggtggt atcattccca ttctcgggat cgcgaactac     180
gcgcagaagt tcaaggcag agtaacaatt actgcagacg agtccacctc aaccgcctat     240
atggaactgt cgtcacttcg gtccgaagat acagccgtgt actattgtgc aacgggaggc     300
agcgggaggt atgcccttga catttgggga caggggacaa tggtcacagt aagctccgga     360
ggtgggggat caggaggcgg tggatcgggt ggggaggat cggaaattgt actcactcag     420
tcaccggcga ctctctccct cagcccggga gagcgggcca ccttgtcatg cagagccagc     480
cagagcgtat catcctatct tgcgtggtat cagcaaaaac ccggtcaggc cccaaggttg     540
ctgatctacg atgcgtcgaa tcgcgcgaca ggaatccctg ctaggttctc cgggtcgggc     600
tcggggaccg actttacgct tacgatcagc tcgctggaac cggaggactt cgccgtctac     660
tactgccagc agcggtcgaa ttggccgcct tcctacacat ttggacaagg aacaaagctg     720
gaaatcaaga gagcggaacc gaaatcatgc gacaaaacgc acacctgtcc cccttgtccc     780
gctcccgagt tgctgggagg accgtcggtg ttcctctttc cgccaaaacc caaagatacg     840
ttgatgatct cgcgcacgcc cgaggtgaca tgtgtggtag tcgatgtctc gcacgaggac     900
cccgaagtca agttcaattg gtacgtggac ggggtggaag tccataatgc caagacgaaa     960
cctcgggagg agcagtacaa ctccacatat cgcgtagtct cggtgctcac cgtactgcat    1020
caggactggc ttaacggaaa ggaatacaag tgcaaagtgt caaacaaggc gttgccggca    1080
ccgattgaga aaacgatctc caaagccaag gggcaacccc gcgagcccca ggtctatact    1140
ctcccgccgt cgcgagatga gctcacgaag aaccaagtct cgcttacgtg cctcgtgaag    1200
ggtttctacc caagcgatat tgcggtggag tgggagagca atggacagcc ggagaacaac    1260
tataagacta ccccacccgt gcttgactcg gatggcagct tctttctgta ctcgaaactg    1320
accgtggaca atcgagatg gcaacagggg aatgtctttt catgttccgt gatgcacgag    1380
gcgctccaca accactacac gcagaagagc ttgtcattga gcccagggaa gaaagaccca    1440
aaggcggccg cattcgtgcc ggtcttcctg ccagcgaagc ccaccacgac gccagcgccg    1500
cgaccaccaa caccggcgcc caccatcgcg tcgcagcccc tgtccctgcg cccagaggcg    1560
tgccggccag cggcggggg cgcagtcac acgaggggc tggacttcgc ctgtgatatc    1620
tacatctggg cgccccttggc cgggacttgt ggggtccttc tcctgtcact ggttatcacc    1680
ctttactgca accacaggaa caggagtaag aggagcaggc tcctgcacag tgactacatg    1740
aacatgactc cccgccgccc cgggcccacc cgcaagcatt accagcccta tgccccacca    1800
cgcgacttcg cagcctatcg ctcccgtttc tctgttgtta acggggcag aaagaagctc    1860 ctgtatatat tcaaacaacc atttatgaga ccagtacaaa ctactcaaga ggaagatggc    1920
tgtagctgcc gatttccaga agaagaagaa ggaggatgtg aactgagagt gaagttcagc    1980
aggagcgcag acgccccgc gtaccagcag ggccagaacc agctctataa cgagctcaat    2040
ctaggacgaa gagaggagta cgatgttttg gacaagagac gtggccggga ccctgagatg    2100
```

```
ggggaaagc cgagaaggaa gaaccctcag gaaggcctgt acaatgaact gcagaaagat    2160
aagatggcgg aggcctacag tgagattggg atgaaaggcg agcgccggag gggcaagggg    2220
cacgatggcc tttaccaggg tctcagtaca gccaccaagg acacctacga cgcccttcac    2280
atgcaggccc tgcccctcg ctaa                                             2304

<210> SEQ ID NO 51
<211> LENGTH: 2112
<212> TYPE: DNA
<213> ORGANISM: Artificial Sequence
<220> FEATURE:
<223> OTHER INFORMATION: Synthetic

<400> SEQUENCE: 51
caagtccaac ttcagcagtc aggggcggag gtgaagaagc cgggctcctc cgtaaaggtg      60
tcgtgcaaag catcgggcgg tacattctcc tcctatgcga tctcatgggt gcgacaggca     120
cccgggcagg ggttgaatg gatgggtggt atcattccca ttctcgggat cgcgaactac     180
gcgcagaagt ttcaaggcag agtaacaatt actgcagacg agtccacctc aaccgcctat    240
atggaactgt cgtcacttcg gtccgaagat acagccgtgt actattgtgc aacgggaggc    300
agcgggaggt atgcccttga catttgggga caggggacaa tggtcacagt aagctccgga    360
ggtgggggat caggaggcgg tggatcgggt gggggaggat cggaaattgt actcactcag    420
tcaccggcga ctctctccct cagcccggga gagcgggcca ccttgtcatg cagagccagc    480
cagagcgtat catcctatct tgcgtggtat cagcaaaaac ccggtcaggc cccaaggttg    540
ctgatctacg atgcgtcgaa tcgcgcgaca ggaatccctg ctaggttctc cgggtcgggc    600
tcggggaccg actttacgct tacgatcagc tcgctggaac cggaggactt cgccgtctac    660
tactgccagc agcggtcgaa ttggccgcct tcctacacat ttggacaagg aacaaagctg    720
gaaatcaaga gagcggaacc gaaatcatgc gacaaaacgc acacctgtcc cccttgtccc    780
gctcccgagt tgctgggagg accgtcggtg ttcctctttc cgccaaaacc caaagatacg    840
ttgatgatct cgcgcacgcc cgaggtgaca tgtgtggtag tcgatgtctc gcacgaggac    900
cccgaagtca agttcaattg gtacgtggac gggtgaag tccataatgc caagacgaaa    960
cctcgggagg agcagtacaa ctccacatat cgcgtagtct cggtgctcac cgtactgcat   1020
caggactggc ttaacggaaa ggaatacaag tgcaaagtgt caacaaggc gttgccggca   1080 ccgattgaga aaacgatctc caaagccaag gggcaacccc gcgagcccca ggtctatact   1140
ctcccgccgt cgcgagatga gctcacgaag aaccaagtct cgcttacgtg cctcgtgaag   1200
ggtttctacc caagcgatat tgcggtggag tgggagagca atggacagcc ggagaacaac   1260
tataagacta ccccacccgt gcttgactcg gatggcagct ctttctgta ctcgaaactg   1320 accgtggaca atcgagatg gcaacagggg aatgtctttt catgttccgt gatgcacgag   1380
gcgctccaca accactacac gcagaagagc ttgtcattga gcccagggaa gaaagaccca   1440
aaggcggccg caattgaagt tatgtatcct cctccttacc tagacaatga gaagagcaat   1500
ggaaccatta tccatgtgaa agggaaacac ctttgtccaa gtccctatt tcccggacct   1560 tctaagccct tttgggtgct ggtggtggtt ggggagtcc tggcttgcta tagcttgcta   1620
gtaacagtgg ccttattatt tttctgggtg aggagtaaga ggagcaggct cctgcacagt   1680
gactacatga acatgactcc ccgccgcccc gggcccaccc gcaagcatta ccagccctat   1740
gccccaccac gcgacttcgc agcctatcgc tccagagtga agttcagcag gagcgcagac   1800
gcccccgcgt accagcaggg ccagaaccag ctctataacg agctcaatct aggacgaaga   1860
```

```
gaggagtacg atgttttgga caagagacgt ggccgggacc ctgagatggg gggaaagccg   1920
agaaggaaga accctcagga aggcctgtac aatgaactgc agaaagataa gatggcggag   1980
gcctacagtg agattgggat gaaaggcgag cgccggaggg gcaaggggca cgatggcctt   2040
taccagggtc tcagtacagc caccaaggac acctacgacg cccttcacat gcaggccctg   2100 cccccctcgct aa                                                      2112
```

<210> SEQ ID NO 52
<211> LENGTH: 2136
<212> TYPE: DNA
<213> ORGANISM: Artificial Sequence
<220> FEATURE:
<223> OTHER INFORMATION: Synthetic

<400> SEQUENCE: 52

```
caagtccagc tgcagcagtc aggagctgag gtgaagaagc ctggtagctc tgtcaaagtg    60
tcttgcaaag cctctggtgg tactttcagc tcttacgcca tttcttgggt gagacaggca   120
cccggacagg gtcttgaatg gatgggtgga atcatcccga ttcttgggat tgctaattac   180
gcacaaaagt tccagggaag ggtgaccatc accgcagacg aatctacctc cactgcttac   240
atggaactct cttccctgcg gtccgaggac accgccgtct actattgtgc caggggcggt   300
gccggaggaa gcggttctta ctatccgctg atttggggac aaggaaccac tgtgaccgtg   360
agctctggtg gaggcggatc cggtggtgga gggtccggag gcggaggatc tgagatcgtg   420
ctcactcaga gcccagccac ccttagcctg agccctggtg agcgcgccac cctctcatgc   480
ggtgcctcac agagcgtgag ctcaagctat ctggcatggt accagcaaaa gccagggcag   540
gccccgaggc tcctgatcta cgacgcatca tcacgggcta ccggtatccc ggcacgcttc   600
tctggaagcg gatcaggcac cgacttcacc ctgaccattt cttccttga gccagaggac   660 tttgccgtgt actactgcca gcagcgctca agctggccgc ctacttggac tttcggacag   720
gggaccaagc tggagatcaa gcgcgctgaa cccaagtcat gcgataagac ccacacttgt   780
ccaccctgtc cagcccctga actgctcgga ggtccgtcag tgtttctttt cccgccaaag   840
cctaaggaca ctctgatgat ctctcggacc cctgaagtga cttgcgtcgt cgtggacgtg   900
tcacacgagg atcccgaggt gaagttcaac tggtatgtgg acggggtgga agtgcataat   960
gctaagacca gcccaggga ggaacaatac aactcaacct accgcgtggt gtccgtgctc   1020 accgtcttc atcaagactg gctgaacgga aaagagtata agtgcaaagt ctccaataag   1080
gctctgccag cccctatcga aaagaccatt tcaaaggcca aggggcagcc tagagagccc   1140
caagtgtaca cccttcctcc ctcaagagat gagctcacta gaatcaggt cagcctgact   1200 tgtcttgtga aaggcttcta tcccagcgat attgccgtcg aatgggaaag caatggacaa   1260
ccagagaaca actacaagac cacccgcct gtgctggact ccgacggctc tttcttcctt   1320
tactcaaagc tgaccgtcga taagagccgg tggcaacagg ggaatgtgtt cagctgctcc   1380
gtcatgcacg aggctctcca taaccactac acccagaaaa gcctgtctct ttctccgggc   1440
aaaaaggacc caaaggcggc cgcaaccacg acgccagcgc cgcgaccacc aacaccggcg   1500
cccaccatcg cgtcgcagcc cctgtccctg cgcccagagg cgtgccggcc agcggcgggg   1560
ggcgcagtgc acacgagggg gctggacttc gcctgtgata tctacatctg ggcgcccttg   1620
gccgggactt gtggggtcct ctcctgtca ctggttatca ccctttactg caaacggggc   1680
agaaagaaac tcctgtatat attcaaacaa ccatttatga gaccagtaca aactactcaa   1740
```

| | |
|---|---:|
| gaggaagatg gctgtagctg ccgatttcca gaagaagaag aaggaggatg tgaactgaga | 1800 |
| gtgaagttca gcaggagcgc agacgccccc gcgtacaagc agggccagaa ccagctctat | 1860 |
| aacgagctca atctaggacg aagagaggag tacgatgttt tggacaagag acgtggccgg | 1920 |
| gaccctgaga tgggggggaaa gccgagaagg aagaaccctc aggaaggcct gtacaatgaa | 1980 |
| ctgcagaaag ataagatggc ggaggcctac agtgagattg ggatgaaagg cgagcgccgg | 2040 |
| aggggcaagg ggcacgatgg cctttaccag ggtctcagta cagccaccaa ggacacctac | 2100 |
| gacgcccttc acatgcaggc cctgccccct cgctaa | 2136 |

<210> SEQ ID NO 53
<211> LENGTH: 2316
<212> TYPE: DNA
<213> ORGANISM: Artificial Sequence
<220> FEATURE:
<223> OTHER INFORMATION: Synthetic

<400> SEQUENCE: 53

| | |
|---|---:|
| caagtccagc tgcagcagtc aggagctgag gtgaagaagc tggtagctc tgtcaaagtg | 60 |
| tcttgcaaag cctctggtgg tactttcagc tcttacgcca tttcttgggt gagacaggca | 120 |
| cccggacagg gtcttgaatg gatgggtgga atcatcccga ttcttgggat tgctaattac | 180 |
| gcacaaaagt tccagggaag ggtgaccatc accgcagacg aatctacctc cactgcttac | 240 |
| atggaactct cttccctgcg gtccgaggac accgccgtct actattgtgc caggggcggt | 300 |
| gccggaggaa gcggttctta ctatccgctg atttgggac aaggaaccac tgtgaccgtg | 360 |
| agctctggtg gaggcggatc cggtggtgga gggtccggag gcggaggatc tgagatcgtg | 420 |
| ctcactcaga gcccagccac ccttagcctg agcctggtg agcgcgccac cctctcatgc | 480 |
| ggtgcctcac agagcgtgag ctcaagctat ctggcatggt accagcaaaa gccagggcag | 540 |
| gccccgaggc tcctgatcta cgacgcatca tcacgggcta ccggtatccc ggcacgcttc | 600 |
| tctggaagcg gatcaggcac cgacttcacc ctgaccattt cttcacttga gccagaggac | 660 |
| tttgccgtgt actactgcca gcagcgctca agctggccgc tacttggac tttcggacag | 720 |
| gggaccaagc tggagatcaa gcgcgctgaa cccaagtcat gcgataagac ccacacttgt | 780 |
| ccaccctgtc cagcccctga actgctcgga ggtccgtcag tgtttctttt cccgccaaag | 840 |
| cctaaggaca ctctgatgat ctctcggacc cctgaagtga cttgcgtcgt cgtggacgtg | 900 |
| tcacacgagg atcccgaggt gaagttcaac tggtatgtgg acggggtgga agtgcataat | 960 |
| gctaagacca gcccaggga ggaacaatac aactcaacct accgcgtggt gtccgtgctc | 1020 |
| accgtcctc atcaagactg gctgaacgga aaagagtata agtgcaaagt ctccaataag | 1080 |
| gctctgccag cccctatcga aaagaccatt tcaaaggcca aggggcagcc tagagagccc | 1140 |
| caagtgtaca cccttcctcc ctcaagagat gagctcacta agaatcaggt cagcctgact | 1200 |
| tgtcttgtga aaggcttcta tcccagcgat attgccgtcg aatgggaaag caatggacaa | 1260 |
| ccagagaaca actacaagac cacccccgcct gtgctgact ccgacggctc tttcttcctt | 1320 |
| tactcaaagc tgaccgtcga taagagccgg tggcaacagg ggaatgtgtt cagctgctcc | 1380 |
| gtcatgcacg aggctctcca taaccactac acccagaaaa gcctgtctct ttctccgggc | 1440 |
| aaaaaggacc caaaggcggc cgcattcgtg ccggtcttcc tgccagcgaa gcccaccacg | 1500 |
| acgccagcgc cgcgaccacc aacaccggcg cccaccatcg cgtcgcagcc cctgtccctg | 1560 |
| cgcccagagg cgtgccggcc agcggcgggg ggcgcagtgc acacgagggg gctgactttc | 1620 |
| gcctgtgata tctacatctg gcgcccttg gccgggactt gtggggtcct tctcctgtca | 1680 |

| | |
|---|---|
| ctggttatca ccctttactg caaccacagg aacaggagta agaggagcag gctcctgcac | 1740 |
| agtgactaca tgaacatgac tccccgccgc cccgggccca cccgcaagca ttaccagccc | 1800 |
| tatgccccac cacgcgactt cgcagcctat cgctcccgtt tctctgttgt taaacggggc | 1860 |
| agaaagaagc tcctgtatat attcaaacaa ccatttatga gaccagtaca aactactcaa | 1920 |
| gaggaagatg gctgtagctg ccgatttcca gaagaagaag aaggaggatg tgaactgaga | 1980 |
| gtgaagttca gcaggagcgc agacgccccc gcgtaccagc agggccagaa ccagctctat | 2040 |
| aacgagctca atctaggacg aagagaggag tacgatgttt tggacaagag acgtggccgg | 2100 |
| gaccctgaga tggggggaaa gccgagaagg aagaaccctc aggaaggcct gtacaatgaa | 2160 |
| ctgcagaaag ataagatggc ggaggcctac agtgagattg ggatgaaagg cgagcgccgg | 2220 |
| aggggcaagg ggcacgatgg cctttaccag ggtctcagta cagccaccaa ggacacctac | 2280 |
| gacgcccttc acatgcaggc cctgccccct cgctaa | 2316 |

<210> SEQ ID NO 54
<211> LENGTH: 2106
<212> TYPE: DNA
<213> ORGANISM: Artificial Sequence
<220> FEATURE:
<223> OTHER INFORMATION: Synthetic

<400> SEQUENCE: 54

| | |
|---|---|
| caagtccagc tggtgcaaag cggagcagaa gtgaagaagc ctggatcctc tgtgaaggtc | 60 |
| agctgcaagg cctctggagg taccttcagc tcttacgcaa tttcttgggt gcgccaggct | 120 |
| cccgggcagg gactggagtg gatgggagga atcatcccga tccttggtac cgctaattac | 180 |
| gcccagaaat tcagggtcg ggtgaccatc accgcagacg agtcaacctc aaccgcttac | 240 |
| atggaacttt ctagcctccg cagcgaggac accgccgtct actattgcgc aagatggggt | 300 |
| ggtggtgcct tcgacatttg gggacagggc actatggtca ccgtgagctc cggtggagga | 360 |
| ggatctggcg gagagggtc aggcggaggt gggtcagaga ttgtgctgac ccagtcaccc | 420 |
| gggactctgt ccctttctcc tggtgagcgc gctactctgt cttgtagggc ctcacaatca | 480 |
| gtgggcggct atctcgcctg gtatcagcag aaaccagggc aggcccctag gcttctcatc | 540 |
| tacgacgcct ccaaccgggc aactggcatt ccagcccgct tcagcggaag cggatccgga | 600 |
| accgactta ctctgactat ctcctcactg gaaccgagg acttcgcagt gtactactgc | 660 |
| cagcagcgga taactggcc accgatgtac actttcggac aggggaccaa gctggagatc | 720 |
| aagcgcgctg aacccaagtc atgcgataag acccacactt gtccaccctg tccagcccct | 780 |
| gaactgctcg gaggtccgtc agtgtttctt ttcccgccaa agcctaagga cactctgatg | 840 |
| atctctcgga cccctgaagt gacttgcgtc gtcgtggacg tgtcacacga ggatcccgag | 900 |
| gtgaagttca actggtatgt ggacggggtg gaagtgcata atgctaagac caagcccagg | 960 |
| gaggaacaat acaactcaac ctaccgcgtg gtgtccgtgc tcaccgtcct tcatcaagac | 1020 |
| tggctgaacg gaaaagagta taagtgcaaa gtctccaata aggctctgcc agcccctatc | 1080 |
| gaaaagacca tttcaaaggc caaggggcag cctagagagc cccaagtgta caccttcct | 1140 |
| ccctcaagag atgagctcac taagaatcag gtcagcctga cttgtcttgt gaaaggcttc | 1200 |
| tatcccagcg atattgccgt cgaatgggaa agcaatggac aaccagagaa caactacaag | 1260 |
| accaccccgc ctgtgctgga ctccgacggc tcttttcttcc tttactcaaa gctgaccgtc | 1320 |
| gataagagcc ggtggcaaca ggggaatgtg ttcagctgct ccgtcatgca cgaggctctc | 1380 |

| | |
|---|---|
| cataaccact acacccagaa aagcctgtct ctttctccgg gcaaaaagga cccaaaggcg | 1440 |
| gccgcaattg aagttatgta tcctcctcct tacctagaca atgagaagag caatggaacc | 1500 |
| attatccatg tgaaagggaa acacctttgt ccaagtcccc tatttcccgg accttctaag | 1560 |
| ccctttgggg tgctggtggt ggttggggga gtcctggctt gctatagctt gctagtaaca | 1620 |
| gtggccttta ttattttctg ggtgaggagt aagaggagca ggctcctgca cagtgactac | 1680 |
| atgaacatga ctccccgccg ccccgggccc accgcaagc attaccagcc ctatgcccca | 1740 |
| ccacgcgact tcgcagccta tcgctccaga gtgaagttca gcaggagcgc agacgccccc | 1800 |
| gcgtaccagc agggccagaa ccagctctat aacgagctca atctaggacg aagagaggag | 1860 |
| tacgatgttt tggacaagag acgtggccgg gaccctgaga tgggggggaaa gccgagaagg | 1920 |
| aagaaccctc aggaaggcct gtacaatgaa ctgcagaaag ataagatggc ggaggcctac | 1980 |
| agtgagattg ggatgaaagg cgagcgccgg aggggcaagg ggcacgatgg cctttaccag | 2040 |
| ggtctcagta cagccaccaa ggacacctac gacgcccttc acatgcaggc cctgccccct | 2100 |
| cgctaa | 2106 |

<210> SEQ ID NO 55
<211> LENGTH: 2118
<212> TYPE: DNA
<213> ORGANISM: Artificial Sequence
<220> FEATURE:
<223> OTHER INFORMATION: Synthetic

<400> SEQUENCE: 55

| | |
|---|---|
| caagtccagc tggtgcaaag cggagcagaa gtgaagaagc ctggatcctc tgtgaaggtc | 60 |
| agctgcaagg cctctggagg taccttcagc tcttacgcaa tttcttgggt gcgccaggct | 120 |
| cccgggcagg gactggagtg gatgggagga atcatcccga tccttggtac cgctaattac | 180 |
| gcccagaaat tcagggtcg ggtgaccatc accgcagacg agtcaacctc aaccgcttac | 240 |
| atggaacttt ctagcctccg cagcgaggac accgccgtct actattgcgc aagatggggt | 300 |
| ggtggtgcct tcgacatttg gggacagggc actatggtca ccgtgagctc cggtggagga | 360 |
| ggatctggcg gaggagggtc aggcggaggt gggtcagaga ttgtgctgac ccagtcaccc | 420 |
| gggactctgt ccctttctcc tggtgagcgc gctactctgt cttgtagggc ctcacaatca | 480 |
| gtgggcggct atctcgcctg gtatcagcag aaaccaggc aggcccctag gcttctcatc | 540 |
| tacgacgcct ccaaccgggc aactggcatt ccagcccgct tcagcggaag cggatccgga | 600 |
| accgactttac tctgactat ctcctcactg gaaccgagg acttcgcagt gtactactgc | 660 |
| cagcagcgga ataactggcc accgatgtac actttcggac aggggaccaa gctggagatc | 720 |
| aagcgcgctg aacccaagtc atgcgataag cccacactt gtccaccctg tccagcccct | 780 |
| gaactgctcg gaggtccgtc agtgtttctt ttcccgccaa agcctaagga cactctgatg | 840 |
| atctctcgga cccctgaagt gacttgcgtc gtcgtggacg tgtcacacga ggatcccgag | 900 |
| gtgaagttca ctggtatgt ggacggggtg gaagtgcata atgctaagac caagcccagg | 960 |
| gaggaacaat acaactcaac ctaccgcgtg gtgtccgtgc tcaccgtcct tcatcaagac | 1020 |
| tggctgaacg gaaagagta taagtgcaaa gtctccaata aggctctgcc agcccctatc | 1080 |
| gaaaagacca tttcaaggc caaggggcag cctagagagc ccaagtgta cacccttcct | 1140 |
| ccctcaagag atgagctcac taagaatcag gtcagcctga cttgtcttgt gaaaggcttc | 1200 |
| tatcccagcg atattgccgt cgaatgggaa agcaatggac aaccagagaa caactacaag | 1260 |
| accaccccgc ctgtgctgga ctccgacggc tctttcttcc tttactcaaa gctgaccgtc | 1320 |

```
gataagagcc ggtggcaaca ggggaatgtg ttcagctgct ccgtcatgca cgaggctctc    1380
cataaccact acacccagaa aagcctgtct ctttctccgg gcaaaaagga cccaaaggcg    1440
gccgcaacca cgacgccagc gccgcgacca ccaacaccgg cgcccaccat cgcgtcgcag    1500
cccctgtccc tgcgcccaga ggcgtgccgg ccagcggcgg ggggcgcagt gcacacgagg    1560
gggctggact tcgcctgtga tatctacatc tgggcgccct tggccgggac ttgtggggtc    1620
cttctcctgt cactggttat cacccttac tgcaaacggg gcagaaagaa actcctgtat    1680
atattcaaac aaccatttat gagaccagta caaactactc aagaggaaga tggctgtagc    1740
tgccgatttc cagaagaaga agaaggagga tgtgaactga gagtgaagtt cagcaggagc    1800
gcagacgccc ccgcgtacaa gcagggccag aaccagctct ataacgagct caatctagga    1860
cgaagagagg agtacgatgt tttggacaag agacgtggcc gggaccctga gatgggggga    1920
aagccgagaa ggaagaaccc tcaggaaggc ctgtacaatg aactgcagaa agataagatg    1980
gcggaggcct acagtgagat tgggatgaaa ggcgagcgcc ggaggggcaa ggggcacgat    2040
ggcctttacc agggtctcag tacagccacc aaggacacct cgacgccct tcacatgcag    2100 gccctgcccc ctcgctaa                                                 2118
```

<210> SEQ ID NO 56
<211> LENGTH: 2298
<212> TYPE: DNA
<213> ORGANISM: Artificial Sequence
<220> FEATURE:
<223> OTHER INFORMATION: Synthetic

<400> SEQUENCE: 56

```
caagtccagc tggtgcaaag cggagcagaa gtgaagaagc ctggatcctc tgtgaaggtc      60
agctgcaagg cctctggagg taccttcagc tcttacgcaa tttcttgggt gcgccaggct     120
cccgggcagg gactgagtg gatgggagga atcatcccga tccttggtac cgctaattac     180
gcccagaaat tcagggtcg ggtgaccatc accgcagacg agtcaacctc aaccgcttac     240
atggaacttt ctagcctccg cagcgaggac accgccgtct actattgcgc aagatggggt     300
ggtggtgcct tcgacatttg gggacagggc actatggtca ccgtgagctc cggtggagga     360
ggatctggcg gaggagggtc aggcggaggt gggtcagaga ttgtgctgac ccagtcaccc     420
gggactctgt cccttctctcc tggtgagcgc gctactctgt cttgtagggc ctcacaatca     480
gtgggcggct atctcgcctg gtatcagcag aaaccagggc aggcccctag gcttctcatc     540
tacgacgcct ccaaccgggc aactggcatt ccagcccgct tcagcggaag cggatccgga     600 accgactta ctctgactat ctcctcactg gaaccggagg acttcgcagt gtactactgc     660
cagcagcgga taactggcc accgatgtac actttcggac aggggaccaa gctggagatc     720
aagcgcgctg aacccaagtc atgcgataag acccacactt gtccaccctg tccagcccct     780
gaactgctcg gaggtccgtc agtgtttctt ttcccgccaa agcctaagga cactctgatg     840
atctctcgga ccccctgaagt gacttgcgtc gtcgtggacg tgtcacacga ggatcccgag     900
gtgaagttca actggtatgt ggacggggtg gaagtgcata atgctaagac caagcccagg     960
gaggaacaat acaactcaac ctaccgcgtg gtgtccgtgc tcaccgtcct tcatcaagac    1020
tggctgaacg gaaagagta taagtgcaaa gtctccaata aggctctgcc agcccctatc    1080
gaaaagacca tttcaaaggc caaggggcag cctagagagc ccaagtgta cacccttcct    1140 ccctcaagag atgagctcac taagaatcag gtcagcctga cttgtcttgt gaaaggcttc    1200
```

```
tatcccagcg atattgccgt cgaatgggaa agcaatggac aaccagagaa caactacaag    1260
accaccccgc ctgtgctgga ctccgacggc tctttcttcc tttactcaaa gctgaccgtc    1320
gataagagcc ggtggcaaca ggggaatgtg ttcagctgct ccgtcatgca cgaggctctc    1380
cataaccact acacccagaa aagcctgtct ctttctccgg gcaaaaagga cccaaaggcg    1440
gccgcattcg tgccggtctt cctgccagcg aagcccacca cgacgccagc gccgcgacca    1500
ccaacaccgg cgcccaccat cgcgtcgcag cccctgtccc tgcgcccaga ggcgtgccgg    1560
ccagcggcgg ggggcgcagt gcacacgagg gggctggact cgcctgtga tatctacatc     1620 tgggcgccct tggccgggac ttgtggggtc cttctcctgt cactggttat caccctttac    1680
tgcaaccaca ggaacaggag taaggaggag caggctcctgc acagtgacta catgaacatg    1740
actccccgcc gccccgggcc caccgcaag cattaccagc cctatgcccc accacgcgac     1800
ttcgcagcct atcgctcccg tttctctgtt gttaaacggg gcagaaagaa gctcctgtat    1860
atattcaaac aaccatttat gagaccagta caaactactc aagaggaaga tggctgtagc    1920
tgccgatttc cagaagaaga agaaggagga tgtgaactga gagtgaagtt cagcaggagc    1980
gcagacgccc ccgcgtacca gcagggccag aaccagctct ataacgagct caatctagga    2040
cgaagagagg agtacgatgt tttgacaag agacgtggcc gggaccctga gatgggggga    2100
aagccgagaa ggaagaaccc tcaggaaggc ctgtacaatg aactgcagaa agataagatg    2160
gcggaggcct acagtgagat tgggatgaaa ggcgagcgcc ggaggggcaa ggggcacgat    2220
ggcctttacc agggtctcag tacagccacc aaggacacct cgacgcccct tcacatgcag    2280
gccctgcccc ctcgctaa                                                  2298

<210> SEQ ID NO 57
<211> LENGTH: 744
<212> TYPE: DNA
<213> ORGANISM: Artificial Sequence
<220> FEATURE:
<223> OTHER INFORMATION: Synthetic

<400> SEQUENCE: 57
caggtacagc tgcagcagtc aggggctgag gtgaagaagc ctggatcctc agtgaaggtc      60
tcctgcaagg cttctggagg caccttcagc agctatgcta tcagctgggt gcgacaggcc     120
cctggacaag gcttgagtg gatgggaggg atcatcccta tccttggtat agcaaactac     180
gcacagaagt tccagggcag agtcacgatt accgcggacg aatccacgag cacagcctac     240
atggagctga gcagcctgag atctgaggac acggccgtgt attactgtgc gagaggaggg     300
gcgggcggtt cggggagtta ttatccccte atctggggcc aagggaccac ggtcaccgtc     360
tcctcaggag gtggcgggtc tggtggaggc ggtagcggtg gtggcggatc cgaaattgtg     420
ttgacgcagt ctccagccac cctgtctttg tctccagggg aaagagccac cctctcctgc     480
ggggccagtc agagtgttag cagcagctac ttagcctggt accagcagaa acctggccag     540
gctcccaggc tcctcatcta tgatgcatcc agcagggcca ctggcatccc ggccaggttc     600
agtggcagtg ggtctgggac agacttcact ctcaccatca gcagcctaga gcctgaagat     660
tttgcagttt attactgtca gcagcgtagt agctggcctc ccacgtggac gttcggccaa     720
gggaccaagc tggaaatcaa acgt                                            744

<210> SEQ ID NO 58
<211> LENGTH: 732
<212> TYPE: DNA
<213> ORGANISM: Artificial Sequence
```

<220> FEATURE:
<223> OTHER INFORMATION: Synthetic

<400> SEQUENCE: 58

```
caggtacagc tgcagcagtc aggggctgag gtgaagaagc ctgggtcctc ggtgaaggtc      60
tcttgcaagg cttctggagg caccttcagc agctatgcta tcagctgggt gcgacaggcc     120
cctggacaag ggctcgagtg gatgggaggg atcatcccta tccttggtat agcaaactac     180
gcacagaagt tccagggcag agtcacgatt accgcggacg aatccacgag cacagcctac     240
atggagctga gcagcctgag atctgaggac acggccgtgt attactgtgc aacaggtggt     300
tcggggagat atgctttgga tatctggggc caagggacaa tggtcaccgt ctcttcagga     360
ggtggcgggt ctggtggagg cggtagcggt ggtggcggat ccgaaattgt gttgacgcag     420
tctccagcca ccctgtcctt gtctccaggg gaaagagcca cctctcctg caggccagt      480
cagagtgtta gcagctactt agcctggtac aacagaaac ctggccaggc tcccaggctc     540
ctcatctatg atgcatccaa cagggccact ggcatcccag ccaggttcag tggcagtggg     600
tctgggacag acttcactct caccatcagc agcctagagc ctgaagattt tgcagtttat     660
tactgtcagc agcgtagcaa ctggcctccg tcgtacactt ttggccaggg gaccaagctg     720
gagatcaaac gt                                                         732
```

<210> SEQ ID NO 59
<211> LENGTH: 726
<212> TYPE: DNA
<213> ORGANISM: Artificial Sequence
<220> FEATURE:
<223> OTHER INFORMATION: Synthetic

<400> SEQUENCE: 59

```
caggtgcagc tggtgcaatc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tccttggtac agcaaactac     180
gcacagaagt tccagggcag agtcacgatt accgcggacg aatccacgag cacagcctac     240
atggagctga gcagcctgag atctgaggac acggccgtgt attactgtgc gagatggggt     300
gggggagctt ttgatatctg gggccaaggg acaatggtca ccgtctcttc aggaggtggc     360
gggtctggtg gaggcggtag cggtggtggc ggatccgaaa ttgtgttgac gcagtctcca     420
ggcaccctgt ctttgtctcc aggggaaaga gccaccctct cctgcagggc cagtcagagt     480
gttgggggct acttagcctg gtaccaacag aaacctggcc aggctcccag gctcctcatc     540
tatgatgcat ccaacagggc caccggcatc ccagccaggt tcagtggcag tgggtctggg     600
acagacttca ctctcaccat cagcagccta gagcctgaag attttgcagt ttattactgt     660
cagcagcgta caactggcc tccgatgtac acttttggcc aggggaccaa gctggaaatc     720
aaacgt                                                                726
```

<210> SEQ ID NO 60
<211> LENGTH: 21
<212> TYPE: PRT
<213> ORGANISM: Artificial Sequence
<220> FEATURE:
<223> OTHER INFORMATION: Synthetic

<400> SEQUENCE: 60

```
Leu Leu Leu Val Thr Ser Leu Leu Leu Cys Glu Leu Pro His Pro Ala
1               5                   10                  15
```

Phe Leu Leu Ile Pro
            20

<210> SEQ ID NO 61
<211> LENGTH: 22
<212> TYPE: PRT
<213> ORGANISM: Artificial Sequence
<220> FEATURE:
<223> OTHER INFORMATION: Synthetic

<400> SEQUENCE: 61

Leu Leu Val Thr Ser Leu Leu Leu Cys Glu Leu Pro His Pro Ala Phe
1               5                   10                  15

Leu Leu Ile Pro Asp Thr
            20

<210> SEQ ID NO 62
<211> LENGTH: 24
<212> TYPE: PRT
<213> ORGANISM: Artificial Sequence
<220> FEATURE:
<223> OTHER INFORMATION: Synthetic

<400> SEQUENCE: 62

Met Val Leu Leu Val Thr Ser Leu Leu Leu Cys Glu Leu Pro His Pro
1               5                   10                  15

Ala Phe Leu Leu Ile Pro Asp Thr
            20

<210> SEQ ID NO 63
<211> LENGTH: 72
<212> TYPE: DNA
<213> ORGANISM: Artificial Sequence
<220> FEATURE:
<223> OTHER INFORMATION: Synthetic

<400> SEQUENCE: 63
atggttttgc tggtgacatc gcttctgttg tgcgaattgc ccatcccgc attcctcctt      60 atccccgata cg                                                         72

<210> SEQ ID NO 64
<211> LENGTH: 72
<212> TYPE: DNA
<213> ORGANISM: Artificial Sequence
<220> FEATURE:
<223> OTHER INFORMATION: Synthetic

<400> SEQUENCE: 64
atggttctgc tggtgacttc actcctgctc tgtgaacttc ccatcccgc ttttctcctg      60 atccccgaca cc                                                         72

<210> SEQ ID NO 65
<211> LENGTH: 16
<212> TYPE: DNA
<213> ORGANISM: Artificial Sequence
<220> FEATURE:
<223> OTHER INFORMATION: Synthetic

<400> SEQUENCE: 65
ccctcgagcc gccacc                                                     16

<210> SEQ ID NO 66
<211> LENGTH: 9

-continued

```
<212> TYPE: DNA
<213> ORGANISM: Artificial Sequence
<220> FEATURE:
<223> OTHER INFORMATION: Synthetic

<400> SEQUENCE: 66 gcggccgca                                                              9

<210> SEQ ID NO 67
<211> LENGTH: 6
<212> TYPE: DNA
<213> ORGANISM: Artificial Sequence
<220> FEATURE:
<223> OTHER INFORMATION: Synthetic

<400> SEQUENCE: 67 ggatcc                                                                 6

<210> SEQ ID NO 68
<211> LENGTH: 8
<212> TYPE: DNA
<213> ORGANISM: Artificial Sequence
<220> FEATURE:
<223> OTHER INFORMATION: Synthetic

<400> SEQUENCE: 68 gcggccgc                                                               8

<210> SEQ ID NO 69
<211> LENGTH: 22
<212> TYPE: DNA
<213> ORGANISM: Artificial Sequence
<220> FEATURE:
<223> OTHER INFORMATION: Synthetic

<400> SEQUENCE: 69
ccctcgagcc gccaccatgg tt                                              22

<210> SEQ ID NO 70
<211> LENGTH: 21
<212> TYPE: DNA
<213> ORGANISM: Artificial Sequence
<220> FEATURE:
<223> OTHER INFORMATION: Synthetic

<400> SEQUENCE: 70
gcggccgcaa ttgaaggcgc g                                               21

<210> SEQ ID NO 71
<211> LENGTH: 237
<212> TYPE: PRT
<213> ORGANISM: Artificial Sequence
<220> FEATURE:
<223> OTHER INFORMATION: Synthetic

<400> SEQUENCE: 71
```

Ala Glu Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

```
Val Asp Gly Val Glu Val His Asn Ala Lys Thr Lys Pro Arg Glu Glu
 65                  70                  75                  80

Gln Tyr Asn Ser Thr Tyr Arg Val Val Ser Val Leu Thr Val Leu His
                 85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Lys Asp Pro Lys
225                 230                 235
```

<210> SEQ ID NO 72
<211> LENGTH: 711
<212> TYPE: DNA
<213> ORGANISM: Artificial Sequence
<220> FEATURE:
<223> OTHER INFORMATION: Synthetic

<400> SEQUENCE: 72

```
gctgaaccca agtcatgcga taagacccac acttgtccac cctgtccagc ccctgaactg    60
ctcggaggtc cgtcagtgtt tctttccccg ccaaagccta aggacactct gatgatctct   120
cggaccctg aagtgacttg cgtcgtcgtg acgtgtcac acgaggatcc cgaggtgaag    180
ttcaactggt atgtggacgg ggtggaagtg cataatgcta agaccaagcc cagggaggaa    240
caatacaact caacctaccg cgtggtgtcc gtgctcaccg tccttcatca agactggctg    300
aacggaaaag agtataagtg caaagtctcc aataaggctc tgccagcccc tatcgaaaag    360
accatttcaa aggccaaggg gcagcctaga gagccccaag tgtacaccct tcctccctca    420
agagatgagc tcactaagaa tcaggtcagc ctgacttgtc ttgtgaaagg cttctatccc    480
agcgatattg ccgtcgaatg ggaaagcaat ggacaaccag agaacaacta caagaccacc    540
ccgcctgtgc tggactccga cggctctttc ttcctttact caaagctgac cgtcgataag    600
agccggtggc aacaggggaa tgtgttcagc tgctccgtca tgcacgaggc tctccataac    660
cactacaccc agaaaagcct gtctctttct ccgggcaaaa aggacccaaa g             711
```

<210> SEQ ID NO 73
<211> LENGTH: 219
<212> TYPE: PRT
<213> ORGANISM: Artificial Sequence
<220> FEATURE:
<223> OTHER INFORMATION: Synthetic

<400> SEQUENCE: 73

```
Ile Glu Val Met Tyr Pro Pro Pro Tyr Leu Asp Asn Glu Lys Ser Asn
 1               5                  10                  15
```

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Gly Gly
        35                  40                  45

Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser Arg Val Lys Phe Ser
            100                 105                 110

Arg Ser Ala Asp Ala Pro Ala Tyr Gln Gln Gly Gln Asn Gln Leu Tyr
        115                 120                 125

Asn Glu Leu Asn Leu Gly Arg Arg Glu Glu Tyr Asp Val Leu Asp Lys
130                 135                 140

Arg Arg Gly Arg Asp Pro Glu Met Gly Gly Lys Pro Arg Arg Lys Asn
145                 150                 155                 160

Pro Gln Glu Gly Leu Tyr Asn Glu Leu Gln Lys Asp Lys Met Ala Glu
                165                 170                 175

Ala Tyr Ser Glu Ile Gly Met Lys Gly Glu Arg Arg Arg Gly Lys Gly
            180                 185                 190

His Asp Gly Leu Tyr Gln Gly Leu Ser Thr Ala Thr Lys Asp Thr Tyr
        195                 200                 205

Asp Ala Leu His Met Gln Ala Leu Pro Pro Arg
    210                 215

<210> SEQ ID NO 74
<211> LENGTH: 223
<212> TYPE: PRT
<213> ORGANISM: Artificial Sequence
<220> FEATURE:
<223> OTHER INFORMATION: Synthetic

<400> SEQUENCE: 74

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys Lys Arg Gly Arg Lys Lys Leu Leu Tyr Ile Phe
65                  70                  75                  80

Lys Gln Pro Phe Met Arg Pro Val Gln Thr Thr Gln Glu Glu Asp Gly
                85                  90                  95

Cys Ser Cys Arg Phe Pro Glu Glu Glu Glu Gly Gly Cys Glu Leu Arg
            100                 105                 110

Val Lys Phe Ser Arg Ser Ala Asp Ala Pro Ala Tyr Lys Gln Gly Gln
        115                 120                 125

Asn Gln Leu Tyr Asn Glu Leu Asn Leu Gly Arg Arg Glu Glu Tyr Asp
130                 135                 140

Val Leu Asp Lys Arg Arg Gly Arg Asp Pro Glu Met Gly Gly Lys Pro
145                 150                 155                 160

```
Arg Arg Lys Asn Pro Gln Glu Gly Leu Tyr Asn Glu Leu Gln Lys Asp
            165                 170                 175

Lys Met Ala Glu Ala Tyr Ser Glu Ile Gly Met Lys Gly Glu Arg Arg
        180                 185                 190

Arg Gly Lys Gly His Asp Gly Leu Tyr Gln Gly Leu Ser Thr Ala Thr
    195                 200                 205

Lys Asp Thr Tyr Asp Ala Leu His Met Gln Ala Leu Pro Pro Arg
    210                 215                 220

<210> SEQ ID NO 75
<211> LENGTH: 283
<212> TYPE: PRT
<213> ORGANISM: Artificial Sequence
<220> FEATURE:
<223> OTHER INFORMATION: Synthetic

<400> SEQUENCE: 75

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn Arg Ser Lys Arg Ser Arg Leu Leu His Ser Asp Tyr Met
                85                  90                  95

Asn Met Thr Pro Arg Arg Pro Gly Pro Thr Arg Lys His Tyr Gln Pro
            100                 105                 110

Tyr Ala Pro Pro Arg Asp Phe Ala Ala Tyr Arg Ser Arg Phe Ser Val
        115                 120                 125

Val Lys Arg Gly Arg Lys Lys Leu Leu Tyr Ile Phe Lys Gln Pro Phe
    130                 135                 140

Met Arg Pro Val Gln Thr Thr Gln Glu Glu Asp Gly Cys Ser Cys Arg
145                 150                 155                 160

Phe Pro Glu Glu Glu Glu Gly Gly Cys Glu Leu Arg Val Lys Phe Ser
                165                 170                 175

Arg Ser Ala Asp Ala Pro Ala Tyr Gln Gln Gly Gln Asn Gln Leu Tyr
            180                 185                 190

Asn Glu Leu Asn Leu Gly Arg Arg Glu Glu Tyr Asp Val Leu Asp Lys
        195                 200                 205

Arg Arg Gly Arg Asp Pro Glu Met Gly Gly Lys Pro Arg Arg Lys Asn
    210                 215                 220

Pro Gln Glu Gly Leu Tyr Asn Glu Leu Gln Lys Asp Lys Met Ala Glu
225                 230                 235                 240

Ala Tyr Ser Glu Ile Gly Met Lys Gly Glu Arg Arg Arg Gly Lys Gly
                245                 250                 255

His Asp Gly Leu Tyr Gln Gly Leu Ser Thr Ala Thr Lys Asp Thr Tyr
            260                 265                 270

Asp Ala Leu His Met Gln Ala Leu Pro Pro Arg
        275                 280

<210> SEQ ID NO 76
```

<211> LENGTH: 657
<212> TYPE: DNA
<213> ORGANISM: Artificial Sequence
<220> FEATURE:
<223> OTHER INFORMATION: Synthetic

<400> SEQUENCE: 76

| | | | | | |
|---|---|---|---|---|---|
| attgaagtta | tgtatcctcc | tccttaccta | gacaatgaga | agagcaatgg | aaccattatc | 60 |
| catgtgaaag | ggaaacacct | ttgtccaagt | cccctatttc | ccggaccttc | taagcccttt | 120 |
| tgggtgctgg | tggtggttgg | gggagtcctg | gcttgctata | gcttgctagt | aacagtggcc | 180 |
| tttattattt | tctgggtgag | gagtaagagg | agcaggctcc | tgcacagtga | ctacatgaac | 240 |
| atgactcccc | gccgccccgg | gcccacccgc | aagcattacc | agccctatgc | ccaccacgc | 300 |
| gacttcgcag | cctatcgctc | cagagtgaag | ttcagcagga | gcgcagacgc | cccgcgtac | 360 |
| cagcagggcc | agaaccagct | ctataacgag | ctcaatctag | gacgaagaga | ggagtacgat | 420 |
| gttttggaca | agagacgtgg | ccgggaccct | gagatggggg | gaaagccgag | aaggaagaac | 480 |
| cctcaggaag | gcctgtacaa | tgaactgcag | aaagataaga | tggcggaggc | ctacagtgag | 540 |
| attgggatga | aggcgagcg | ccggaggggc | aaggggcacg | atggccttta | ccagggtctc | 600 |
| agtacagcca | ccaaggacac | ctacgacgcc | cttcacatgc | aggccctgcc | ccctcgc | 657 |

<210> SEQ ID NO 77
<211> LENGTH: 669
<212> TYPE: DNA
<213> ORGANISM: Artificial Sequence
<220> FEATURE:
<223> OTHER INFORMATION: Synthetic

<400> SEQUENCE: 77

| | | | | | |
|---|---|---|---|---|---|
| accacgacgc | cagcgccgcg | accaccaaca | ccggcgccca | ccatcgcgtc | gcagcccctg | 60 |
| tccctgcgcc | cagaggcgtg | ccggccagcg | gcggggggcg | cagtgcacac | gaggggctg | 120 |
| gacttcgcct | gtgatatcta | catctgggcg | cccttggccg | ggacttgtgg | ggtccttctc | 180 |
| ctgtcactgg | ttatcaccct | ttactgcaaa | cggggcagaa | agaaactcct | gtatatattc | 240 |
| aaacaaccat | ttatgagacc | agtacaaact | actcaagagg | aagatggctg | tagctgccga | 300 |
| tttccagaag | aagaagaagg | aggatgtgaa | ctgagagtga | agttcagcag | gagcgcagac | 360 |
| gccccgcgt | acaagcaggg | ccagaaccag | ctctataacg | agctcaatct | aggacgaaga | 420 |
| gaggagtacg | atgttttgga | caagagacgt | ggccgggacc | ctgagatggg | gggaaagccg | 480 |
| agaaggaaga | accctcagga | aggcctgtac | aatgaactgc | agaaagataa | gatggcggag | 540 |
| gcctacagtg | agattgggat | gaaaggcgag | cgccggaggg | gcaaggggca | cgatggcctt | 600 |
| taccagggtc | tcagtacagc | caccaaggac | acctacgacg | cccttcacat | gcaggccctg | 660 |
| cccctcgc | | | | | | 669 |

<210> SEQ ID NO 78
<211> LENGTH: 849
<212> TYPE: DNA
<213> ORGANISM: Artificial Sequence
<220> FEATURE:
<223> OTHER INFORMATION: Synthetic

<400> SEQUENCE: 78

| | | | | | |
|---|---|---|---|---|---|
| ttcgtgccgg | tcttcctgcc | agcgaagccc | accacgacgc | cagcgccgcg | accaccaaca | 60 |
| ccggcgccca | ccatcgcgtc | gcagcccctg | tccctgcgcc | cagaggcgtg | ccggccagcg | 120 |
| gcggggggcg | cagtgcacac | gaggggctg | gacttcgcct | gtgatatcta | catctgggcg | 180 |

```
cccttggccg ggacttgtgg ggtccttctc ctgtcactgg ttatcaccct ttactgcaac      240
cacaggaaca ggagtaagag gagcaggctc ctgcacagtg actacatgaa catgactccc      300 cgccgcccg ggcccacccg caagcattac cagccctatg ccccaccacg cgacttcgca       360
gcctatcgct cccgtttctc tgttgttaaa cggggcagaa agaagctcct gtatatattc      420
aaacaaccat ttatgagacc agtacaaact actcaagagg aagatggctg tagctgccga      480
tttccagaag aagaagaagg aggatgtgaa ctgagagtga agttcagcag gagcgcagac      540
gcccccgcgt accagcaggg ccagaaccag ctctataacg agctcaatct aggacgaaga      600
gaggagtacg atgttttgga caagagacgt ggccgggacc ctgagatggg gggaaagccg      660
agaaggaaga accctcagga aggcctgtac aatgaactgc agaaagataa gatggcggag      720
gcctacagtg agattgggat gaaaggcgag cgccggaggg gcaaggggca cgatggcctt      780
taccagggtc tcagtacagc caccaaggac acctacgacg cccttcacat gcaggccctg      840
ccccctcgc                                                              849

<210> SEQ ID NO 79
<211> LENGTH: 1521
<212> TYPE: DNA
<213> ORGANISM: Artificial Sequence
<220> FEATURE:
<223> OTHER INFORMATION: Synthetic

<400> SEQUENCE: 79
ctgctggtga cttcactcct gctctgtgaa cttccccatc ccgcttttct cctgatcccc       60
gacacccaag tccagctgca gcagtcagga gctgaggtga agaagcctgg tagctctgtc      120
aaagtgtctt gcaaagcctc tggtggtact ttcagctctt acgccatttc ttgggtgaga      180
caggcacccg gacagggtct tgaatggatg ggtggaatca tcccgattct tgggattgct      240
aattacgcac aaaagttcca gggaagggtg accatcaccg cagacgaatc tacctccact      300
gcttacatgg aactctcttc cctgcggtcc gaggacaccg ccgtctacta ttgtgccagg      360
ggcggtgccg gaggaagcgg ttcttactat ccgctgattt ggggacaagg aaccactgtg      420
accgtgagct ctggtggagg cggatccggt ggtggagggt ccggaggcgg aggatctgag      480
atcgtgctca ctcagagccc agccaccctt agcctgagcc ctggtgagcg cgccacccta      540
tcatgcggtg cctcacagag cgtgagctca agctatctgg catggtacca gcaaaagcca      600
gggcaggccc cgaggctcct gatctacgac gcatcatcac gggctaccgg tatcccggca      660
cgcttctctg gaagcggatc aggcaccgac ttcaccctga ccatttcttc acttgagcca      720
gaggactttg ccgtgtacta ctgccagcag cgctcaagct ggccgcctac ttggactttc      780
ggacagggga ccaagctgga gatcaagcgc gctgaaccca gtcatgcga taagacccac      840 acttgtccac cctgtccagc ccctgaactg ctcggaggtc cgtcagtgtt tcttttcccg      900
ccaaagccta aggacactct gatgatctct cggacccctg aagtgacttg cgtcgtcgtg      960
gacgtgtcac acgaggatcc cgaggtgaag ttcaactggt atgtggacgg ggtggaagtg     1020
cataatgcta agaccaagcc cagggaggaa caatacaact caacctaccg cgtggtgtcc     1080
gtgctcaccg tccttcatca agactggctg aacggaaaag agtataagtg caaagtctcc     1140
aataaggctc tgccagcccc tatcgaaaag accatttcaa aggccaaggg gcagcctaga     1200 gagcccaag tgtacaccct tcctcccctca agagatgagc tcactaagaa tcaggtcagc     1260
ctgacttgtc ttgtgaaagg cttctatccc agcgatattg ccgtcgaatg ggaaagcaat     1320
```

```
ggacaaccag agaacaacta caagaccacc ccgcctgtgc tggactccga cggctctttc    1380
ttcctttact caaagctgac cgtcgataag agccggtggc aacagggaa tgtgttcagc     1440 tgctccgtca tgcacgaggc tctccataac cactacaccc agaaaagcct gtctctttct    1500
ccgggcaaaa aggacccaaa g                                               1521
```

<210> SEQ ID NO 80
<211> LENGTH: 485
<212> TYPE: PRT
<213> ORGANISM: Artificial Sequence
<220> FEATURE:
<223> OTHER INFORMATION: Synthetic

<400> SEQUENCE: 80

```
Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Ala Gly Gly Ser Gly Ser Tyr Tyr Pro Leu Ile Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Ser Glu Ile Val Leu Thr Gln Ser
    130                 135                 140

Pro Ala Thr Leu Ser Leu Ser Pro Gly Glu Arg Ala Thr Leu Ser Cys
145                 150                 155                 160

Gly Ala Ser Gln Ser Val Ser Ser Ser Tyr Leu Ala Trp Tyr Gln Gln
                165                 170                 175

Lys Pro Gly Gln Ala Pro Arg Leu Leu Ile Tyr Asp Ala Ser Ser Arg
            180                 185                 190

Ala Thr Gly Ile Pro Ala Arg Phe Ser Gly Ser Gly Ser Gly Thr Asp
        195                 200                 205

Phe Thr Leu Thr Ile Ser Ser Leu Glu Pro Glu Asp Phe Ala Val Tyr
    210                 215                 220

Tyr Cys Gln Gln Arg Ser Ser Trp Pro Pro Thr Trp Thr Phe Gly Gln
225                 230                 235                 240

Gly Thr Lys Leu Glu Ile Lys Arg Ala Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
```

| | | | | | 325 | | | | | 330 | | | | | 335 | | |
|---|---|---|---|---|---|---|---|---|---|---|---|---|---|---|---|---|---|
| Val | Ser | Val | Leu | Thr | Val | Leu | His | Gln | Asp | Trp | Leu | Asn | Gly | Lys | Glu |

Tyr Lys Cys Lys Val Ser Asn Lys Ala Leu Pro Ala Pro Ile Glu Lys
      355                 360                 365

Thr Ile Ser Lys Ala Lys Gly Gln Pro Arg Glu Pro Gln Val Tyr Thr
370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
                420                 425                 430

Asp Ser Asp Gly Ser Phe Phe Leu Tyr Ser Lys Leu Thr Val Asp Lys
                435                 440                 445

Ser Arg Trp Gln Gln Gly Asn Val Phe Ser Cys Ser Val Met His Glu
450                 455                 460

Ala Leu His Asn His Tyr Thr Gln Lys Ser Leu Ser Leu Ser Pro Gly
465                 470                 475                 480

Lys Lys Asp Pro Lys
            485

```
<210> SEQ ID NO 81
<211> LENGTH: 1509
<212> TYPE: DNA
<213> ORGANISM: Artificial Sequence
<220> FEATURE:
<223> OTHER INFORMATION: Synthetic

<400> SEQUENCE: 81
ttgctggtga catcgcttct gttgtgcgaa ttgccccatc ccgcattcct ccttatcccc      60
gatacgcaag tccaacttca gcagtcaggg gcggaggtga agaagccggg ctcctccgta     120
aaggtgtcgt gcaaagcatc gggcggtaca ttctcctcct atgcgatctc atgggtgcga     180
caggcacccg gcaggggtt ggaatggatg gtggtatca ttcccattct cgggatcgcg      240
aactacgcgc agaagtttca aggcagagta acaattactg cagacgagtc cacctcaacc     300
gcctatatgg aactgtcgtc acttcggtcc gaagatacag ccgtgtacta ttgtgcaacg     360
ggaggcagcg ggaggtatgc ccttgacatt tggggacagg gacaatggt cacagtaagc      420 tccggaggtg ggggatcagg aggcggtgga tcgggtgggg gaggatcgga aattgtactc     480
actcagtcac cggcgactct ctccctcagc ccgggagagc gggccacctt gtcatgcaga     540
gccagccaga gcgtatcatc ctatcttgcg tggtatcagc aaaaacccgg tcaggcccca     600
aggttgctga tctacgatgc gtcgaatcgc gcgacaggaa tccctgctag gttctccggg     660
tcgggctcgg gaccgacttt acgcttacg atcagctcgc tggaaccgga ggacttcgcc      720
gtctactact gccagcagcg gtcgaattgg ccgccttcct acacatttgg acaaggaaca     780
aagctggaaa tcaagagagc ggaaccgaaa tcatgcgaca aaacgcacac ctgtccccct     840
tgtcccgctc ccgagttgct gggaggaccg tcggtgttcc tctttccgcc aaaacccaaa     900
gatacgttga tgatctcgcg cacgcccgag gtgacatgtg tggtagtcga tgtctcgcac     960
gaggaccccg aagtcaagtt caattggtac gtggacgggg tggaagtcca taatgccaag    1020
acgaaacctc gggaggagca gtacaactcc acatatcgcg tagtctcggt gctcaccgta    1080
ctgcatcagg actggcttaa cggaaaggaa tacaagtgca agtgtcaaa caaggcgttg    1140
```

-continued

```
ccggcaccga ttgagaaaac gatctccaaa gccaaggggc aaccccgcga gccccaggtc    1200
tatactctcc cgccgtcgcg agatgagctc acgaagaacc aagtctcgct tacgtgcctc    1260
gtgaagggtt tctacccaag cgatattgcg gtggagtggg agagcaatgg acagccggag    1320
aacaactata agactacccc accgtgctt gactcggatg gcagcttctt tctgtactcg    1380
aaactgaccg tggacaaatc gagatggcaa caggggaatg tcttttcatg ttccgtgatg    1440
cacgaggcgc tccacaacca ctacacgcag aagagcttgt cattgagccc agggaagaaa    1500
gacccaaag                                                            1509
```

<210> SEQ ID NO 82
<211> LENGTH: 481
<212> TYPE: PRT
<213> ORGANISM: Artificial Sequence
<220> FEATURE:
<223> OTHER INFORMATION: Synthetic

<400> SEQUENCE: 82

```
Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Gly Ser Gly Arg Tyr Ala Leu Asp Ile Trp Gly Gln Gly
            100                 105                 110

Thr Met Val Thr Val Ser Ser Gly Gly Gly Ser Gly Gly Gly Gly
        115                 120                 125

Ser Gly Gly Gly Gly Ser Glu Ile Val Leu Thr Gln Ser Pro Ala Thr
    130                 135                 140

Leu Ser Leu Ser Pro Gly Glu Arg Ala Thr Leu Ser Cys Arg Ala Ser
145                 150                 155                 160

Gln Ser Val Ser Ser Tyr Leu Ala Trp Tyr Gln Gln Lys Pro Gly Gln
                165                 170                 175

Ala Pro Arg Leu Leu Ile Tyr Asp Ala Ser Asn Arg Ala Thr Gly Ile
            180                 185                 190

Pro Ala Arg Phe Ser Gly Ser Gly Ser Gly Thr Asp Phe Thr Leu Thr
        195                 200                 205

Ile Ser Ser Leu Glu Pro Glu Asp Phe Ala Val Tyr Tyr Cys Gln Gln
    210                 215                 220

Arg Ser Asn Trp Pro Pro Ser Tyr Thr Phe Gly Gln Gly Thr Lys Leu
225                 230                 235                 240

Glu Ile Lys Arg Ala Glu Pro Lys Ser Cys Asp Lys Thr His Thr Cys
                245                 250                 255

Pro Pro Cys Pro Ala Pro Glu Leu Leu Gly Gly Pro Ser Val Phe Leu
            260                 265                 270

Phe Pro Pro Lys Pro Lys Asp Thr Leu Met Ile Ser Arg Thr Pro Glu
        275                 280                 285
```

```
Val Thr Cys Val Val Asp Val Ser His Glu Asp Pro Glu Val Lys
    290             295                 300
Phe Asn Trp Tyr Val Asp Gly Val Glu Val His Asn Ala Lys Thr Lys
305                 310                 315                 320
Pro Arg Glu Glu Gln Tyr Asn Ser Thr Tyr Arg Val Val Ser Val Leu
                325                 330                 335
Thr Val Leu His Gln Asp Trp Leu Asn Gly Lys Glu Tyr Lys Cys Lys
            340                 345                 350
Val Ser Asn Lys Ala Leu Pro Ala Pro Ile Glu Lys Thr Ile Ser Lys
        355                 360                 365
Ala Lys Gly Gln Pro Arg Glu Pro Gln Val Tyr Thr Leu Pro Pro Ser
370                 375                 380
Arg Asp Glu Leu Thr Lys Asn Gln Val Ser Leu Thr Cys Leu Val Lys
385                 390                 395                 400
Gly Phe Tyr Pro Ser Asp Ile Ala Val Glu Trp Glu Ser Asn Gly Gln
                405                 410                 415
Pro Glu Asn Asn Tyr Lys Thr Thr Pro Pro Val Leu Asp Ser Asp Gly
            420                 425                 430
Ser Phe Phe Leu Tyr Ser Lys Leu Thr Val Asp Lys Ser Arg Trp Gln
        435                 440                 445
Gln Gly Asn Val Phe Ser Cys Ser Val Met His Glu Ala Leu His Asn
450                 455                 460
His Tyr Thr Gln Lys Ser Leu Ser Leu Ser Pro Gly Lys Lys Asp Pro
465                 470                 475                 480
Lys
```

<210> SEQ ID NO 83
<211> LENGTH: 1503
<212> TYPE: DNA
<213> ORGANISM: Artificial Sequence
<220> FEATURE:
<223> OTHER INFORMATION: Synthetic

<400> SEQUENCE: 83

```
ctgctggtga cttcactcct gctctgtgaa cttccccatc ccgcttttct cctgatcccc    60
gacacccaag tccagctggt gcaaagcgga gcagaagtga agaagcctgg atcctctgtg   120
aaggtcagct gcaaggcctc tggaggtacc ttcagctctt acgcaatttc ttgggtgcgc   180
caggctcccg gcagggact ggagtggatg ggaggaatca tcccgatcct ggtaccgct    240
aattacgccc agaaatttca gggtcgggtg accatcaccg cagacgagtc aacctcaacc   300
gcttacatgg aactttctag cctccgcagc gaggacaccg ccgtctacta ttgcgcaaga   360
tggggtggtg gtgccttcga catttgggga caggcactg gtcaccgt gagctccggt    420
ggaggaggat ctggcggagg agggtcaggc ggaggtgggt cagagattgt gctgacccag   480
tcacccggga ctctgtccct ttctcctggt gagcgcgcta ctctgtcttg tagggcctca   540
caatcagtgg gcggctatct cgcctggtat cagcagaaac cagggcaggc ccctaggctt   600
ctcatctacg acgcctccaa ccgggcaact ggcattccag cccgcttcag cggaagcgga   660
tccggaaccg actttactct gactatctcc tcactgaac cggaggactt cgcagtgtac   720
tactgccagc agcggaataa ctggccaccg atgtacactt tcggacaggg gaccaagctg   780
gagatcaagc gcgctgaacc caagtcatgc gataagaccc acacttgtcc accctgtcca   840
gcccctgaac tgctcggagg tccgtcagtg tttcttttcc cgccaaagcc taaggacact   900
ctgatgatct ctcggacccc tgaagtgact tgcgtcgtcg tggacgtgtc acacgaggat   960
```

```
cccgaggtga agttcaactg gtatgtggac ggggtggaag tgcataatgc taagaccaag    1020
cccagggagg aacaatacaa ctcaacctac cgcgtggtgt ccgtgctcac cgtccttcat    1080
caagactggc tgaacggaaa agagtataag tgcaaagtct ccaataaggc tctgccagcc    1140
cctatcgaaa agaccatttc aaaggccaag gggcagccta gagagcccca agtgtacacc    1200
cttcctccct caagagatga gctcactaag aatcaggtca gcctgacttg tcttgtgaaa    1260
ggcttctatc ccagcgatat tgccgtcgaa tgggaaagca atggacaacc agagaacaac    1320
tacaagacca ccccgcctgt gctggactcc gacggctctt tcttccttta ctcaaagctg    1380
accgtcgata gagccggtg gcaacagggg aatgtgttca gctgctccgt catgcacgag     1440
gctctccata accactacac ccagaaaagc ctgtctcttt ctccgggcaa aaaggaccca    1500
aag                                                                 1503
```

<210> SEQ ID NO 84
<211> LENGTH: 479
<212> TYPE: PRT
<213> ORGANISM: Artificial Sequence
<220> FEATURE:
<223> OTHER INFORMATION: Synthetic

<400> SEQUENCE: 84

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Gly Gly Ala Phe Asp Ile Trp Gly Gln Gly Thr Met
            100                 105                 110

Val Thr Val Ser Ser Gly Gly Gly Gly Ser Gly Gly Gly Gly Ser Gly
        115                 120                 125

Gly Gly Gly Ser Glu Ile Val Leu Thr Gln Ser Pro Gly Thr Leu Ser
    130                 135                 140

Leu Ser Pro Gly Glu Arg Ala Thr Leu Ser Cys Arg Ala Ser Gln Ser
145                 150                 155                 160

Val Gly Gly Tyr Leu Ala Trp Tyr Gln Gln Lys Pro Gly Gln Ala Pro
                165                 170                 175

Arg Leu Leu Ile Tyr Asp Ala Ser Asn Arg Ala Thr Gly Ile Pro Ala
            180                 185                 190

Arg Phe Ser Gly Ser Gly Ser Gly Thr Asp Phe Thr Leu Thr Ile Ser
        195                 200                 205

Ser Leu Glu Pro Glu Asp Phe Ala Val Tyr Tyr Cys Gln Gln Arg Asn
    210                 215                 220

Asn Trp Pro Pro Met Tyr Thr Phe Gly Gln Gly Thr Lys Leu Glu Ile
225                 230                 235                 240

Lys Arg Ala Glu Pro Lys Ser Cys Asp Lys Thr His Thr Cys Pro Pro
                245                 250                 255
```

```
Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys Lys Asp Pro Lys
465                 470                 475

<210> SEQ ID NO 85
<211> LENGTH: 4
<212> TYPE: DNA
<213> ORGANISM: Artificial Sequence
<220> FEATURE:
<223> OTHER INFORMATION: Synthetic

<400> SEQUENCE: 85 aaaa                                                            4

<210> SEQ ID NO 86
<211> LENGTH: 4
<212> TYPE: DNA
<213> ORGANISM: Artificial Sequence
<220> FEATURE:
<223> OTHER INFORMATION: Synthetic

<400> SEQUENCE: 86 aaaa                                                            4

<210> SEQ ID NO 87
<211> LENGTH: 4
<212> TYPE: DNA
<213> ORGANISM: Artificial Sequence
<220> FEATURE:
<223> OTHER INFORMATION: Synthetic

<400> SEQUENCE: 87 aaaa                                                            4
```

```
<210> SEQ ID NO 88
<211> LENGTH: 4
<212> TYPE: DNA
<213> ORGANISM: Artificial Sequence
<220> FEATURE:
<223> OTHER INFORMATION: Synthetic

<400> SEQUENCE: 88 aaaa                                                                    4

<210> SEQ ID NO 89
<211> LENGTH: 4
<212> TYPE: DNA
<213> ORGANISM: Artificial Sequence
<220> FEATURE:
<223> OTHER INFORMATION: Synthetic

<400> SEQUENCE: 89 aaaa                                                                    4

<210> SEQ ID NO 90
<211> LENGTH: 4
<212> TYPE: DNA
<213> ORGANISM: Artificial Sequence
<220> FEATURE:
<223> OTHER INFORMATION: Synthetic

<400> SEQUENCE: 90 aaaa                                                                    4

<210> SEQ ID NO 91
<211> LENGTH: 4
<212> TYPE: PRT
<213> ORGANISM: Artificial Sequence
<220> FEATURE:
<223> OTHER INFORMATION: Synthetic

<400> SEQUENCE: 91

Ala Ala Ala Ala
1

<210> SEQ ID NO 92
<211> LENGTH: 4
<212> TYPE: PRT
<213> ORGANISM: Artificial Sequence
<220> FEATURE:
<223> OTHER INFORMATION: Synthetic

<400> SEQUENCE: 92

Ala Ala Ala Ala
1

<210> SEQ ID NO 93
<211> LENGTH: 4
<212> TYPE: PRT
<213> ORGANISM: Artificial Sequence
<220> FEATURE:
<223> OTHER INFORMATION: Synthetic

<400> SEQUENCE: 93

Ala Ala Ala Ala
1

<210> SEQ ID NO 94
<211> LENGTH: 4
<212> TYPE: PRT
<213> ORGANISM: Artificial Sequence
```

```
<220> FEATURE:
<223> OTHER INFORMATION: Synthetic

<400> SEQUENCE: 94

Ala Ala Ala Ala
1

<210> SEQ ID NO 95
<211> LENGTH: 4
<212> TYPE: PRT
<213> ORGANISM: Artificial Sequence
<220> FEATURE:
<223> OTHER INFORMATION: Synthetic

<400> SEQUENCE: 95

Ala Ala Ala Ala
1

<210> SEQ ID NO 96
<211> LENGTH: 4
<212> TYPE: PRT
<213> ORGANISM: Artificial Sequence
<220> FEATURE:
<223> OTHER INFORMATION: Synthetic

<400> SEQUENCE: 96

Ala Ala Ala Ala
1

<210> SEQ ID NO 97
<211> LENGTH: 4
<212> TYPE: PRT
<213> ORGANISM: Artificial Sequence
<220> FEATURE:
<223> OTHER INFORMATION: Synthetic

<400> SEQUENCE: 97

Ala Ala Ala Ala
1

<210> SEQ ID NO 98
<211> LENGTH: 4
<212> TYPE: PRT
<213> ORGANISM: Artificial Sequence
<220> FEATURE:
<223> OTHER INFORMATION: Synthetic

<400> SEQUENCE: 98

Ala Ala Ala Ala
1

<210> SEQ ID NO 99
<211> LENGTH: 4
<212> TYPE: PRT
<213> ORGANISM: Artificial Sequence
<220> FEATURE:
<223> OTHER INFORMATION: Synthetic

<400> SEQUENCE: 99

Ala Ala Ala Ala
1

<210> SEQ ID NO 100
<211> LENGTH: 4
<212> TYPE: PRT
<213> ORGANISM: Artificial Sequence
<220> FEATURE:
```

<223> OTHER INFORMATION: Synthetic

<400> SEQUENCE: 100

Ala Ala Ala Ala
1

<210> SEQ ID NO 101
<211> LENGTH: 4
<212> TYPE: PRT
<213> ORGANISM: Artificial Sequence
<220> FEATURE:
<223> OTHER INFORMATION: Synthetic

<400> SEQUENCE: 101

Ala Ala Ala Ala
1

<210> SEQ ID NO 102
<211> LENGTH: 4
<212> TYPE: PRT
<213> ORGANISM: Artificial Sequence
<220> FEATURE:
<223> OTHER INFORMATION: Synthetic

<400> SEQUENCE: 102

Ala Ala Ala Ala
1

<210> SEQ ID NO 103
<211> LENGTH: 4
<212> TYPE: PRT
<213> ORGANISM: Artificial Sequence
<220> FEATURE:
<223> OTHER INFORMATION: Synthetic

<400> SEQUENCE: 103

Ala Ala Ala Ala
1

<210> SEQ ID NO 104
<211> LENGTH: 4
<212> TYPE: PRT
<213> ORGANISM: Artificial Sequence
<220> FEATURE:
<223> OTHER INFORMATION: Synthetic

<400> SEQUENCE: 104

Ala Ala Ala Ala
1

<210> SEQ ID NO 105
<211> LENGTH: 4
<212> TYPE: PRT
<213> ORGANISM: Artificial Sequence
<220> FEATURE:
<223> OTHER INFORMATION: Synthetic

<400> SEQUENCE: 105

Ala Ala Ala Ala
1

<210> SEQ ID NO 106
<211> LENGTH: 4
<212> TYPE: PRT
<213> ORGANISM: Artificial Sequence
<220> FEATURE:
<223> OTHER INFORMATION: Synthetic

```
<400> SEQUENCE: 106

Ala Ala Ala Ala
1

<210> SEQ ID NO 107
<211> LENGTH: 4
<212> TYPE: PRT
<213> ORGANISM: Artificial Sequence
<220> FEATURE:
<223> OTHER INFORMATION: Synthetic

<400> SEQUENCE: 107

Ala Ala Ala Ala
1

<210> SEQ ID NO 108
<211> LENGTH: 4
<212> TYPE: PRT
<213> ORGANISM: Artificial Sequence
<220> FEATURE:
<223> OTHER INFORMATION: Synthetic

<400> SEQUENCE: 108

Ala Ala Ala Ala
1

<210> SEQ ID NO 109
<211> LENGTH: 4
<212> TYPE: PRT
<213> ORGANISM: Artificial Sequence
<220> FEATURE:
<223> OTHER INFORMATION: Synthetic

<400> SEQUENCE: 109

Ala Ala Ala Ala
1

<210> SEQ ID NO 110
<211> LENGTH: 4
<212> TYPE: PRT
<213> ORGANISM: Artificial Sequence
<220> FEATURE:
<223> OTHER INFORMATION: Synthetic

<400> SEQUENCE: 110

Ala Ala Ala Ala
1

<210> SEQ ID NO 111
<211> LENGTH: 4
<212> TYPE: PRT
<213> ORGANISM: Artificial Sequence
<220> FEATURE:
<223> OTHER INFORMATION: Synthetic

<400> SEQUENCE: 111

Ala Ala Ala Ala
1

<210> SEQ ID NO 112
<211> LENGTH: 4
<212> TYPE: PRT
<213> ORGANISM: Artificial Sequence
<220> FEATURE:
<223> OTHER INFORMATION: Synthetic
```

<400> SEQUENCE: 112

Ala Ala Ala Ala
1

<210> SEQ ID NO 113
<211> LENGTH: 4
<212> TYPE: PRT
<213> ORGANISM: Artificial Sequence
<220> FEATURE:
<223> OTHER INFORMATION: Synthetic

<400> SEQUENCE: 113

Ala Ala Ala Ala
1

<210> SEQ ID NO 114
<211> LENGTH: 4
<212> TYPE: PRT
<213> ORGANISM: Artificial Sequence
<220> FEATURE:
<223> OTHER INFORMATION: Synthetic

<400> SEQUENCE: 114

Ala Ala Ala Ala
1

<210> SEQ ID NO 115
<211> LENGTH: 15
<212> TYPE: PRT
<213> ORGANISM: Artificial Sequence
<220> FEATURE:
<223> OTHER INFORMATION: Synthetic

<400> SEQUENCE: 115

Gly Gly Gly Gly Ser Gly Gly Gly Gly Ser Gly Gly Gly Gly Ser
1               5                   10                  15

<210> SEQ ID NO 116
<211> LENGTH: 366
<212> TYPE: DNA
<213> ORGANISM: Artificial Sequence
<220> FEATURE:
<223> OTHER INFORMATION: Synthetic

<400> SEQUENCE: 116
caggtacagc tgcagcagtc aggggctgag gtgaagaagc ctggatcctc agtgaaggtc      60
tcctgcaagg cttctggagg caccttcagc agctatgcta tcagctgggt gcgacaggcc     120
cctggacaag ggcttgagtg gatgggaggg atcatcccta tccttggtat agcaaactac     180
gcacagaagt tccagggcag agtcacgatt accgcggacg aatccacgag cacagcctac     240
atggagctga gcagcctgag atctgaggac acggccgtgt attactgtgc gagaggaggg     300
gcgggcggtt cggggagtta ttatccccctc atctggggcc aagggaccac ggtcaccgtc     360
tcctca                                                                 366

<210> SEQ ID NO 117
<211> LENGTH: 333
<212> TYPE: DNA
<213> ORGANISM: Artificial Sequence
<220> FEATURE:
<223> OTHER INFORMATION: Synthetic

<400> SEQUENCE: 117
gaaattgtgt tgacgcagtc tccagccacc ctgtctttgt ctccagggga aagagccacc      60

```
ctctcctgcg gggccagtca gagtgttagc agcagctact tagcctggta ccagcagaaa    120
cctggccagg ctcccaggct cctcatctat gatgcatcca gcagggccac tggcatcccg    180
gccaggttca gtggcagtgg gtctgggaca gacttcactc tcaccatcag cagcctagag    240
cctgaagatt ttgcagttta ttactgtcag cagcgtagta gctggcctcc cacgtggacg    300
ttcggccaag ggaccaagct ggaaatcaaa cgt                                 333
```

<210> SEQ ID NO 118
<211> LENGTH: 357
<212> TYPE: DNA
<213> ORGANISM: Artificial Sequence
<220> FEATURE:
<223> OTHER INFORMATION: Synthetic

<400> SEQUENCE: 118

```
caggtacagc tgcagcagtc aggggctgag gtgaagaagc ctgggtcctc ggtgaaggtc     60
tcttgcaagg cttctggagg caccttcagc agctatgcta tcagctgggt gcgacaggcc    120
cctggacaag gctcgagtg atgggaggg atcatcccta tccttggtat agcaaactac    180
gcacagaagt tccagggcag agtcacgatt accgcggacg aatccacgag cacagcctac    240
atggagctga gcagcctgag atctgaggac acggccgtgt attactgtgc aacaggtggt    300
tcggggagat atgctttgga tatctggggc caagggacaa tggtcaccgt ctcttca      357
```

<210> SEQ ID NO 119
<211> LENGTH: 330
<212> TYPE: DNA
<213> ORGANISM: Artificial Sequence
<220> FEATURE:
<223> OTHER INFORMATION: Synthetic

<400> SEQUENCE: 119

```
gaaattgtgt tgacgcagtc tccagccacc ctgtccttgt ctccagggga aagagccacc     60
ctctcctgca gggccagtca gagtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcaact ggcctccgtc gtacactttt    300
ggccagggga ccaagctgga gatcaaacgt                                    330
```

<210> SEQ ID NO 120
<211> LENGTH: 351
<212> TYPE: DNA
<213> ORGANISM: Artificial Sequence
<220> FEATURE:
<223> OTHER INFORMATION: Synthetic

<400> SEQUENCE: 120

```
caggtgcagc tggtgcaatc tggggctgag gtgaagaagc ctgggtcctc ggtgaaggtc     60
tcctgcaagg cttctggagg caccttcagc agctatgcta tcagctgggt gcgacaggcc    120
cctggacaag gcttgagtg atgggaggg atcatcccta tccttggtac agcaaactac    180
gcacagaagt tccagggcag agtcacgatt accgcggacg aatccacgag cacagcctac    240
atggagctga gcagcctgag atctgaggac acggccgtgt attactgtgc gagatggggt    300
gggggagctt ttgatatctg ggccaaggg acaatggtca ccgtctcttc a             351
```

<210> SEQ ID NO 121

<211> LENGTH: 330
<212> TYPE: DNA
<213> ORGANISM: Artificial Sequence
<220> FEATURE:
<223> OTHER INFORMATION: Synthetic

<400> SEQUENCE: 121

```
gaaattgtgt tgacgcagtc tccaggcacc ctgtctttgt ctccagggga aagagccacc      60
ctctcctgca gggccagtca gagtgttggg ggctacttag cctggtacca acagaaacct     120
ggccaggctc ccaggctcct catctatgat gcatccaaca gggccaccgg catcccagcc     180
aggttcagtg gcagtgggtc tgggacagac ttcactctca ccatcagcag cctagagcct     240
gaagattttg cagtttatta ctgtcagcag cgtaacaact ggcctccgat gtacactttt     300
ggccagggga ccaagctgga aatcaaacgt                                      330
```

<210> SEQ ID NO 122
<211> LENGTH: 466
<212> TYPE: PRT
<213> ORGANISM: Artificial Sequence
<220> FEATURE:
<223> OTHER INFORMATION: Synthetic

<400> SEQUENCE: 122

```
Gln Val Gln Leu Gln Gln Ser Gly Ala Glu Val Lys Lys Pro Gly Ser
1               5                   10                  15

Ser Val Lys Val Ser Cys Lys Ala Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Gly Ser Gly Arg Tyr Ala Leu Asp Ile Trp Gly Gln Gly
            100                 105                 110

Thr Met Val Thr Val Ser Ser Gly Gly Gly Ser Gly Gly Gly Gly
        115                 120                 125

Ser Gly Gly Gly Gly Ser Glu Ile Val Leu Thr Gln Ser Pro Ala Thr
    130                 135                 140

Leu Ser Leu Ser Pro Gly Glu Arg Ala Thr Leu Ser Cys Arg Ala Ser
145                 150                 155                 160

Gln Ser Val Ser Ser Tyr Leu Ala Trp Tyr Gln Gln Lys Pro Gly Gln
                165                 170                 175

Ala Pro Arg Leu Leu Ile Tyr Asp Ala Ser Asn Arg Ala Thr Gly Ile
            180                 185                 190

Pro Ala Arg Phe Ser Gly Ser Gly Ser Gly Thr Asp Phe Thr Leu Thr
        195                 200                 205

Ile Ser Ser Leu Glu Pro Glu Asp Phe Ala Val Tyr Tyr Cys Gln Gln
    210                 215                 220

Arg Ser Asn Trp Pro Pro Ser Tyr Thr Phe Gly Gln Gly Thr Lys Leu
225                 230                 235                 240

Glu Ile Lys Arg Ala Ala Ala Ile Glu Val Met Tyr Pro Pro Pro Tyr
                245                 250                 255

Leu Asp Asn Glu Lys Ser Asn Gly Thr Ile Ile His Val Lys Gly Lys
```

```
                     260                 265                 270
His Leu Cys Pro Ser Pro Leu Phe Pro Gly Pro Ser Lys Pro Phe Trp
            275                 280                 285
Val Leu Val Val Val Gly Gly Val Leu Ala Cys Tyr Ser Leu Leu Val
        290                 295                 300
Thr Val Ala Phe Ile Ile Phe Trp Val Arg Ser Lys Arg Ser Arg Leu
305                 310                 315                 320
Leu His Ser Asp Tyr Met Asn Met Thr Pro Arg Arg Pro Gly Pro Thr
                325                 330                 335
Arg Lys His Tyr Gln Pro Tyr Ala Pro Pro Arg Asp Phe Ala Ala Tyr
            340                 345                 350
Arg Ser Arg Val Lys Phe Ser Arg Ser Ala Asp Ala Pro Ala Tyr Gln
        355                 360                 365
Gln Gly Gln Asn Gln Leu Tyr Asn Glu Leu Asn Leu Gly Arg Arg Glu
    370                 375                 380
Glu Tyr Asp Val Leu Asp Lys Arg Arg Gly Arg Asp Pro Glu Met Gly
385                 390                 395                 400
Gly Lys Pro Arg Arg Lys Asn Pro Gln Glu Gly Leu Tyr Asn Glu Leu
                405                 410                 415
Gln Lys Asp Lys Met Ala Glu Ala Tyr Ser Glu Ile Gly Met Lys Gly
            420                 425                 430
Glu Arg Arg Arg Gly Lys Gly His Asp Gly Leu Tyr Gln Gly Leu Ser
        435                 440                 445
Thr Ala Thr Lys Asp Thr Tyr Asp Ala Leu His Met Gln Ala Leu Pro
    450                 455                 460
Pro Arg
465

<210> SEQ ID NO 123
<211> LENGTH: 470
<212> TYPE: PRT
<213> ORGANISM: Artificial Sequence
<220> FEATURE:
<223> OTHER INFORMATION: Synthetic

<400> SEQUENCE: 123

Gln Val Gln Leu Gln Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Gly Ile Ile Pro Ile Leu Gly Ile Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Thr Gly Gly Ser Gly Arg Tyr Ala Leu Asp Ile Trp Gly Gln Gly
            100                 105                 110
Thr Met Val Thr Val Ser Ser Gly Gly Gly Gly Ser Gly Gly Gly Gly
        115                 120                 125
Ser Gly Gly Gly Gly Ser Glu Ile Val Leu Thr Gln Ser Pro Ala Thr
    130                 135                 140
Leu Ser Leu Ser Pro Gly Glu Arg Ala Thr Leu Ser Cys Arg Ala Ser
```

145                 150                 155                 160
Gln Ser Val Ser Ser Tyr Leu Ala Trp Tyr Gln Gln Lys Pro Gly Gln
                165                 170                 175

Ala Pro Arg Leu Leu Ile Tyr Asp Ala Ser Asn Arg Ala Thr Gly Ile
            180                 185                 190

Pro Ala Arg Phe Ser Gly Ser Gly Ser Gly Thr Asp Phe Thr Leu Thr
        195                 200                 205

Ile Ser Ser Leu Glu Pro Glu Asp Phe Ala Val Tyr Tyr Cys Gln Gln
    210                 215                 220

Arg Ser Asn Trp Pro Pro Ser Tyr Thr Phe Gly Gln Gly Thr Lys Leu
225                 230                 235                 240

Glu Ile Lys Arg Ala Ala Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Ile Tyr Ile Trp Ala Pro Leu Ala Gly Thr Cys Gly
    290                 295                 300

Val Leu Leu Leu Ser Leu Val Ile Thr Leu Tyr Cys Lys Arg Gly Arg
305                 310                 315                 320

Lys Lys Leu Leu Tyr Ile Phe Lys Gln Pro Phe Met Arg Pro Val Gln
                325                 330                 335

Thr Thr Gln Glu Glu Asp Gly Cys Ser Cys Arg Phe Pro Glu Glu Glu
            340                 345                 350

Glu Gly Gly Cys Glu Leu Arg Val Lys Phe Ser Arg Ser Ala Asp Ala
        355                 360                 365

Pro Ala Tyr Lys Gln Gly Gln Asn Gln Leu Tyr Asn Glu Leu Asn Leu
    370                 375                 380

Gly Arg Arg Glu Glu Tyr Asp Val Leu Asp Lys Arg Arg Gly Arg Asp
385                 390                 395                 400

Pro Glu Met Gly Gly Lys Pro Arg Arg Lys Asn Pro Gln Glu Gly Leu
                405                 410                 415

Tyr Asn Glu Leu Gln Lys Asp Lys Met Ala Glu Ala Tyr Ser Glu Ile
            420                 425                 430

Gly Met Lys Gly Glu Arg Arg Arg Gly Lys Gly His Asp Gly Leu Tyr
        435                 440                 445

Gln Gly Leu Ser Thr Ala Thr Lys Asp Thr Tyr Asp Ala Leu His Met
    450                 455                 460

Gln Ala Leu Pro Pro Arg
465                 470

<210> SEQ ID NO 124
<211> LENGTH: 530
<212> TYPE: PRT
<213> ORGANISM: Artificial Sequence
<220> FEATURE:
<223> OTHER INFORMATION: Synthetic

<400> SEQUENCE: 124

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met

Gly Gly Ile Ile Pro Ile Leu Gly Ile Ala Asn Tyr Ala Gln Lys Phe
 50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Thr Gly Gly Ser Gly Arg Tyr Ala Leu Asp Ile Trp Gly Gln Gly
                100                 105                 110
Thr Met Val Thr Val Ser Ser Gly Gly Gly Ser Gly Gly Gly Gly
                115                 120                 125
Ser Gly Gly Gly Gly Ser Glu Ile Val Leu Thr Gln Ser Pro Ala Thr
                130                 135                 140
Leu Ser Leu Ser Pro Gly Glu Arg Ala Thr Leu Ser Cys Arg Ala Ser
145                 150                 155                 160
Gln Ser Val Ser Ser Tyr Leu Ala Trp Tyr Gln Gln Lys Pro Gly Gln
                165                 170                 175
Ala Pro Arg Leu Leu Ile Tyr Asp Ala Ser Asn Arg Ala Thr Gly Ile
                180                 185                 190
Pro Ala Arg Phe Ser Gly Ser Gly Ser Gly Thr Asp Phe Thr Leu Thr
                195                 200                 205
Ile Ser Ser Leu Glu Pro Glu Asp Phe Ala Val Tyr Tyr Cys Gln Gln
210                 215                 220
Arg Ser Asn Trp Pro Pro Ser Tyr Thr Phe Gly Gln Gly Thr Lys Leu
225                 230                 235                 240
Glu Ile Lys Arg Ala Ala Ala Phe Val Pro Val Phe Leu Pro Ala Lys
                245                 250                 255
Pro Thr Thr Thr Pro Ala Pro Arg Pro Pro Thr Pro Ala Pro Thr Ile
                260                 265                 270
Ala Ser Gln Pro Leu Ser Leu Arg Pro Glu Ala Cys Arg Pro Ala Ala
                275                 280                 285
Gly Gly Ala Val His Thr Arg Gly Leu Asp Phe Ala Cys Asp Ile Tyr
                290                 295                 300
Ile Trp Ala Pro Leu Ala Gly Thr Cys Gly Val Leu Leu Leu Ser Leu
305                 310                 315                 320
Val Ile Thr Leu Tyr Cys Asn His Arg Asn Arg Ser Lys Arg Ser Arg
                325                 330                 335
Leu Leu His Ser Asp Tyr Met Asn Met Thr Pro Arg Arg Pro Gly Pro
                340                 345                 350
Thr Arg Lys His Tyr Gln Pro Tyr Ala Pro Pro Arg Asp Phe Ala Ala
                355                 360                 365
Tyr Arg Ser Arg Phe Ser Val Val Lys Arg Gly Arg Lys Lys Leu Leu
                370                 375                 380
Tyr Ile Phe Lys Gln Pro Phe Met Arg Pro Val Gln Thr Thr Gln Glu
385                 390                 395                 400
Glu Asp Gly Cys Ser Cys Arg Phe Pro Glu Glu Glu Glu Gly Gly Cys
                405                 410                 415
Glu Leu Arg Val Lys Phe Ser Arg Ser Ala Asp Ala Pro Ala Tyr Gln
                420                 425                 430
Gln Gly Gln Asn Gln Leu Tyr Asn Glu Leu Asn Leu Gly Arg Arg Glu
                435                 440                 445
Glu Tyr Asp Val Leu Asp Lys Arg Arg Gly Arg Asp Pro Glu Met Gly
                450                 455                 460

Gly Lys Pro Arg Arg Lys Asn Pro Gln Glu Gly Leu Tyr Asn Glu Leu
465                 470                 475                 480

Gln Lys Asp Lys Met Ala Glu Ala Tyr Ser Glu Ile Gly Met Lys Gly
            485                 490                 495

Glu Arg Arg Arg Gly Lys Gly His Asp Gly Leu Tyr Gln Gly Leu Ser
            500                 505                 510

Thr Ala Thr Lys Asp Thr Tyr Asp Ala Leu His Met Gln Ala Leu Pro
            515                 520                 525

Pro Arg
    530

<210> SEQ ID NO 125
<211> LENGTH: 470
<212> TYPE: PRT
<213> ORGANISM: Artificial Sequence
<220> FEATURE:
<223> OTHER INFORMATION: Synthetic

<400> SEQUENCE: 125

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Ala Gly Gly Ser Gly Ser Tyr Tyr Pro Leu Ile Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Gly Ser Glu Ile Val Leu Thr Gln Ser
    130                 135                 140

Pro Ala Thr Leu Ser Leu Ser Pro Gly Glu Arg Ala Thr Leu Ser Cys
145                 150                 155                 160

Gly Ala Ser Gln Ser Val Ser Ser Ser Tyr Leu Ala Trp Tyr Gln Gln
                165                 170                 175

Lys Pro Gly Gln Ala Pro Arg Leu Leu Ile Tyr Asp Ala Ser Ser Arg
            180                 185                 190

Ala Thr Gly Ile Pro Ala Arg Phe Ser Gly Ser Gly Ser Gly Thr Asp
        195                 200                 205

Phe Thr Leu Thr Ile Ser Ser Leu Glu Pro Glu Asp Phe Ala Val Tyr
    210                 215                 220

Tyr Cys Gln Gln Arg Ser Ser Trp Pro Pro Thr Trp Thr Phe Gly Gln
225                 230                 235                 240

Gly Thr Lys Leu Glu Ile Lys Arg Ala Ala Ala Ile Glu Val Met Tyr
                245                 250                 255

Pro Pro Pro Tyr Leu Asp Asn Glu Lys Ser Asn Gly Thr Ile Ile His
            260                 265                 270

Val Lys Gly Lys His Leu Cys Pro Ser Pro Leu Phe Pro Gly Pro Ser
        275                 280                 285

```
Lys Pro Phe Trp Val Leu Val Val Gly Gly Val Leu Ala Cys Tyr
    290                 295                 300

Ser Leu Leu Val Thr Val Ala Phe Ile Ile Phe Trp Val Arg Ser Lys
305                 310                 315                 320

Arg Ser Arg Leu Leu His Ser Asp Tyr Met Asn Met Thr Pro Arg Arg
                325                 330                 335

Pro Gly Pro Thr Arg Lys His Tyr Gln Pro Tyr Ala Pro Pro Arg Asp
            340                 345                 350

Phe Ala Ala Tyr Arg Ser Arg Val Lys Phe Ser Arg Ser Ala Asp Ala
        355                 360                 365

Pro Ala Tyr Gln Gln Gly Gln Asn Gln Leu Tyr Asn Glu Leu Asn Leu
    370                 375                 380

Gly Arg Arg Glu Glu Tyr Asp Val Leu Asp Lys Arg Arg Gly Arg Asp
385                 390                 395                 400

Pro Glu Met Gly Gly Lys Pro Arg Arg Lys Asn Pro Gln Glu Gly Leu
                405                 410                 415

Tyr Asn Glu Leu Gln Lys Asp Lys Met Ala Glu Ala Tyr Ser Glu Ile
            420                 425                 430

Gly Met Lys Gly Glu Arg Arg Arg Gly Lys Gly His Asp Gly Leu Tyr
        435                 440                 445

Gln Gly Leu Ser Thr Ala Thr Lys Asp Thr Tyr Asp Ala Leu His Met
    450                 455                 460

Gln Ala Leu Pro Pro Arg
465                 470

<210> SEQ ID NO 126
<211> LENGTH: 474
<212> TYPE: PRT
<213> ORGANISM: Artificial Sequenece
<220> FEATURE:
<223> OTHER INFORMATION: Synthetic

<400> SEQUENCE: 126

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Ala Gly Gly Ser Gly Ser Tyr Tyr Pro Leu Ile Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Gly Ser Glu Ile Val Leu Thr Gln Ser
    130                 135                 140

Pro Ala Thr Leu Ser Leu Ser Pro Gly Glu Arg Ala Thr Leu Ser Cys
145                 150                 155                 160

Gly Ala Ser Gln Ser Val Ser Ser Ser Tyr Leu Ala Trp Tyr Gln Gln
                165                 170                 175
```

```
Lys Pro Gly Gln Ala Pro Arg Leu Leu Ile Tyr Asp Ala Ser Ser Arg
                180                 185                 190

Ala Thr Gly Ile Pro Ala Arg Phe Ser Gly Ser Gly Ser Gly Thr Asp
            195                 200                 205

Phe Thr Leu Thr Ile Ser Ser Leu Glu Pro Glu Asp Phe Ala Val Tyr
    210                 215                 220

Tyr Cys Gln Gln Arg Ser Ser Trp Pro Pro Thr Trp Thr Phe Gly Gln
225                 230                 235                 240

Gly Thr Lys Leu Glu Ile Lys Arg Ala Ala Thr Thr Thr Pro Ala
                245                 250                 255

Pro Arg Pro Pro Thr Pro Ala Pro Thr Ile Ala Ser Gln Pro Leu Ser
                260                 265                 270

Leu Arg Pro Glu Ala Cys Arg Pro Ala Ala Gly Gly Ala Val His Thr
            275                 280                 285

Arg Gly Leu Asp Phe Ala Cys Asp Ile Tyr Ile Trp Ala Pro Leu Ala
            290                 295                 300

Gly Thr Cys Gly Val Leu Leu Leu Ser Leu Val Ile Thr Leu Tyr Cys
305                 310                 315                 320

Lys Arg Gly Arg Lys Lys Leu Leu Tyr Ile Phe Lys Gln Pro Phe Met
                325                 330                 335

Arg Pro Val Gln Thr Thr Gln Glu Glu Asp Gly Cys Ser Cys Arg Phe
                340                 345                 350

Pro Glu Glu Glu Glu Gly Gly Cys Glu Leu Arg Val Lys Phe Ser Arg
                355                 360                 365

Ser Ala Asp Ala Pro Ala Tyr Lys Gln Gly Gln Asn Gln Leu Tyr Asn
            370                 375                 380

Glu Leu Asn Leu Gly Arg Arg Glu Glu Tyr Asp Val Leu Asp Lys Arg
385                 390                 395                 400

Arg Gly Arg Asp Pro Glu Met Gly Gly Lys Pro Arg Arg Lys Asn Pro
                405                 410                 415

Gln Glu Gly Leu Tyr Asn Glu Leu Gln Lys Asp Lys Met Ala Glu Ala
                420                 425                 430

Tyr Ser Glu Ile Gly Met Lys Gly Glu Arg Arg Arg Gly Lys Gly His
            435                 440                 445

Asp Gly Leu Tyr Gln Gly Leu Ser Thr Ala Thr Lys Asp Thr Tyr Asp
    450                 455                 460

Ala Leu His Met Gln Ala Leu Pro Pro Arg
465                 470

<210> SEQ ID NO 127
<211> LENGTH: 534
<212> TYPE: PRT
<213> ORGANISM: Artificial Sequence
<220> FEATURE:
<223> OTHER INFORMATION: Synthetic

<400> SEQUENCE: 127

Gln Val Gln Leu Gln Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60
```

```
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Ala Gly Gly Ser Gly Ser Tyr Tyr Pro Leu Ile Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Ser Glu Ile Val Leu Thr Gln Ser
130                 135                 140

Pro Ala Thr Leu Ser Leu Ser Pro Gly Glu Arg Ala Thr Leu Ser Cys
145                 150                 155                 160

Gly Ala Ser Gln Ser Val Ser Ser Ser Tyr Leu Ala Trp Tyr Gln Gln
                165                 170                 175

Lys Pro Gly Gln Ala Pro Arg Leu Leu Ile Tyr Asp Ala Ser Ser Arg
            180                 185                 190

Ala Thr Gly Ile Pro Ala Arg Phe Ser Gly Ser Gly Ser Gly Thr Asp
        195                 200                 205

Phe Thr Leu Thr Ile Ser Ser Leu Glu Pro Glu Asp Phe Ala Val Tyr
    210                 215                 220

Tyr Cys Gln Gln Arg Ser Ser Trp Pro Pro Thr Trp Thr Phe Gly Gln
225                 230                 235                 240

Gly Thr Lys Leu Glu Ile Lys Arg Ala Ala Ala Phe Val Pro Val Phe
                245                 250                 255

Leu Pro Ala Lys Pro Thr Thr Thr Pro Ala Pro Arg Pro Pro Thr Pro
            260                 265                 270

Ala Pro Thr Ile Ala Ser Gln Pro Leu Ser Leu Arg Pro Glu Ala Cys
        275                 280                 285

Arg Pro Ala Ala Gly Gly Ala Val His Thr Arg Gly Leu Asp Phe Ala
290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Asn His Arg Asn Arg Ser
                325                 330                 335

Lys Arg Ser Arg Leu Leu His Ser Asp Tyr Met Asn Met Thr Pro Arg
            340                 345                 350

Arg Pro Gly Pro Thr Arg Lys His Tyr Gln Pro Tyr Ala Pro Pro Arg
        355                 360                 365

Asp Phe Ala Ala Tyr Arg Ser Arg Phe Ser Val Val Lys Arg Gly Arg
    370                 375                 380

Lys Lys Leu Leu Tyr Ile Phe Lys Gln Pro Phe Met Arg Pro Val Gln
385                 390                 395                 400

Thr Thr Gln Glu Glu Asp Gly Cys Ser Cys Arg Phe Pro Glu Glu Glu
                405                 410                 415

Glu Gly Gly Cys Glu Leu Arg Val Lys Phe Ser Arg Ser Ala Asp Ala
            420                 425                 430

Pro Ala Tyr Gln Gln Gly Gln Asn Gln Leu Tyr Asn Glu Leu Asn Leu
        435                 440                 445

Gly Arg Arg Glu Glu Tyr Asp Val Leu Asp Lys Arg Arg Gly Arg Asp
    450                 455                 460

Pro Glu Met Gly Gly Lys Pro Arg Arg Lys Asn Pro Gln Glu Gly Leu
465                 470                 475                 480
```

Tyr Asn Glu Leu Gln Lys Asp Lys Met Ala Glu Ala Tyr Ser Glu Ile
            485                 490                 495

Gly Met Lys Gly Glu Arg Arg Gly Lys Gly His Asp Gly Leu Tyr
        500                 505                 510

Gln Gly Leu Ser Thr Ala Thr Lys Asp Thr Tyr Asp Ala Leu His Met
        515                 520                 525

Gln Ala Leu Pro Pro Arg
        530

<210> SEQ ID NO 128
<211> LENGTH: 464
<212> TYPE: PRT
<213> ORGANISM: Artificial Sequence
<220> FEATURE:
<223> OTHER INFORMATION: Synthetic

<400> SEQUENCE: 128

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Gly Gly Ala Phe Asp Ile Trp Gly Gln Gly Thr Met
            100                 105                 110

Val Thr Val Ser Ser Gly Gly Gly Ser Gly Gly Gly Gly Ser Gly
        115                 120                 125

Gly Gly Gly Ser Glu Ile Val Leu Thr Gln Ser Pro Gly Thr Leu Ser
    130                 135                 140

Leu Ser Pro Gly Glu Arg Ala Thr Leu Ser Cys Arg Ala Ser Gln Ser
145                 150                 155                 160

Val Gly Gly Tyr Leu Ala Trp Tyr Gln Gln Lys Pro Gly Gln Ala Pro
                165                 170                 175

Arg Leu Leu Ile Tyr Asp Ala Ser Asn Arg Ala Thr Gly Ile Pro Ala
            180                 185                 190

Arg Phe Ser Gly Ser Gly Ser Gly Thr Asp Phe Thr Leu Thr Ile Ser
        195                 200                 205

Ser Leu Glu Pro Glu Asp Phe Ala Val Tyr Tyr Cys Gln Gln Arg Asn
    210                 215                 220

Asn Trp Pro Pro Met Tyr Thr Phe Gly Gln Gly Thr Lys Leu Glu Ile
225                 230                 235                 240

Lys Arg Ala Ala Ala Ile Glu Val Met Tyr Pro Pro Pro Tyr Leu Asp
                245                 250                 255

Asn Glu Lys Ser Asn Gly Thr Ile Ile His Val Lys Gly Lys His Leu
            260                 265                 270

Cys Pro Ser Pro Leu Phe Pro Gly Pro Ser Lys Pro Phe Trp Val Leu
        275                 280                 285

Val Val Val Gly Gly Val Leu Ala Cys Tyr Ser Leu Leu Val Thr Val
    290                 295                 300

```
Ala Phe Ile Ile Phe Trp Val Arg Ser Lys Arg Ser Arg Leu Leu His
305                 310                 315                 320

Ser Asp Tyr Met Asn Met Thr Pro Arg Arg Pro Gly Pro Thr Arg Lys
            325                 330                 335

His Tyr Gln Pro Tyr Ala Pro Pro Arg Asp Phe Ala Ala Tyr Arg Ser
            340                 345                 350

Arg Val Lys Phe Ser Arg Ser Ala Asp Ala Pro Ala Tyr Gln Gln Gly
            355                 360                 365

Gln Asn Gln Leu Tyr Asn Glu Leu Asn Leu Gly Arg Arg Glu Glu Tyr
370                 375                 380

Asp Val Leu Asp Lys Arg Arg Gly Arg Asp Pro Glu Met Gly Gly Lys
385                 390                 395                 400

Pro Arg Arg Lys Asn Pro Gln Glu Gly Leu Tyr Asn Glu Leu Gln Lys
            405                 410                 415

Asp Lys Met Ala Glu Ala Tyr Ser Glu Ile Gly Met Lys Gly Glu Arg
            420                 425                 430

Arg Arg Gly Lys Gly His Asp Gly Leu Tyr Gln Gly Leu Ser Thr Ala
            435                 440                 445

Thr Lys Asp Thr Tyr Asp Ala Leu His Met Gln Ala Leu Pro Pro Arg
450                 455                 460

<210> SEQ ID NO 129
<211> LENGTH: 468
<212> TYPE: PRT
<213> ORGANISM: Artificial Sequence
<220> FEATURE:
<223> OTHER INFORMATION: Synthetic

<400> SEQUENCE: 129

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Gly Ala Phe Asp Ile Trp Gly Gln Gly Thr Met
            100                 105                 110

Val Thr Val Ser Ser Gly Gly Gly Ser Gly Gly Gly Gly Ser Gly
        115                 120                 125

Gly Gly Gly Ser Glu Ile Val Leu Thr Gln Ser Pro Gly Thr Leu Ser
    130                 135                 140

Leu Ser Pro Gly Glu Arg Ala Thr Leu Ser Cys Arg Ala Ser Gln Ser
145                 150                 155                 160

Val Gly Gly Tyr Leu Ala Trp Tyr Gln Gln Lys Pro Gly Gln Ala Pro
                165                 170                 175

Arg Leu Leu Ile Tyr Asp Ala Ser Asn Arg Ala Thr Gly Ile Pro Ala
            180                 185                 190

Arg Phe Ser Gly Ser Gly Ser Gly Thr Asp Phe Thr Leu Thr Ile Ser
        195                 200                 205
```

Ser Leu Glu Pro Glu Asp Phe Ala Val Tyr Tyr Cys Gln Gln Arg Asn
210                 215                 220

Asn Trp Pro Pro Met Tyr Thr Phe Gly Gln Gly Thr Lys Leu Glu Ile
225                 230                 235                 240

Lys Arg Ala Ala Ala Thr Thr Thr Pro Ala Pro Arg Pro Pro Thr Pro
            245                 250                 255

Ala Pro Thr Ile Ala Ser Gln Pro Leu Ser Leu Arg Pro Glu Ala Cys
            260                 265                 270

Arg Pro Ala Ala Gly Gly Ala Val His Thr Arg Gly Leu Asp Phe Ala
            275                 280                 285

Cys Asp Ile Tyr Ile Trp Ala Pro Leu Ala Gly Thr Cys Gly Val Leu
290                 295                 300

Leu Leu Ser Leu Val Ile Thr Leu Tyr Cys Lys Arg Gly Arg Lys Lys
305                 310                 315                 320

Leu Leu Tyr Ile Phe Lys Gln Pro Phe Met Arg Pro Val Gln Thr Thr
            325                 330                 335

Gln Glu Glu Asp Gly Cys Ser Cys Arg Phe Pro Glu Glu Glu Glu Gly
            340                 345                 350

Gly Cys Glu Leu Arg Val Lys Phe Ser Arg Ser Ala Asp Ala Pro Ala
            355                 360                 365

Tyr Lys Gln Gly Gln Asn Gln Leu Tyr Asn Glu Leu Asn Leu Gly Arg
370                 375                 380

Arg Glu Glu Tyr Asp Val Leu Asp Lys Arg Gly Arg Asp Pro Glu
385                 390                 395                 400

Met Gly Gly Lys Pro Arg Arg Lys Asn Pro Gln Glu Gly Leu Tyr Asn
            405                 410                 415

Glu Leu Gln Lys Asp Lys Met Ala Glu Ala Tyr Ser Glu Ile Gly Met
            420                 425                 430

Lys Gly Glu Arg Arg Arg Gly Lys Gly His Asp Gly Leu Tyr Gln Gly
            435                 440                 445

Leu Ser Thr Ala Thr Lys Asp Thr Tyr Asp Ala Leu His Met Gln Ala
450                 455                 460

Leu Pro Pro Arg
465

<210> SEQ ID NO 130
<211> LENGTH: 528
<212> TYPE: PRT
<213> ORGANISM: Artificial Sequence
<220> FEATURE:
<223> OTHER INFORMATION: Synthetic

<400> SEQUENCE: 130

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

```
Ala Arg Trp Gly Gly Ala Phe Asp Ile Trp Gly Gln Gly Thr Met
            100                 105                 110

Val Thr Val Ser Ser Gly Gly Gly Ser Gly Gly Gly Gly Ser Gly
        115                 120                 125

Gly Gly Gly Ser Glu Ile Val Leu Thr Gln Ser Pro Gly Thr Leu Ser
        130                 135                 140

Leu Ser Pro Gly Glu Arg Ala Thr Leu Ser Cys Arg Ala Ser Gln Ser
145                 150                 155                 160

Val Gly Gly Tyr Leu Ala Trp Tyr Gln Gln Lys Pro Gly Gln Ala Pro
                165                 170                 175

Arg Leu Leu Ile Tyr Asp Ala Ser Asn Arg Ala Thr Gly Ile Pro Ala
                180                 185                 190

Arg Phe Ser Gly Ser Gly Ser Gly Thr Asp Phe Thr Leu Thr Ile Ser
            195                 200                 205

Ser Leu Glu Pro Glu Asp Phe Ala Val Tyr Tyr Cys Gln Gln Arg Asn
210                 215                 220

Asn Trp Pro Pro Met Tyr Thr Phe Gly Gln Gly Thr Lys Leu Glu Ile
225                 230                 235                 240

Lys Arg Ala Ala Ala Phe Val Pro Val Phe Leu Pro Ala Lys Pro Thr
                245                 250                 255

Thr Thr Pro Ala Pro Arg Pro Pro Thr Pro Ala Pro Thr Ile Ala Ser
            260                 265                 270

Gln Pro Leu Ser Leu Arg Pro Glu Ala Cys Arg Pro Ala Ala Gly Gly
            275                 280                 285

Ala Val His Thr Arg Gly Leu Asp Phe Ala Cys Asp Ile Tyr Ile Trp
            290                 295                 300

Ala Pro Leu Ala Gly Thr Cys Gly Val Leu Leu Leu Ser Leu Val Ile
305                 310                 315                 320

Thr Leu Tyr Cys Asn His Arg Asn Arg Ser Lys Arg Ser Arg Leu Leu
                325                 330                 335

His Ser Asp Tyr Met Asn Met Thr Pro Arg Arg Pro Gly Pro Thr Arg
            340                 345                 350

Lys His Tyr Gln Pro Tyr Ala Pro Pro Arg Asp Phe Ala Ala Tyr Arg
            355                 360                 365

Ser Arg Phe Ser Val Val Lys Arg Gly Arg Lys Lys Leu Leu Tyr Ile
370                 375                 380

Phe Lys Gln Pro Phe Met Arg Pro Val Gln Thr Thr Gln Glu Glu Asp
385                 390                 395                 400

Gly Cys Ser Cys Arg Phe Pro Glu Glu Glu Glu Gly Gly Cys Glu Leu
                405                 410                 415

Arg Val Lys Phe Ser Arg Ser Ala Asp Ala Pro Ala Tyr Gln Gln Gly
                420                 425                 430

Gln Asn Gln Leu Tyr Asn Glu Leu Asn Leu Gly Arg Arg Glu Glu Tyr
            435                 440                 445

Asp Val Leu Asp Lys Arg Arg Gly Arg Asp Pro Glu Met Gly Gly Lys
            450                 455                 460

Pro Arg Arg Lys Asn Pro Gln Glu Gly Leu Tyr Asn Glu Leu Gln Lys
465                 470                 475                 480

Asp Lys Met Ala Glu Ala Tyr Ser Glu Ile Gly Met Lys Gly Glu Arg
                485                 490                 495

Arg Arg Gly Lys Gly His Asp Gly Leu Tyr Gln Gly Leu Ser Thr Ala
            500                 505                 510

Thr Lys Asp Thr Tyr Asp Ala Leu His Met Gln Ala Leu Pro Pro Arg
```

515        520        525

<210> SEQ ID NO 131
<211> LENGTH: 1401
<212> TYPE: DNA
<213> ORGANISM: Artificial Sequence
<220> FEATURE:
<223> OTHER INFORMATION: Synthetic

<400> SEQUENCE: 131

| | |
|---|---|
| caagtccaac ttcagcagtc agggggcggag gtgaagaagc cgggctcctc cgtaaaggtg | 60 |
| tcgtgcaaag catcgggcgg tacattctcc tcctatgcga tctcatgggt gcgacaggca | 120 |
| cccgggcagg ggttggaatg gatgggtggt atcattccca ttctcgggat cgcgaactac | 180 |
| gcgcagaagt tcaaggcag agtaacaatt actgcagacg agtccacctc aaccgcctat | 240 |
| atggaactgt cgtcacttcg gtccgaagat acagccgtgt actattgtgc aacgggaggc | 300 |
| agcgggaggt atgcccttga catttgggga caggggacaa tggtcacagt aagctccgga | 360 |
| ggtgggggat caggaggcgg tggatcgggt ggggaggat cggaaattgt actcactcag | 420 |
| tcaccggcga ctctctccct cagcccggga gagcgggcca ccttgtcatg cagagccagc | 480 |
| cagagcgtat catcctatct tgcgtggtat cagcaaaaac ccggtcaggc cccaaggttg | 540 |
| ctgatctacg atgcgtcgaa tcgcgcgaca ggaatccctg ctaggttctc cgggtcgggc | 600 |
| tcggggaccg actttacgct tacgatcagc tcgctgaac cggaggactt cgccgtctac | 660 |
| tactgccagc agcggtcgaa ttggccgcct cctacacat ttggacaagg aacaaagctg | 720 |
| gaaatcaaga gagcggccgc aattgaagtt atgtatcctc ctccttacct agacaatgag | 780 |
| aagagcaatg gaaccattat ccatgtgaaa gggaaacacc tttgtccaag tccctatt | 840 |
| cccgaccttt ctaagccctt tgggtgctg gtggtggttg ggggagtcct ggcttgctat | 900 |
| agcttgctag taacagtggc ctttattatt ttctgggtga ggagtaagag gagcaggctc | 960 |
| ctgcacagtg actacatgaa catgactccc cgccgcccg ggcccacccg caagcattac | 1020 |
| cagccctatg ccccaccacg cgacttcgca gcctatcgct ccagagtgaa gttcagcagg | 1080 |
| agcgcagacg ccccccgcgta ccagcagggc cagaaccagc tctataacga gctcaatcta | 1140 |
| ggacgaagag aggagtacga tgttttggac aagagacgtg gccgggaccc tgagatgggg | 1200 |
| ggaaagccga gaaggaagaa ccctcaggaa ggcctgtaca atgaactgca gaaagataag | 1260 |
| atggcggagg cctacagtga gattgggatg aaaggcgagc gccggagggg caaggggcac | 1320 |
| gatggccttt accagggtct cagtacagcc accaaggaca cctacgacgc ccttcacatg | 1380 |
| caggccctgc ccctcgcta a | 1401 |

<210> SEQ ID NO 132
<211> LENGTH: 1413
<212> TYPE: DNA
<213> ORGANISM: Artificial Sequence
<220> FEATURE:
<223> OTHER INFORMATION: Synthetic

<400> SEQUENCE: 132

| | |
|---|---|
| caagtccaac ttcagcagtc agggggcggag gtgaagaagc cgggctcctc cgtaaaggtg | 60 |
| tcgtgcaaag catcgggcgg tacattctcc tcctatgcga tctcatgggt gcgacaggca | 120 |
| cccgggcagg ggttggaatg gatgggtggt atcattccca ttctcgggat cgcgaactac | 180 |
| gcgcagaagt tcaaggcag agtaacaatt actgcagacg agtccacctc aaccgcctat | 240 |
| atggaactgt cgtcacttcg gtccgaagat acagccgtgt actattgtgc aacgggaggc | 300 |

```
agcgggaggt atgcccttga catttgggga caggggacaa tggtcacagt aagctccgga    360
ggtgggggat caggaggcgg tggatcgggt ggggaggat cggaaattgt actcactcag     420
tcaccggcga ctctctccct cagcccggga gagcgggcca ccttgtcatg cagagccagc    480
cagagcgtat catcctatct tgcgtggtat cagcaaaaac ccggtcaggc cccaaggttg    540
ctgatctacg atgcgtcgaa tcgcgcgaca ggaatccctg ctaggttctc cgggtcgggc    600
tcggggaccg actttacgct tacgatcagc tcgctggaac cggaggactt cgccgtctac    660
tactgccagc agcggtcgaa ttggccgcct cctacacat ttggacaagg aacaaagctg     720
gaaatcaaga gagcggccgc aaccacgacg ccagcgccgc gaccaccaac accggcgccc    780
accatcgcgt cgcagcccct gtccctgcgc ccagaggcgt gccggccagc ggcgggggc     840 gcagtgcaca cgaggggct ggacttcgcc tgtgatatct acatctgggc gcccttggcc     900
gggacttgtg gggtccttct cctgtcactg gttatcaccc tttactgcaa acggggcaga    960
aagaaactcc tgtatatatt caaacaacca tttatgagac cagtacaaac tactcaagag   1020
gaagatggct gtagctgccg atttccagaa gaagaagaag gaggatgtga actgagagtg    1080
aagttcagca ggagcgcaga cgcccccgcg tacaagcagg ccagaaccga gctctataac   1140
gagctcaatc taggacgaag agaggagtac gatgttttgg acaagagacg tggccgggac   1200
cctgagatgg ggggaaagcc gagaaggaag aaccctcagg aaggcctgta caatgaactg    1260
cagaaagata agatggcgga ggcctacagt gagattggga tgaaaggcga gcgccggagg    1320
ggcaaggggc acgatggcct ttaccagggt ctcagtacag ccaccaagga cacctacgac    1380
gcccttcaca tgcaggccct gccccctcgc taa                                 1413

<210> SEQ ID NO 133
<211> LENGTH: 1593
<212> TYPE: DNA
<213> ORGANISM: Artificial Sequence
<220> FEATURE:
<223> OTHER INFORMATION: Synthetic

<400> SEQUENCE: 133
caagtccaac ttcagcagtc aggggcggag gtgaagaagc cgggctcctc cgtaaaggtg     60
tcgtgcaaag catcgggcgg tacattctcc tcctatgcga tctcatgggt gcgacaggca    120
cccgggcagg ggttggaatg gatgggtggt atcattccca ttctcgggat cgcgaactac    180
gcgcagaagt ttcaaggcag agtaacaatt actgcagacg agtccacctc aaccgcctat    240
atggaactgt cgtcacttcg gtccgaagat acagccgtgt actattgtgc aacgggaggc    300
agcgggaggt atgcccttga catttgggga caggggacaa tggtcacagt aagctccgga    360
ggtgggggat caggaggcgg tggatcgggt ggggaggat cggaaattgt actcactcag     420
tcaccggcga ctctctccct cagcccggga gagcgggcca ccttgtcatg cagagccagc    480
cagagcgtat catcctatct tgcgtggtat cagcaaaaac ccggtcaggc cccaaggttg    540
ctgatctacg atgcgtcgaa tcgcgcgaca ggaatccctg ctaggttctc cgggtcgggc    600
tcggggaccg actttacgct tacgatcagc tcgctggaac cggaggactt cgccgtctac    660
tactgccagc agcggtcgaa ttggccgcct cctacacat ttggacaagg aacaaagctg     720
gaaatcaaga gagcggccgc attcgtgccg gtcttcctgc cagcgaagcc caccacgacg    780
ccagcgccgc gaccaccaac accggcgccc accatcgcgt cgcagcccct gtccctgcgc    840
ccagaggcgt gccggccagc ggcgggggc gcagtgcaca cgaggggct ggacttcgcc     900
```

```
tgtgatatct acatctgggc gcccttggcc gggacttgtg gggtccttct cctgtcactg    960
gttatcaccc tttactgcaa ccacaggaac aggagtaaga ggagcaggct cctgcacagt   1020
gactacatga acatgactcc ccgccgcccc gggcccaccc gcaagcatta ccagccctat   1080
gccccaccac gcgacttcgc agcctatcgc tcccgtttct ctgttgttaa acggggcaga   1140
aagaagctcc tgtatatatt caaacaacca tttatgagac cagtacaaac tactcaagag   1200
gaagatggct gtagctgccg atttccagaa gaagaagaag gaggatgtga actgagagtg   1260
aagttcagca ggagcgcaga cgcccccgcg taccagcagg gccagaacca gctctataac   1320
gagctcaatc taggacgaag agaggagtac gatgttttgg acaagagacg tggccgggac   1380
cctgagatgg ggggaaagcc gagaaggaag aaccctcagg aaggcctgta caatgaactg   1440
cagaaagata gatggcgga ggcctacagt gagattggga tgaaaggcga gcgccggagg    1500
ggcaaggggc acgatggcct ttaccagggt ctcagtacag ccaccaagga cacctacgac   1560
gcccttcaca tgcaggccct gccccctcgc taa                                1593
```

<210> SEQ ID NO 134
<211> LENGTH: 1413
<212> TYPE: DNA
<213> ORGANISM: Artificial Sequence
<220> FEATURE:
<223> OTHER INFORMATION: Synthetic
<400> SEQUENCE: 134

```
caagtccagc tgcagcagtc aggagctgag gtgaagaagc ctggtagctc tgtcaaagtg     60
tcttgcaaag cctctggtgg tactttcagc tcttacgcca tttcttgggt gagacaggca    120
cccggacagg gtcttgaatg gatgggtgga atcatcccga ttcttgggat tgctaattac    180
gcacaaaagt tccagggaag ggtgaccatc accgcagacg aatctacctc cactgcttac    240
atggaactct cttccctgcg gtccgaggac accgccgtct actattgtgc caggggcggt    300 gccgaggaa gcggttctta ctatccgctg atttggggac aaggaaccac tgtgaccgtg    360
agctctggtg gaggcggatc cggtggtgga gggtccggag gcggaggatc tgagatcgtg    420
ctcactcaga gccagccac ccttagcctg agccctggtg agcgcgccac cctctcatgc    480
ggtgcctcac agagcgtgag ctcaagctat ctggcatggt accagcaaaa gccagggcag    540 gcccgagc tcctgatcta cgacgcatca tcacgggcta ccggtatccc ggcacgcttc    600
tctggaagcg gatcaggcac cgacttcacc ctgaccattt cttcacttga gcagaggac    660 tttgccgtgt actactgcca gcagcgctca agctggccgc ctacttggac tttcggacag    720
gggaccaagc tggagatcaa gcgcgcggcc gcaattgaag ttatgtatcc tcctccttac    780
ctagacaatg agaagagcaa tggaaccatt atccatgtga agggaaaca ctttgtcca     840 agtccctat ttcccggacc ttctaagccc ttttgggtgc tggtggtggt tgggggagtc    900
ctggcttgct atagcttgct agtaacagtg gcctttatta ttttctgggt gaggagtaag    960
aggagcaggc tcctgcacag tgactacatg aacatgactc ccgccgccc cgggcccacc    1020 cgcaagcatt accagcccta tgccccacca cgcgacttcg cagcctatcg ctccagagtg   1080
aagttcagca ggagcgcaga cgcccccgcg taccagcagg gccagaacca gctctataac   1140
gagctcaatc taggacgaag agaggagtac gatgttttgg acaagagacg tggccgggac   1200
cctgagatgg ggggaaagcc gagaaggaag aaccctcagg aaggcctgta caatgaactg   1260
cagaaagata gatggcgga ggcctacagt gagattggga tgaaaggcga gcgccggagg    1320
ggcaaggggc acgatggcct ttaccagggt ctcagtacag ccaccaagga cacctacgac   1380
```

```
gcccttcaca tgcaggccct gcccctcgc taa                                    1413
```

<210> SEQ ID NO 135
<211> LENGTH: 1425
<212> TYPE: DNA
<213> ORGANISM: Artificial Sequence
<220> FEATURE:
<223> OTHER INFORMATION: Synthetic

<400> SEQUENCE: 135

```
caagtccagc tgcagcagtc aggagctgag gtgaagaagc ctggtagctc tgtcaaagtg      60
tcttgcaaag cctctggtgg tactttcagc tcttacgcca tttcttgggt gagacaggca     120
cccggacagg gtcttgaatg gatgggtgga atcatcccga ttcttgggat tgctaattac     180
gcacaaaagt tccagggaag ggtgaccatc accgcagacg aatctacctc cactgcttac     240
atggaactct cttccctgcg gtccgaggac accgccgtct actattgtgc caggggcggt     300
gccggaggaa gcggttctta ctatccgctg atttggggac aaggaaccac tgtgaccgtg     360
agctctggtg gaggcggatc cggtggtgga gggtccggag gcggaggatc tgagatcgtg     420
ctcactcaga gcccagccac ccttagcctg agccctggtg agcgcgccac cctctcatgc     480
ggtgcctcac agagcgtgag ctcaagctat ctggcatggt accagcaaaa gccagggcag     540
gccccgaggc tcctgatcta cgacgcatca tcacgggcta ccgtatccc ggcacgcttc      600
tctggaagcg gatcaggcac cgacttcacc ctgaccattt cttcacttga gccagaggac     660
tttgccgtgt actactgcca gcagcgctca agctggccgc ctacttggac tttcggacag     720
gggaccaagc tggagatcaa gcgcgcggcc gcaaccacga cgccagcgcc gcgaccacca     780
acaccgcgc ccaccatcgc gtcgcagccc ctgtccctgc gcccagaggc gtgccggcca      840
gcggcgggg gcgcagtgca cacgagggg ctggacttcg cctgtgatat ctacatctgg       900
gcgcccttgg ccgggacttg tgggtcctt ctcctgtcac tggttatcac cctttactgc      960
aaacgggca gaaagaaact cctgtatata ttcaaacaac catttatgag accagtacaa     1020
actactcaag aggaagatgg ctgtagctgc cgatttccag aagaagaaga aggaggatgt     1080
gaactgagag tgaagttcag caggagcgca gacgcccccg cgtacaagca gggccagaac     1140
cagctctata cgagctcaa tctaggacga agagaggagt acgatgtttt ggacaagaga      1200
cgtggccggg accctgagat gggggggaaag ccgagaagga agaaccctca ggaaggcctg     1260
tacaatgaac tgcagaaaga taagatggcg gaggcctaca gtgagattgg gatgaaaggc     1320
gagcgccgga ggggcaaggg gcacgatggc ctttaccagg gtctcagtac agccaccaag     1380
gacacctacg acgcccttca catgcaggcc ctgccctc gctaa                       1425
```

<210> SEQ ID NO 136
<211> LENGTH: 1605
<212> TYPE: DNA
<213> ORGANISM: Artificial Sequence
<220> FEATURE:
<223> OTHER INFORMATION: Synthetic

<400> SEQUENCE: 136

```
caagtccagc tgcagcagtc aggagctgag gtgaagaagc ctggtagctc tgtcaaagtg      60
tcttgcaaag cctctggtgg tactttcagc tcttacgcca tttcttgggt gagacaggca     120
cccggacagg gtcttgaatg gatgggtgga atcatcccga ttcttgggat tgctaattac     180
gcacaaaagt tccagggaag ggtgaccatc accgcagacg aatctacctc cactgcttac     240
```

```
atggaactct cttccctgcg gtccgaggac accgccgtct actattgtgc caggggcggt      300
gccggaggaa gcggttctta ctatccgctg atttggggac aaggaaccac tgtgaccgtg      360
agctctggtg gaggcggatc cggtggtgga gggtccggag gcggaggatc tgagatcgtg      420
ctcactcaga gcccagccac ccttagcctg agccctggtg agcgcgccac cctctcatgc      480
ggtgcctcac agagcgtgag ctcaagctat ctggcatggt accagcaaaa gccagggcag      540
gccccgagcc tcctgatcta cgacgcatca tcacgggcta ccggtatccc ggcacgcttc      600
tctggaagcg gatcaggcac cgacttcacc ctgaccattt cttcacttga gccagaggac      660
tttgccgtgt actactgcca gcagcgctca agctggccgc ctacttggac tttcggacag      720
gggaccaagc tggagatcaa gcgcgcggcc gcattcgtgc cggtcttcct gccagcgaag      780
cccaccacga cgccagcgcc gcgaccacca acaccggcgc ccaccatcgc gtcgcagccc      840
ctgtccctgc gcccagaggc gtgccggcca gcggcggggg gcgcagtgca cacgaggggg      900
ctggacttcg cctgtgatat ctacatctgg gcgcccttgg ccgggacttg tgggtccttt      960
ctcctgtcac tggttatcac cctttactgc aaccacagga acaggagtaa gaggagcagg     1020
ctcctgcaca gtgactacat gaacatgact ccccgccgcc ccgggcccac ccgcaagcat     1080
taccagccct atgccccacc acgcgacttc gcagcctatc gctcccgttt ctctgttgtt     1140
aaacggggca gaaagaagct cctgtatata ttcaaacaac catttatgag accagtacaa     1200
actactcaag aggaagatgg ctgtagctgc cgatttccag aagaagaaga aggaggatgt     1260
gaactgagag tgaagttcag caggagcgca gacgcccccg cgtaccagca gggccagaac     1320
cagctctata acgagctcaa tctaggacga agagaggagt acgatgtttt ggacaagaga     1380
cgtggccggg accctgagat ggggggaaag ccgagaagga agaaccctca ggaaggcctg     1440
tacaatgaac tgcagaaaga taagatggcg gaggcctaca gtgagattgg gatgaaaggc     1500
gagcgccgga ggggcaaggg gcacgatggc ctttaccagg gtctcagtac agccaccaag     1560
gacacctacg acgcccttca catgcaggcc ctgccccctc gctaa                    1605
```

<210> SEQ ID NO 137
<211> LENGTH: 1395
<212> TYPE: DNA
<213> ORGANISM: Artificial Sequence
<220> FEATURE:
<223> OTHER INFORMATION: Synthetic

<400> SEQUENCE: 137

```
caagtccagc tggtgcaaag cggagcagaa gtgaagaagc ctggatcctc tgtgaaggtc       60
agctgcaagg cctctggagg taccttcagc tcttacgcaa tttcttgggt gcgccaggct      120
cccgggcagg gactggagtg gatgggagga atcatcccga tccttggtac cgctaattac      180
gcccagaaat tcagggtcgg ggtgaccatc accgcagacg agtcaacctc aaccgcttac      240
atggaacttt ctagcctccg cagcgaggac accgccgtct actattgcgc aagatggggt      300
ggtggtgcct tcgacatttg gggacaggac actatggtca ccgtgagctc cggtggagga      360
ggatctggcg gaggagggtc aggcggaggt gggtcagaga ttgtgctgac ccagtcaccc      420
gggactctgt ccctttctcc tggtgagcgc gctactctgt cttgtagggc ctcacaatca      480
gtgggcggct atctcgcctg gtatcagcag aaaccaggga aggcccctag gcttctcatc      540
tacgacgcct ccaaccgggc aactggcatt ccagcccgct tcagcggaag cggatccgga      600
accgacttta ctctgactat ctcctcactg gaaccgagga cttcgcagt gtactactgc       660 cagcagcgga ataactggcc accgatgtac actttcggac aggggaccaa gctggagatc      720
```

```
aagcgcgcgg ccgcaattga agttatgtat cctcctcctt acctagacaa tgagaagagc    780
aatggaacca ttatccatgt gaaagggaaa cacctttgtc caagtcccct atttcccgga    840
ccttctaagc ccttttgggt gctggtggtg gttgggggag tcctggcttg ctatagcttg    900
ctagtaacag tggcctttat tattttctgg gtgaggagta agaggagcag gctcctgcac    960
agtgactaca tgaacatgac tccccgccgc cccgggccca cccgcaagca ttaccagccc   1020
tatgccccac cacgcgactt cgcagcctat cgctccagag tgaagttcag caggagcgca   1080
gacgcccccg cgtaccagca gggccagaac cagctctata cgagctcaa tctaggacga   1140 agagaggagt acgatgtttt ggacaagaga cgtggccggg accctgagat ggggggaaag   1200
ccgagaagga agaaccctca ggaaggcctg tacaatgaac tgcagaaaga taagatggcg   1260
gaggcctaca gtgagattgg gatgaaaggc gagcgccgga ggggcaaggg gcacgatggc   1320
ctttaccagg gtctcagtac agccaccaag gacacctacg acgcccttca catgcaggcc   1380 ctgcccccctc gctaa                                                   1395
```

<210> SEQ ID NO 138
<211> LENGTH: 1407
<212> TYPE: DNA
<213> ORGANISM: Artificial Sequence
<220> FEATURE:
<223> OTHER INFORMATION: Synthetic

<400> SEQUENCE: 138

```
caagtccagc tggtgcaaag cggagcagaa gtgaagaagc ctggatcctc tgtgaaggtc     60
agctgcaagg cctctggagg taccttcagc tcttacgcaa tttcttgggt gcgccaggct    120
cccgggcagg gactggagtg gatgggagga atcatcccga tccttggtac cgctaattac    180
gcccagaaat tcagggtcg ggtgaccatc accgcagacg agtcaacctc aaccgcttac    240
atggaacttt ctagcctccg cagcgaggac accgccgtct actattgcgc aagatggggt    300
ggtggtgcct tcgacatttg gggacagggc actatggtca ccgtgagctc cggtggagga    360
ggatctggcg gaggagggtc aggcggaggt gggtcagaga ttgtgctgac ccagtcaccc    420
gggactctgt ccctttctcc tggtgagcgc gctactctgt cttgtagggc ctcacaatca    480
gtgggcggct atctcgcctg gtatcagcag aaaccagggc aggcccctag gcttctcatc    540
tacgacgcct ccaaccgggc aactggcatt ccagcccgct tcagcggaag cggatccgga    600
accgacttta ctctgactat ctcctcactg gaaccgagg acttcgcagt gtactactgc    660
cagcagcgga ataactggcc accgatgtac actttcggac aggggaccaa gctggagatc    720
aagcgcgcgg ccgcaaccac gacgccagcg ccgcgaccac caacaccggc gcccaccatc    780
gcgtcgcagc ccctgtccct gcgcccagag gcgtgccggc cagcggcggg gggcgcagtg    840
cacacgaggg ggctggactt cgcctgtgat atctacatct gggcgccctt ggccgggact    900
tgtggggtcc ttctcctgtc actggttatc acccttact gcaaacgggg cagaaagaaa    960
ctcctgtata tattcaaaca accatttatg agaccagtac aaactactca agaggaagat   1020
ggctgtagct gccgatttcc agaagaagaa gaaggaggat gtgaactgag agtgaagttc   1080
agcaggagcg cagacgcccc cgcgtacaag cagggccaga accagctcta taacgagctc   1140
aatctaggac gaagagagga gtacgatgtt ttggacaaga cgtggccg ggaccctgag    1200 atgggggaa agccgagaag gaagaaccct caggaaggcc tgtacaatga actgcagaaa   1260
gataagatgg cggaggccta cagtgagatt gggatgaaag gcgagcgccg gaggggcaag   1320
gggcacgatg gcctttacca gggtctcagt acagccacca aggacaccta cgacgccctt   1380
```

```
cacatgcagg ccctgccccc tcgctaa                                        1407

<210> SEQ ID NO 139
<211> LENGTH: 1587
<212> TYPE: DNA
<213> ORGANISM: Artificial Sequence
<220> FEATURE:
<223> OTHER INFORMATION: Synthetic

<400> SEQUENCE: 139
caagtccagc tggtgcaaag cggagcagaa gtgaagaagc tggatcctc tgtgaaggtc       60 agctgcaagg cctctggagg taccttcagc tcttacgcaa tttcttgggt gcgccaggct     120
cccgggcagg gactggagtg gatgggagga atcatcccga tccttggtac cgctaattac     180
gcccagaaat tcagggtcg ggtgaccatc accgcagacg agtcaacctc aaccgcttac     240 atgaacttt ctagcctccg cagcgaggac accgccgtct actattgcgc aagatggggt      300
ggtggtgcct tcgacatttg gggacagggc actatggtca ccgtgagctc cggtggagga     360
ggatctggcg gaggagggtc aggcggaggt gggtcagaga ttgtgctgac ccagtcaccc     420
gggactctgt ccctttctcc tggtgagcgc gctactctgt cttgtagggc ctcacaatca     480
gtgggcggct atctcgcctg gtatcagcag aaaccaggc aggcccctag gcttctcatc      540
tacgacgcct ccaaccgggc aactggcatt ccagcccgct tcagcggaag cggatccgga    600 accgactta ctctgactat ctcctcactg gaaccgagg acttcgcagt gtactactgc       660
cagcagcgga taactggcc accgatgtac actttcggac aggggaccaa gctggagatc     720
aagcgcgcgg ccgcattcgt gccggtcttc ctgccagcga agccaccac gacgccagcg     780 ccgcgaccac caacaccggc gcccaccatc gcgtcgcagc ccctgtccct gcgcccagag    840
gcgtgccggc cagcggcggg gggcgcagtg cacacgaggg gctggacttt cgcctgtgat    900
atctacatct gggcgccctt ggcgggact tgtggggtcc ttctcctgtc actggttatc     960
accctttact gcaaccacag gaacaggagt aagaggagca ggctcctgca cagtgactac    1020
atgaacatga ctccccgccg ccccgggccc accgcaagc attaccagcc ctatgcccca    1080
ccacgcgact tcgcagccta tcgctcccgt ttctctgttg ttaaacgggg cagaaagaag    1140
ctcctgtata tattcaaaca accatttatg agaccagtac aaactactca agaggaagat    1200
ggctgtagct gccgatttcc agaagaagaa gaaggaggat gtgaactgag agtgaagttc    1260
agcaggagcg cagacgcccc cgcgtaccag cagggccaga accagctcta taacgagctc    1320
aatctaggac gaagagagga gtacgatgtt ttggacaaga gacgtggccg ggaccctgag    1380 atgggggaa agccgagaag gaagaaccct caggaaggcc tgtacaatga actgcagaaa    1440
gataagatgg cggaggccta cagtgagatt gggatgaaag gcgagcgccg gaggggcaag    1500
gggcacgatg gcctttacca gggtctcagt acagccacca aggacaccta cgacgccctt    1560
cacatgcagg ccctgccccc tcgctaa                                        1587

<210> SEQ ID NO 140
<211> LENGTH: 72
<212> TYPE: DNA
<213> ORGANISM: Artificial Sequence
<220> FEATURE:
<223> OTHER INFORMATION: Synthetic

<400> SEQUENCE: 140
atggttctgc tggtgacttc actcctgctc tgtgaacttc cccatcccgc ttttctcctg       60
atccccgaca cc                                                         72
```

ANTI-CD276 POLYPEPTIDES, PROTEINS, AND CHIMERIC ANTIGEN RECEPTORS

CROSS-REFERENCE TO RELATED APPLICATION

This application is a continuation application of U.S. patent application Ser. No. 14/779,586, filed on Sep. 24, 2015, now U.S. Pat. No. 9,790,282, issued Oct. 17, 2017, which is the National Stage of International Application No. PCT/US2014/031543, filed on Mar. 24, 2014, which claims the benefit of U.S. Provisional Patent Application No. 61/805,001, filed Mar. 25, 2013. The entire contents of the above patent documents are incorporated by reference as if recited in full herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: one 207 KB ASCII (Text) file named "0389259con_ST25.txt", dated Sep. 8, 2017.

BACKGROUND OF THE INVENTION

Cancer is a public health concern. Despite advances in treatments such as chemotherapy, the prognosis for many cancers, including solid tumors, may be poor. It is estimated that about 559,650 Americans will die from cancer, corresponding to 1,500 deaths per day (Jemal et al., *CA Cancer J. Clin.*, 57:43-66 (2007)). Accordingly, there exists an unmet need for additional treatments for cancer, particularly solid tumors.

BRIEF SUMMARY OF THE INVENTION

An embodiment of the invention provides a polypeptide comprising (i) SEQ ID NOs: 1-6, (ii) SEQ ID NOs: 11-16, or (iii) SEQ ID NOs: 20-25.

Another embodiment of the invention provides a protein comprising a first polypeptide chain comprising (i) SEQ ID NOs: 1-3, (ii) SEQ ID NOs: 11-13, or (iii) SEQ ID NOs: 20-22 and a second polypeptide chain comprising (i) SEQ ID NOs: 4-6, (ii) SEQ ID NOs: 14-16, or (iii) SEQ ID NOs: 23-25.

Further embodiments of the invention provide related chimeric antigen receptors (CARs), anti-CD276 binding moieties, nucleic acids, recombinant expression vectors, host cells, populations of cells, conjugates, and pharmaceutical compositions relating to the polypeptides and proteins of the invention.

Additional embodiments of the invention provide methods of detecting the presence of cancer in a mammal and methods of treating or preventing cancer in a mammal.

DETAILED DESCRIPTION OF THE INVENTION

Figure 1:
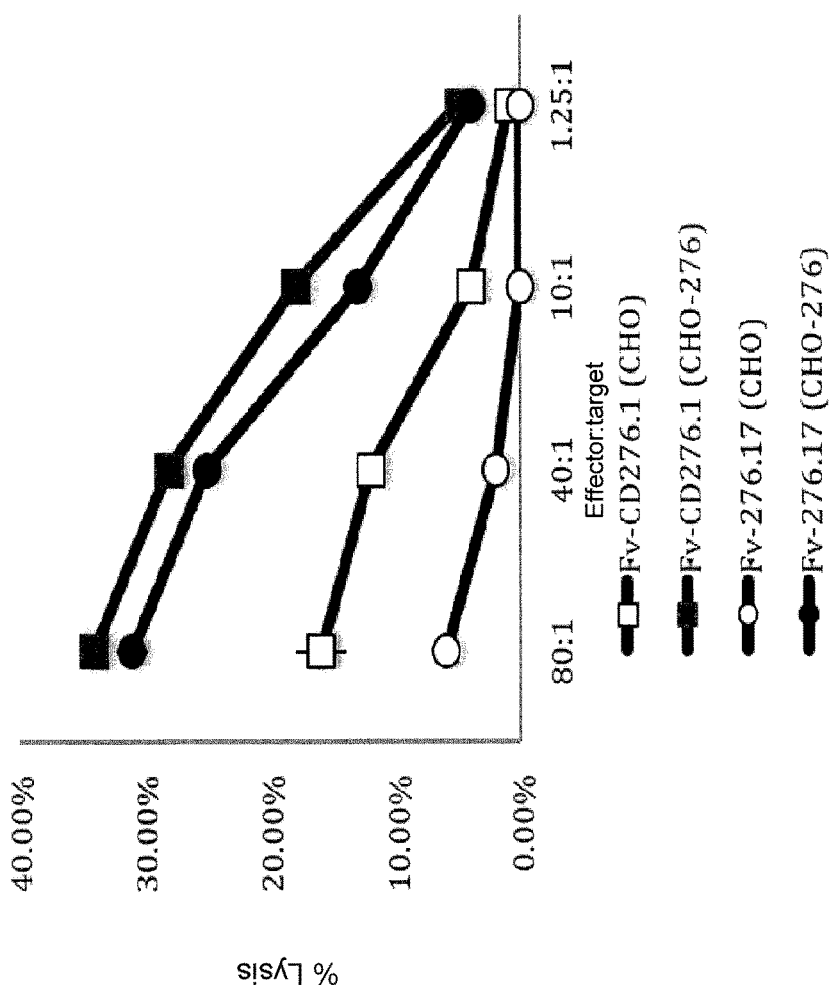
FIG. 1 is a graph showing percent lysis of target $^{51}$Cr labeled CHO or CHO-276 cells by effector human T cells transduced with a nucleotide sequence encoding a CAR comprising SEQ ID NO: 42 (CD276.1 second generation, version 1) or a CAR comprising SEQ ID NO: 45 (CD276.17 second generation, version 1) at various effector to target ratio (E:T) ratios. Open squares represent percent lysis of target CHO cells co-cultured with cells expressing SEQ ID NO: 42 (CD276.1 second generation, version 1), closed squares represent percent lysis of target CHO-276 cells co-cultured with cells expressing SEQ ID NO: 42 (CD276.1 second generation, version 1), open circles represent percent lysis of target CHO cells co-cultured with cells expressing SEQ ID NO: 45 (CD276.17 second generation, version 1), and closed circles represent percent lysis of target CHO-276 cells co-cultured with cells expressing SEQ ID NO: 45 (CD276.17 second generation, version 1) at the indicated effector to target ratio (E:T) ratios.

An embodiment of the invention provides polypeptides and proteins comprising an antigen binding domain of an anti-CD276 antibody. The polypeptides and proteins advantageously specifically recognize and bind to CD276 (also known as B7-H3). CD276 is expressed or overexpressed on a variety of human tumors, including pediatric solid tumors and adult carcinomas. Examples of cancers that express or overexpress CD276 include, but are not limited to, neuroblastoma, Ewing's sarcoma, rhabdomyosarcoma, and prostate, ovarian, colorectal, and lung cancers. Without being bound to a particular theory or mechanism, it is believed that by specifically recognizing and binding to CD276, the inventive polypeptides and proteins may, advantageously, target CD276-expressing cancer cells. In an embodiment of the invention, the inventive polypeptides and proteins may elicit an antigen-specific response against CD276. Accordingly, without being bound to a particular theory or mechanism, it is believed that by eliciting an antigen-specific response against CD276, the inventive proteins and polypeptides may provide for one or more of the following: targeting and destroying CD276-expressing cancer cells, reducing or eliminating cancer cells, facilitating infiltration of immune cells and/or effector molecules to tumor site(s), and enhancing/extending anti-cancer responses.

The term "polypeptide" as used herein includes oligopeptides and refers to a single chain of amino acids connected by one or more peptide bonds. The polypeptide may comprise one or more variable regions (e.g., two variable regions) of an antigen binding domain of an anti-CD276 antibody, each variable region comprising a complementarity determining region (CDR) 1, a CDR2, and a CDR3. Preferably, a first variable region comprises a CDR1 comprising the amino acid sequence of SEQ ID NO: 1, 11, or 20 (CDR1 of first variable region), a CDR2 comprising the amino acid sequence of SEQ ID NO: 2, 12, or 21 (CDR2 of first variable region), and a CDR3 comprising the amino acid sequence of SEQ ID NO: 3, 13, or 22 (CDR3 of first variable region), and the second variable region comprises a CDR1 comprising the amino acid sequence of SEQ ID NO: 4, 14, or 23 (CDR1 of second variable region), a CDR2 comprising the amino acid sequence of SEQ ID NO: 5, 15, or 24 (CDR2 of second variable region), and a CDR3 comprising the amino acid sequence of SEQ ID NO: 6, 16, or 25 (CDR3 of second variable region). In this regard, the inventive polypeptide can comprise SEQ ID NOs: 1-3, 4-6, 11-13, 14-16, 20-22, 23-25, 1-6, 11-16, or 20-25. Accordingly, an embodiment of the invention provides a polypeptide comprising (i) SEQ ID NOs: 1-6, (ii) SEQ ID NOs: 11-16, or (iii) SEQ ID NOs: 20-25. Preferably, the polypeptide comprises the amino acid sequences of SEQ ID NOs: 20-25.

In an embodiment, the polypeptides each comprise one or more variable regions (e.g., first and second variable regions) of an antigen binding domain of an anti-CD276 antibody, each comprising the CDRs as described above. The first variable region may comprise SEQ ID NO: 8, 18, or 27. The second variable region may comprise SEQ ID NO: 7, 17, or 26. Accordingly, in an embodiment of the invention, the polypeptide comprises SEQ ID NO: 7, SEQ ID NO: 8, SEQ ID NO: 17, SEQ ID NO: 18, SEQ ID NO: 26, SEQ ID NO: 27, SEQ ID NOs: 7 and 8, SEQ ID NOs: 17 and 18, or SEQ ID NOs: 26 and 27. Preferably, the polypeptide comprises SEQ ID NOs: 26 and 27.

In an embodiment of the invention, the variable regions of the polypeptide may be joined by a linker. The linker may comprise any suitable amino acid sequence. In an embodiment of the invention, the linker may comprise SEQ ID NO: 9 or 115.

In an embodiment of the invention, the polypeptide comprises two variable regions, each comprising the CDRs as described above, with a linker positioned between the two variable regions. In this regard, the polypeptide may comprise SEQ ID NOs: 10, 19, or 28.

In an embodiment, the polypeptide comprises a leader sequence. The leader sequence may be positioned at the amino terminus of the light chain variable region. The leader sequence may comprise any suitable leader sequence. In an embodiment, the leader sequence is a human granulocyte-macrophage colony-stimulating factor (GM-CSF) receptor sequence. The leader sequence may comprise, for example, SEQ ID NO: 60, 61, or 62. In an embodiment of the invention, while the leader sequence may facilitate expression of the polypeptide on the surface of the cell, the presence of the leader sequence in an expressed polypeptide is not necessary in order for the polypeptide to function. In an embodiment of the invention, upon expression of the polypeptide on the cell surface, the leader sequence may be cleaved off of the polypeptide. Accordingly, in an embodiment of the invention, the polypeptide lacks a leader sequence.

The invention further provides a protein comprising at least one of the polypeptides described herein. By "protein" is meant a molecule comprising one or more polypeptide chains.

The protein of the invention can comprise a first polypeptide chain comprising the amino acid sequences of (i) SEQ ID NOs: 1-3, (ii) SEQ ID NOs: 11-13, or (iii) SEQ ID NOs: 20-22 and a second polypeptide chain comprising (i) SEQ ID NOs: 4-6, (ii) SEQ ID NOs: 14-16, or (iii) SEQ ID NOs: 23-25. The protein of the invention can, for example, comprise a first polypeptide chain comprising the amino acid sequence of SEQ ID NO: 7, 17, or 26 and a second polypeptide chain comprising the amino acid sequence of SEQ ID NO: 8, 18, or 27. In this regard, the protein may comprise a first polypeptide chain comprising SEQ ID NO: 7, 17, or 26 and a second polypeptide chain comprising SEQ ID NO: 8, 18, or 27.

The protein may further comprise a leader sequence and/or a linker as described herein with respect to other aspects of the invention. In an embodiment, the protein lacks a leader sequence.

The protein of the invention can be, for example, a fusion protein. If, for example, the protein comprises a single polypeptide chain comprising (i) SEQ ID NO: 7, 17, or 26 and (ii) SEQ ID NO: 8, 18, or 27, or if the first and/or second polypeptide chain(s) of the protein further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods. See, for instance, Choi et al., *Mol. Biotechnol.* 31: 193-202 (2005).

It is contemplated that the polypeptides and proteins of the invention may be useful as anti-CD276 binding moieties. In this regard, an embodiment of the invention provides an anti-CD276 binding moiety comprising any of the polypeptides or proteins described herein. In an embodiment of the invention, the anti-CD276 binding moiety comprises an antigen binding portion of any of the polypeptides or proteins described herein. The antigen binding portion can be any portion that has at least one antigen binding site. In an embodiment, the anti-CD276 binding moiety is a Fab fragment (Fab), F(ab')$_2$ fragment, diabody, triabody, tetrabody, single-chain variable region fragment (scFv), or disulfide-stabilized variable region fragment (dsFv).

In an embodiment, the anti-CD276 binding moiety can be an antibody. The antibody may be, for example, a recombinant antibody comprising at least one of the inventive polypeptides described herein. As used herein, "recombinant antibody" refers to a recombinant (e.g., genetically engineered) protein comprising at least one of the polypeptides or proteins of the invention and one or more polypeptide chains of an antibody, or a portion thereof. The polypeptide of an antibody, or portion thereof, can be, for example, a constant region of a heavy or light chain, or an Fc fragment of an antibody, etc. The polypeptide chain of an antibody, or portion thereof, can exist as a separate polypeptide of the recombinant antibody. Alternatively, the polypeptide chain of an antibody, or portion thereof, can exist as a polypeptide, which is expressed in frame (in tandem) with the polypeptide or protein of the invention. The polypeptide of an antibody, or portion thereof, can be a polypeptide of any antibody or any antibody fragment.

The antibody of the invention can be any type of immunoglobulin that is known in the art. For instance, the anti-CD276 binding moiety can be an antibody of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for CD276.

Methods of testing antibodies for the ability to bind to CD276 are known in the art and include any antibody-antigen binding assay, such as, for example, radioimmunoassay (RIA), ELISA, Western blot, immunoprecipitation, and competitive inhibition assays (see, e.g., Murphy et al., infra, and U.S. Patent Application Publication No. 2002/0197266 A1).

Suitable methods of making antibodies are known in the art. For instance, standard hybridoma methods are described in, e.g., Köhler and Milstein, *Eur. J. Immunol.*, 5, 511-519 (1976), Harlow and Lane (eds.), *Antibodies: A Laboratory Manual*, CSH Press (1988), and Murphy et al. (eds.), *Murphy's Immunobiology*, 7$^{th}$ Ed., Garland Science, New York, N.Y. (2008)). Alternatively, other methods, such as EBV-hybridoma methods (Haskard and Archer, *J. Immunol. Methods*, 74 (2), 361-67 (1984), and Roder et al., *Methods Enzymol.*, 121, 140-67 (1986)), and bacteriophage vector expression systems (see, e.g., Huse et al., *Science*, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1.

Phage display furthermore can be used to generate an antibody. In this regard, phage libraries encoding antigen-binding variable (V) domains of antibodies can be generated using standard molecular biology and recombinant DNA techniques. See, for instance, Green et al. (eds.), *Molecular Cloning, A Laboratory Manual*, 4$^{th}$ Edition, Cold Spring Harbor Laboratory Press, New York (2012) and Ausubel et al., *Current Protocols in Molecular Biology*, Greene Publishing Associates and John Wiley & Sons, NY (2007). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Murphy et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Murphy et al., supra.

Methods for generating humanized antibodies are well known in the art and are described in detail in, for example, Murphy et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., *J. Mol. Biol.*, 235, 959-973 (1994).

In a preferred embodiment, the anti-CD276 binding moiety is a single-chain variable region fragment (scFv). A single-chain variable region fragment (scFv) antibody fragment, which is a truncated Fab fragment including the variable (V) domain of an antibody heavy chain linked to a V domain of a light antibody chain via a synthetic peptide, can be generated using routine recombinant DNA technology techniques (see, e.g., Murphy et al., supra). Similarly, disulfide-stabilized variable region fragments (dsFv) can be prepared by recombinant DNA technology (see, e.g., Reiter et al., *Protein Engineering*, 7, 697-704 (1994)). The anti-CD276 binding moieties of the invention, however, are not limited to these exemplary types of antibody fragments.

Also, the anti-CD276 binding moiety can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

Another embodiment of the invention provides chimeric antigen receptors (CARs) comprising: (a) an antigen binding domain comprising any of the polypeptides or proteins described herein, (b) a transmembrane domain, and (c) an intracellular T cell signaling domain.

A chimeric antigen receptor (CAR) is an artificially constructed hybrid protein or polypeptide containing the antigen binding domains of an antibody (e.g., single chain variable fragment (scFv)) linked to T-cell signaling domains. Characteristics of CARs include their ability to redirect T-cell specificity and reactivity toward a selected target in a non-MHC-restricted manner, exploiting the antigen-binding properties of monoclonal antibodies. The non-MHC-restricted antigen recognition gives cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

The phrases "have antigen specificity" and "elicit antigen-specific response" as used herein means that the CAR can specifically bind to and immunologically recognize an antigen, such that binding of the CAR to the antigen elicits an immune response.

The CARs of the invention have antigen specificity for CD276 (also known as B7-H3). Without being bound to a particular theory or mechanism, it is believed that by eliciting an antigen-specific response against CD276, the inventive CARs provide for one or more of the following: targeting and destroying CD276-expressing cancer cells, reducing or eliminating cancer cells, facilitating infiltration of immune cells to tumor site(s), and enhancing/extending anti-cancer responses.

An embodiment of the invention provides a CAR comprising an antigen binding domain of an anti-CD276 antibody. The antigen binding domain of the anti-CD276 antibody specifically binds to CD276. The antigen binding domain of the CARs may comprise any of the polypeptides or proteins described herein. In an embodiment of the invention, the CAR comprises an anti-CD276 single chain variable fragment (scFv). In this regard, a preferred embodiment of the invention provides CARs comprising an antigen-binding domain comprising a single chain variable fragment (scFv) that comprises any of the polypeptides or proteins described herein.

In a preferred embodiment of the invention, the CAR comprises a heavy chain and a light chain each of which comprises a variable region comprising a complementarity determining region (CDR) 1, a CDR2, and a CDR3. Preferably, the heavy chain comprises a CDR1 comprising the amino acid sequence of SEQ ID NO: 1, 11, or 20 (CDR1 of heavy chain), a CDR2 comprising the amino acid sequence of SEQ ID NO: 2, 12, or 21 (CDR2 of heavy chain), and a CDR3 comprising the amino acid sequence of SEQ ID NO: 3, 13, or 22 (CDR3 of heavy chain), and the light chain comprises a CDR1 comprising the amino acid sequence of SEQ ID NO: 4, 14, or 23 (CDR1 of light chain), a CDR2 comprising the amino acid sequence of SEQ ID NO: 5, 15, or 24 (CDR2 of light chain), and a CDR3 comprising the amino acid sequence of SEQ ID NO: 6, 16, or 25 (CDR3 of light chain). In this regard, the inventive CAR can comprise SEQ ID NOs: 1-3, 4-6, 11-13, 14-16, 20-22, 23-25, 1-6, 11-16, or 20-25. Preferably the CAR comprises the amino acid sequences of SEQ ID NOs: 20-25.

The antigen binding domains of the CARs each comprise a light chain and a heavy chain. The light chain may comprise SEQ ID NO: 8, 18, or 27. The heavy chain may comprise SEQ ID NO: 7, 17, or 26. Accordingly, in an embodiment of the invention, the antigen binding domain comprises SEQ ID NO: 7, SEQ ID NO: 8, SEQ ID NO: 17, SEQ ID NO: 18, SEQ ID NO: 26, SEQ ID NO: 27, SEQ ID NOs: 7 and 8, SEQ ID NOs: 17 and 18, or SEQ ID NOs: 26 and 27. Preferably, the CAR comprises SEQ ID NOs: 26 and 27.

In an embodiment of the invention, the antigen binding domain of the CAR comprises a light chain and a heavy chain, each comprising the CDRs as described above, with a linker positioned between the light chain and the heavy chain. The linker may be as described herein with respect to other aspects of the invention. In this regard, the CAR may comprise SEQ ID NOs: 10, 19, or 28.

In an embodiment, the antigen binding domain of the CAR comprises a leader sequence. The leader sequence may be as described herein with respect to other aspects of the invention. In an embodiment of the invention, the CAR lacks a leader sequence.

In an embodiment, the CAR comprises an immunoglobulin constant domain. Preferably, the immunoglobulin domain is a human immunoglobulin sequence. In an embodiment, the immunoglobulin constant domain comprises an immunoglobulin CH2 and CH3 immunoglobulin G (IgG1) domain sequence (CH2CH3). In this regard, the CAR may comprise an immunoglobulin constant domain comprising SEQ ID NO: 71. In an embodiment of the invention, the CAR may comprise an amino acid sequence encoding an antigen binding domain and an immunoglobulin constant domain comprising any one of SEQ ID NOs: 80, 82, and 84. Without being bound to a particular theory, it is believed that the CH2CH3 domain extends the binding motif of the scFv away from the membrane of the CAR-expressing cells and may more accurately mimic the size and domain structure of a native TCR. In some embodiments, the CAR may lack an immunoglobulin constant domain.

In an embodiment of the invention, the CAR comprises a transmembrane domain. In an embodiment of the invention, the transmembrane domain comprises i) CD8 and/or ii) CD28. In a preferred embodiment, the CD8 and CD28 are human. The CD8 or CD28 may comprise less than the whole CD8 or CD28, respectively. In this regard, the CAR comprises a transmembrane domain comprising any one or more of a CD8 amino acid sequence comprising SEQ ID NO: 29, a CD28 amino acid sequence comprising SEQ ID NO: 30, and a CD8 amino acid sequence comprising SEQ ID NO: 31.

In an embodiment of the invention, the CAR comprises an intracellular T cell signaling domain comprising one or more of i) CD28, ii) CD137, and iii) CD3 zeta (ζ). In a preferred embodiment, the one or more of CD28, CD137, and CD3 zeta are human. CD28 is a T cell marker important in T cell co-stimulation. CD137, also known as 4-1BB, transmits a potent costimulatory signal to T cells, promoting differentiation and enhancing long-term survival of T lymphocytes. CD3ζ associates with TCRs to produce a signal and contains immunoreceptor tyrosine-based activation motifs (ITAMs). One or more of CD28, CD137, and CD3 zeta may comprise less than the whole CD28, CD137, or CD3 zeta, respectively. In an embodiment of the invention, intracellular T cell signaling domain comprises a CD28 amino acid sequence comprising SEQ ID NO: 32 and/or SEQ ID NO: 35. In another embodiment of the invention, the intracellular T cell signaling domain comprises a CD137 amino acid sequence comprising SEQ ID NO: 33 and/or SEQ ID NO: 37. In another embodiment of the invention, the intracellular T cell signaling domain comprises a CD3 zeta amino acid sequence comprising any one or more of SEQ ID NOs: 34, 36, and 38.

In an embodiment of the invention, the CAR comprises a transmembrane domain comprising CD28 and an intracellular T cell signaling domain comprising CD28 and CD3 zeta. In this regard, the CAR may comprise each of SEQ ID NOs: 30, 35, and 36. In an embodiment, a transmembrane domain comprising CD28 and an intracellular T cell signaling domain comprising CD28 and CD3 zeta comprises SEQ ID NO: 73. Preferably, the CAR comprises (a) each of SEQ ID NOs: 1-6, 71, 30, 35, and 36; (b) each of SEQ ID NOs: 7, 8, 71, 30, 35, and 36; (c) each of SEQ ID NOs: 10, 71, 30, 35, and 36; (d) each of SEQ ID NOs: 11-16, 71, 30, 35, and 36; (e) each of SEQ ID NOs: 17, 18, 71, 30, 35, and 36; (f) each of SEQ ID NOs: 19, 71, 30, 35, and 36; (g) each of SEQ ID NOs: 20-25, 71, 30, 35, and 36; (h) each of SEQ ID NOs: 26, 27, 71, 30, 35, and 36; or (i) each of SEQ ID NOs: 28, 71, 30, 35, and 36.

In an embodiment of the invention, the CAR comprises a transmembrane domain comprising CD8 and an intracellular T cell signaling domain comprising CD28, CD137, and CD3 zeta. In this regard, the CAR may comprise each of SEQ ID NOs: 29 and 32-34. In an embodiment, a transmembrane domain comprising CD8 and an intracellular T cell signaling domain comprising CD28, CD137, and CD3 zeta comprises SEQ ID NO: 75. Preferably, the CAR comprises (a) each of SEQ ID NOs: 1-6, 71, 29, and 32-34; (b) each of SEQ ID NOs: 7, 8, 71, 29, and 32-34; (c) each of SEQ ID NOs: 10, 71, 29, and 32-34; (d) each of SEQ ID NOs: 11-16, 71, 29, and 32-34; (e) each of SEQ ID NOs: 17, 18, 71, 29, and 32-34; (f) each of SEQ ID NOs: 19, 71, 29, and 32-34; (g) each of SEQ ID NOs: 20-25, 71, 29, and 32-34; (h) each of SEQ ID NOs: 26, 27, 71, 29, and 32-34; or (i) each of SEQ ID NOs: 28, 71, 29, and 32-34.

In an embodiment of the invention, the CAR comprises a transmembrane domain comprising CD8 and an intracellular T cell signaling domain comprising CD137 and CD3 zeta. In this regard, the CAR may comprise each of SEQ ID NOs: 31, 37, and 38. In an embodiment, a transmembrane domain comprising CD8 and an intracellular T cell signaling domain comprising CD137 and CD3 zeta comprises SEQ ID NO: 74. Preferably, the CAR comprises each of (a) each of SEQ ID NOs: 1-6, 71, 31, 37, and 38; (b) each of SEQ ID NOs: 7, 8, 71, 31, 37, and 38; (c) each of SEQ ID NOs: 10, 71, 31, 37, and 38; (d) each of SEQ ID NOs: 11-16, 71, 31, 37, and 38; (e) each of SEQ ID NOs: 17, 18, 71, 31, 37, and 38; (f) each of SEQ ID NOs: 19, 71, 31, 37, and 38; (g) each of SEQ ID NOs: 20-25, 71, 31, 37, and 38; (h) each of SEQ ID NOs: 26, 27, 71, 31, 37, and 38; or (i) each of SEQ ID NOs: 28, 71, 31, 37, and 38.

Additional embodiments of the invention provide CARs comprising one or more of any of the amino acid sequences set forth in Tables 1A and 1B.

TABLE 1A

| SEQ ID NO: | Antigen Binding Domain | Further Components |
|---|---|---|
| SEQ ID NO: 39 (CD276.6 CAR-second generation, version 1) | CD276.6 scFv (SEQ ID NO: 10) | CH2CH3 CD28 transmembrane domain CD28 and CD3ζ intracellular T cell signaling domains |
| SEQ ID NO: 40 (CD276.6 CAR-second generation, version 2) | CD276.6 scFv (SEQ ID NO: 10) | CH2CH3 CD8 transmembrane domain CD137 and CD3ζ intracellular T cell signaling domains |
| SEQ ID NO: 41 (CD276.6 CAR-third generation) | CD276.6 scFv (SEQ ID NO: 10) | CH2CH3 CD8 transmembrane domain CD28, CD137, and CD3ζ intracellular T cell signaling domains |
| SEQ ID NO: 42 (CD276.1 CAR-second generation, version 1) | CD276.1 scFv (SEQ ID NO: 19) | CH2CH3 CD28 transmembrane domain CD28 and CD3ζ intracellular T cell signaling domains |
| SEQ ID NO: 43 (CD276.1 CAR-second generation, version 2) | CD276.1 scFv (SEQ ID NO: 19) | CH2CH3 CD8 transmembrane domain CD137 and CD3ζ intracellular T cell signaling domains |
| SEQ ID NO: 44 (CD276.1 CAR-third generation) | CD276.1 scFv (SEQ ID NO: 19) | CH2CH3 CD8 transmembrane domain CD28, CD137, and CD3ζ intracellular T cell signaling domains |
| SEQ ID NO: 45 (CD276.17 CAR-second generation, version 1) | CD276.17 scFv (SEQ ID NO: 28) | CH2CH3 CD28 transmembrane domain CD28 and CD3ζ intracellular T cell signaling domains |
| SEQ ID NO: 46 (CD276.17 CAR-second generation, version 2) | CD276.17 scFv (SEQ ID NO: 28) | CH2CH3 CD8 transmembrane domain CD137 and CD3ζ intracellular T cell signaling domains |
| SEQ ID NO: 47 (CD276.17 CAR-third generation) | CD276.17 scFv (SEQ ID NO: 28) | CH2CH3 CD8 transmembrane domain CD28, CD137, and CD3ζ intracellular T cell signaling domains |

TABLE 1B

| SEQ ID NO: | Antigen Binding Domain | Further Components |
|---|---|---|
| SEQ ID NO: 122 (CD276.6 CAR-second generation, version 1) | CD276.6 scFv (SEQ ID NO: 10) | CD28 transmembrane domain CD28 and CD3ζ intracellular T cell signaling domains |
| SEQ ID NO: 123 (CD276.6 CAR-second generation, version 2) | CD276.6 scFv (SEQ ID NO: 10) | CD8 transmembrane domain CD137 and CD3ζ intracellular T cell signaling domains |
| SEQ ID NO: 124 (CD276.6 CAR-third generation) | CD276.6 scFv (SEQ ID NO: 10) | CD8 transmembrane domain CD28, CD137, and CD3ζ intracellular T cell signaling domains |
| SEQ ID NO: 125 (CD276.1 CAR-second generation, version 1) | CD276.1 scFv (SEQ ID NO: 19) | CD28 transmembrane domain CD28 and CD3ζ intracellular T cell signaling domains |
| SEQ ID NO: 126 (CD276.1 CAR-second generation, version 2) | CD276.1 scFv (SEQ ID NO: 19) | CD8 transmembrane domain CD137 and CD3ζ intracellular T cell signaling domains |
| SEQ ID NO: 127 (CD276.1 CAR-third generation) | CD276.1 scFv (SEQ ID NO: 19) | CD8 transmembrane domain CD28, CD137, and CD3ζ intracellular T cell signaling domains |
| SEQ ID NO: 128 (CD276.17 CAR-second generation, version 1) | CD276.17 scFv (SEQ ID NO: 28) | CD28 transmembrane domain CD28 and CD3ζ intracellular T cell signaling domains |
| SEQ ID NO: 129 (CD276.17 CAR-second generation, version 2) | CD276.17 scFv (SEQ ID NO: 28) | CD8 transmembrane domain CD137 and CD3ζ intracellular T cell signaling domains |
| SEQ ID NO: 130 (CD276.17 CAR-third generation) | CD276.17 scFv (SEQ ID NO: 28) | CD8 transmembrane domain CD28, CD137, and CD3ζ intracellular T cell signaling domains |

Included in the scope of the invention are functional portions of the inventive polypeptides, proteins, and CARs described herein. The term "functional portion" when used in reference to a polypeptide, protein, or CAR refers to any part or fragment of the polypeptide, protein, or CAR of the invention, which part or fragment retains the biological activity of the polypeptide, protein, or CAR of which it is a part (the parent polypeptide, protein, or CAR). Functional portions encompass, for example, those parts of a polypeptide, protein, or CAR that retain the ability to recognize target cells, or detect, treat, or prevent a disease, to a similar extent, the same extent, or to a higher extent, as the parent polypeptide, protein, or CAR. In reference to the parent polypeptide, protein, or CAR, the functional portion can comprise, for instance, about 10%, 25%, 30%, 50%, 68%, 80%, 90%, 95%, or more, of the parent polypeptide, protein, or CAR.

The functional portion can comprise additional amino acids at the amino or carboxy terminus of the portion, or at both termini, which additional amino acids are not found in the amino acid sequence of the parent polypeptide, protein, or CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent polypeptide, protein, or CAR.

Included in the scope of the invention are functional variants of the inventive polypeptides, proteins, or CARs described herein. The term "functional variant" as used herein refers to a polypeptide, protein, or CAR having substantial or significant sequence identity or similarity to a parent polypeptide, protein, or CAR, which functional variant retains the biological activity of the polypeptide, protein, or CAR of which it is a variant. Functional variants encompass, for example, those variants of the polypeptide, protein, or CAR described herein (the parent polypeptide, protein, or CAR) that retain the ability to recognize target cells to a similar extent, the same extent, or to a higher extent, as the parent polypeptide, protein, or CAR. In reference to the parent polypeptide, protein, or CAR, the functional variant can, for instance, be at least about 30%, about 50%, about 75%, about 80%, about 85%, about 90%, about 91%, about 92%, about 93%, about 94%, about 95%, about 96%, about 97%, about 98%, about 99% or more identical in amino acid sequence to the parent polypeptide, protein, or CAR.

A functional variant can, for example, comprise the amino acid sequence of the parent polypeptide, protein, or CAR with at least one conservative amino acid substitution. Alternatively or additionally, the functional variants can comprise the amino acid sequence of the parent polypeptide, protein, or CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent polypeptide, protein, or CAR.

Amino acid substitutions of the inventive polypeptides, proteins, or CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gln, Ser, Thr, Tyr, etc.), an amino acid with a beta-branched side-chain substituted for another amino acid with a beta-branched side-chain (e.g., Ile, Thr, and Val), an amino acid with an aromatic side-chain substituted for another amino acid with an aromatic side chain (e.g., His, Phe, Trp, and Tyr), etc.

The polypeptide, protein, or CAR can consist essentially of the specified amino acid sequence or sequences described herein, such that other components, e.g., other amino acids, do not materially change the biological activity of the polypeptide, protein, CAR, functional portion, or functional variant.

The polypeptides, proteins, or CARs of embodiments of the invention (including functional portions and functional variants) can be of any length, i.e., can comprise any number of amino acids, provided that the polypeptides, proteins, or CARs (or functional portions or functional variants thereof) retain their biological activity, e.g., the ability to specifically bind to antigen, detect diseased cells in a mammal, or treat or prevent disease in a mammal, etc. For example, the polypeptide, protein, or CAR can be about 50 to about 5000 amino acids long, such as 50, 70, 75, 100, 125, 150, 175, 200, 300, 400, 500, 600, 700, 800, 900, 1000 or more amino acids in length.

The polypeptides, proteins, or CARs of embodiments of the invention (including functional portions and functional variants of the invention) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The polypeptides, proteins, or CARs of embodiments of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized.

The polypeptides, proteins, or CARs of embodiments of the invention (including functional portions and functional variants thereof) can be obtained by methods known in the art. The polypeptides, proteins, or CARs may be made by any suitable method of making polypeptides or proteins. Suitable methods of de novo synthesizing polypeptides and proteins are described in references, such as Chan et al., *Fmoc Solid Phase Peptide Synthesis*, Oxford University Press, Oxford, United Kingdom, 2000; *Peptide and Protein Drug Analysis*, ed. Reid, R., Marcel Dekker, Inc., 2000; *Epitope Mapping*, ed. Westwood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, e.g., Green et al., supra, and Ausubel et al., supra. Further, some of the polypeptides, proteins, or CARs of the invention (including functional portions and functional variants thereof) can be isolated and/or purified from a source, such as a plant, a bacterium, an insect, a mammal, e.g., a rat, a human, etc. Methods of isolation and purification are well-known in the art. Alternatively, the polypeptides, proteins, or CARs described herein (including functional portions and functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive polypeptides, proteins, or CARs can be synthetic, recombinant, isolated, and/or purified.

Included in the scope of the invention are conjugates, e.g., bioconjugates, comprising any of the inventive polypeptides, proteins, CARs, anti-CD276 binding moieties, conjugates, or functional portions or functional variants thereof. Conjugates, as well as methods of synthesizing conjugates in general, are known in the art (See, for instance, Hudecz, F., *Methods Mol. Biol.* 298: 209-223 (2005) and Kirin et al., *Inorg Chem.* 44 (15): 5405-5415 (2005)). In this regard, an embodiment of the invention provides a conjugate comprising (a) any of the polypeptides, proteins, CARs, anti-CD276 binding moieties described herein conjugated to (b) an effector molecule. The effector molecule may be any therapeutic molecule or a molecule that facilitates the detection of the conjugate. The effector molecule is not limited and may be any suitable effector molecule. For example, the effector molecule may be any one or more of a drug, toxin, label (e.g., any of the detectable labels described herein), small molecule, or another antibody. For example, the toxin may be *Pseudomonas* exotoxin A ("PE") or variants thereof such as, e.g., any of PE4E, PE40, PE38, PE25, PE38QQR, PE38KDEL, PE-LR, and PE35, as described in, e.g., U.S. Pat. Nos. 4,892,827; 5,512,658; 5,602,095; 5,608,039; 5,821,238; 5,854,044; U.S. Patent Application Publication No. US 2010/0215656; and WO 2012/041234, each of which is incorporated herein by reference.

Further provided by an embodiment of the invention is a nucleic acid comprising a nucleotide sequence encoding any of the polypeptides, proteins, CARs, anti-CD276 binding moieties, conjugates, or functional portions or functional variants thereof. The nucleic acids of the invention may comprise a nucleotide sequence encoding any of the leader sequences, linkers, antigen binding domains, immunoglobulin domains, transmembrane domains, and/or intracellular T cell signaling domains described herein. For example, the nucleic acids may comprise a nucleotide sequence encoding a leader, the nucleotide sequence comprising SEQ ID NO: 63 or 64. Alternatively or additionally, the nucleic acids may comprise a nucleotide sequence encoding an immunoglobulin constant domain, the nucleotide sequence comprising SEQ ID NO: 72. Alternatively or additionally, the nucleic acids may comprise a nucleotide sequence encoding a transmembrane domain comprising CD28 and an intracellular T cell signaling domain comprising CD28 and CD3 zeta, the nucleotide sequence comprising SEQ ID NO: 76. Alternatively or additionally, the nucleic acids may comprise a nucleotide sequence encoding a transmembrane domain comprising CD8 and an intracellular T cell signaling domain comprising CD28, CD137, and CD3 zeta, the nucleotide sequence comprising SEQ ID NO: 78. Alternatively or additionally, the nucleic acids may comprise a nucleotide sequence encoding a transmembrane domain comprising CD8 and an intracellular T cell signaling domain comprising CD137 and CD3 zeta, the nucleotide sequence comprising SEQ ID NO: 77. Alternatively or additionally, the nucleic acids may comprise a nucleotide sequence encoding a leader, an antigen binding domain, and an immunoglobulin domain, the nucleotides sequence comprising SEQ ID NO: 79, 81, or 83.

An embodiment of the invention provides a nucleic acid comprising a nucleotide sequence encoding any of the polypeptides, proteins, or antigen binding domains described herein. In this regard, the nucleic acid encoding a polypeptide or protein may comprise a nucleotide sequence comprising SEQ ID NO: 57 (CD276.1 antigen binding domain), SEQ ID NO: 58 (CD276.6 antigen binding domain), or SEQ ID NO: 59 (CD276.17 antigen binding domain). In another embodiment of the invention, the nucleic acid encoding the variable regions of a polypeptide or protein may comprise a nucleotide sequence comprising (i) SEQ ID NOs: 116 and 117, (ii) SEQ ID NOs: 118 and 119, or (iii) SEQ ID NOs: 120 and 121. Another embodiment of the invention provides a nucleic acid comprising a nucleotide sequence encoding any of the CARs described herein. In this regard, the nucleic acid may comprise one or more of any of the nucleotide sequences set forth in Tables 2A and 2B. Any of the nucleic acids described herein may further comprise, on the 5' end, a nucleotide sequence encoding a leader sequence comprising, for example, SEQ ID NO: 140.

TABLE 2A

| SEQ ID NO: | Antigen Binding Domain | Further Components |
|---|---|---|
| SEQ ID NO: 48 (CD276.6 CAR- second generation, version 1) | CD276.6 scFv (SEQ ID NO: 58) | CH2CH3 CD28 transmembrane domain CD28 and CD3ζ intracellular T cell signaling domains |
| SEQ ID NO: 49 (CD276.6 CAR- second generation, version 2) | CD276.6 scFv (SEQ ID NO: 58) | CH2CH3 CD8 transmembrane domain CD137 and CD3ζ intracellular T cell signaling domains |
| SEQ ID NO: 50 (CD276.6 CAR- third generation) | CD276.6 scFv (SEQ ID NO: 58) | CH2CH3 CD8 transmembrane domain CD28, CD137, and CD3ζ intracellular T cell signaling domains |
| SEQ ID NO: 51 (CD276.1 CAR- second generation, version 1) | CD276.1 scFv (SEQ ID NO: 57) | CH2CH3 CD28 transmembrane domain CD28 and CD3ζ intracellular T cell signaling domains |
| SEQ ID NO: 52 (CD276.1 CAR- second generation, version 2) | CD276.1 scFv (SEQ ID NO: 57) | CH2CH3 CD8 transmembrane domain CD137 and CD3ζ intracellular T cell signaling domains |
| SEQ ID NO: 53 (CD276.1 CAR- third generation) | CD276.1 scFv (SEQ ID NO: 57) | CH2CH3 CD8 transmembrane domain CD28, CD137, and CD3ζ intracellular T cell signaling domains |
| SEQ ID NO: 54 (CD276.17 CAR- second generation, version 1) | CD276.17 scFv (SEQ ID NO: 59) | CH2CH3 CD28 transmembrane domain CD28 and CD3ζ intracellular T cell signaling domains |
| SEQ ID NO: 55 (CD276.17 CAR- second generation, version 2) | CD276.17 scFv (SEQ ID NO: 59) | CH2CH3 CD8 transmembrane domain CD137 and CD3ζ intracellular T cell signaling domains |
| SEQ ID NO: 56 (CD276.17 CAR- third generation) | CD276.17 scFv (SEQ ID NO: 59) | CH2CH3 CD8 transmembrane domain CD28, CD137, and CD3ζ intracellular T cell signaling domains |

TABLE 2B

| SEQ ID NO: | Antigen Binding Domain | Further Components |
|---|---|---|
| SEQ ID NO: 131 (CD276.6 CAR- | CD276.6 scFv (SEQ ID NO: 58) | CD28 transmembrane domain CD28 and CD3ζ intracellular |

TABLE 2B-continued

| SEQ ID NO: | Antigen Binding Domain | Further Components |
|---|---|---|
| second generation, version 1) | | T cell signaling domains |
| SEQ ID NO: 132 (CD276.6 CAR- second generation, version 2) | CD276.6 scFv (SEQ ID NO: 58) | CD8 transmembrane domain CD137 and CD3ζ intracellular T cell signaling domains |
| SEQ ID NO: 133 (CD276.6 CAR- third generation) | CD276.6 scFv (SEQ ID NO: 58) | CD8 transmembrane domain CD28, CD137, and CD3ζ intracellular T cell signaling domains |
| SEQ ID NO: 134 (CD276.1 CAR- second generation, version 1) | CD276.1 scFv (SEQ ID NO: 57) | CD8 transmembrane domain CD28 and CD3ζ intracellular T cell signaling domains |
| SEQ ID NO: 135 (CD276.1 CAR- second generation, version 2) | CD276.1 scFv (SEQ ID NO: 57) | CD8 transmembrane domain CD137 and CD3ζ intracellular T cell signaling domains |
| SEQ ID NO: 136 (CD276.1 CAR- third generation) | CD276.1 scFv (SEQ ID NO: 57) | CD8 transmembrane domain CD28, CD137, and CD3ζ intracellular T cell signaling domains |
| SEQ ID NO: 137 (CD276.17 CAR- second generation, version 1) | CD276.17 scFv (SEQ ID NO: 59) | CD8 transmembrane domain CD28 and CD3ζ intracellular T cell signaling domains |
| SEQ ID NO: 138 (CD276.17 CAR- second generation, version 2) | CD276.17 scFv (SEQ ID NO: 59) | CD8 transmembrane domain CD137 and CD3ζ intracellular T cell signaling domains |
| SEQ ID NO: 139 (CD276.17 CAR- third generation) | CD276.17 scFv (SEQ ID NO: 59) | CD8 transmembrane domain CD28, CD137, and CD3ζ intracellular T cell signaling domains |

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions. In some embodiments, the nucleic acid may encode additional amino acid sequences that do not affect the function of the polypeptide, protein, or CAR and which may or may not be translated upon expression of the nucleic acid by a host cell (e.g., AAA). In an embodiment of the invention, the nucleic acid is complementary DNA (cDNA).

The nucleic acids of an embodiment of the invention may be recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can consist essentially of the specified nucleotide sequence or sequences described herein, such that other components, e.g., other nucleotides, do not materially change the biological activity of the encoded CAR, polypeptide, protein, functional portion, or functional variant.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Green et al., supra. The nucleic acids can be constructed based on chemical synthesis and/or enzymatic ligation reactions using procedures known in the art. See, for example, Green et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise any isolated or purified nucleotide sequence which encodes any of the polypeptides, proteins, CARs, anti-CD276 binding moieties, conjugates, or functional portions or functional variants thereof. Alternatively, the nucleotide sequence can comprise a nucleotide sequence which is degenerate to any of the sequences or a combination of degenerate sequences.

An embodiment of the invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive polypeptides, proteins, CARs, anti-CD276 binding moieties, conjugates, or functional portions or functional variants thereof. It is generally appreciated that conditions can be rendered more stringent by the addition of increasing amounts of formamide.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acids of the invention can be incorporated into a recombinant expression vector. In this regard, an embodiment of the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM, and pMAMneo (Clontech). The recombinant expression vector may be a viral vector, e.g., a retroviral vector.

A number of transfection techniques are generally known in the art (see, e.g., Graham et al., *Virology,* 52: 456-467 (1973); Green et al., supra; Davis et al., *Basic Methods in Molecular Biology,* Elsevier (1986); and Chu et al., *Gene,* 13: 97 (1981). Transfection methods include calcium phosphate co-precipitation (see, e.g., Graham et al., supra), direct micro injection into cultured cells (see, e.g., Capecchi, *Cell,* 22: 479-488 (1980)), electroporation (see, e.g., Shigekawa et al., *BioTechniques,* 6: 742-751 (1988)), liposome mediated gene transfer (see, e.g., Mannino et al., *BioTechniques,* 6: 682-690 (1988)), lipid mediated transduction (see, e.g., Felgner et al., *Proc. Natl. Acad. Sci. USA,* 84: 7413-7417 (1987)), and nucleic acid delivery using high velocity microprojectiles (see, e.g., Klein et al., *Nature,* 327: 70-73 (1987)).

In an embodiment, the recombinant expression vectors of the invention can be prepared using standard recombinant DNA techniques described in, for example, Green et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may comprise restriction sites to facilitate cloning. Examples of sequences including restriction sites include SEQ ID NOs: 65-70.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the polypeptides, proteins, CARs, anti-CD276 binding moieties, conjugates, or functional portions or functional variants thereof, or to the nucleotide sequence which is complementary to or which hybridizes to the nucleotide sequence encoding the inventive polypeptides, proteins, CARs, anti-CD276 binding moieties, conjugates, or functional portions or functional variants thereof. The selection of promoters, e.g., strong, weak, inducible, tissue-specific and developmental-specific, is within the ordinary skill of the artisan. Similarly, the combining of a nucleotide sequence with a promoter is also within the ordinary skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, *Suicide Gene Therapy: Methods and Reviews*, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

An embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5α cell. For purposes of producing a recombinant polypeptide, protein, CAR, anti-CD276 binding moiety, conjugate, or functional portion or functional variant thereof, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a B cell or a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, $CD4^+/CD8^+$ double positive T cells, $CD4^+$ helper T cells, e.g., $Th_1$ and $Th_2$ cells, $CD8^+$ T cells (e.g., cytotoxic T cells), tumor infiltrating cells, memory T cells, naïve T cells, and the like. The T cell may be a $CD8^+$ T cell or a $CD4^+$ T cell.

Also provided by an embodiment of the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

The polypeptides, proteins, CARs (including functional portions and variants thereof), nucleic acids, recombinant expression vectors, host cells (including populations thereof), anti-CD276 binding moieties, and conjugates, all of which are collectively referred to as "inventive anti-CD276 materials" hereinafter, can be isolated and/or purified. The term "isolated" as used herein means having been removed from its natural environment. The term "purified" or "isolated" does not require absolute purity or isolation; rather, it is intended as a relative term. Thus, for example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example, at least about 70%, of the total cell content of the preparation. For example, the purity can be at least about 50%, can be greater than about 60%, about 70% or about 80%, or can be about 100%.

The inventive anti-CD276 materials can be formulated into a composition, such as a pharmaceutical composition. In this regard, an embodiment of the invention provides a pharmaceutical composition comprising any of the inventive anti-CD276 materials described herein and a pharmaceutically acceptable carrier. The inventive pharmaceutical compositions containing any of the inventive anti-CD276 materials can comprise more than one inventive anti-CD276 material, e.g., a CAR and a nucleic acid, or two or more different CARs. Alternatively, the pharmaceutical composition can comprise an inventive CAR material in combination with other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In a preferred embodiment, the pharmaceutical composition comprises the inventive host cell or populations thereof.

The inventive anti-CD276 materials can be provided in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

With respect to pharmaceutical compositions, the pharmaceutically acceptable carrier can be any of those conventionally used and is limited only by chemico-physical considerations, such as solubility and lack of reactivity with the active agent(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular inventive CAR material, as well as by the particular method used to administer the inventive CAR material. Accordingly, there are a variety of suitable formulations of the pharmaceutical composition of the invention. Preservatives may be used. Suitable preservatives may include, for example, methylparaben, propylparaben, sodium benzoate, and benzalkonium chloride. A mixture of two or more preservatives optionally may be used. The preservative or mixtures thereof are typically present in an amount of about 0.0001% to about 2% by weight of the total composition.

Suitable buffering agents may include, for example, citric acid, sodium citrate, phosphoric acid, potassium phosphate, and various other acids and salts. A mixture of two or more buffering agents optionally may be used. The buffering agent or mixtures thereof are typically present in an amount of about 0.001% to about 4% by weight of the total composition.

The concentration of inventive anti-CD276 material in the pharmaceutical formulations can vary, e.g., from less than about 1%, usually at or at least about 10%, to as much as, for example, about 20% to about 50% or more by weight, and can be selected primarily by fluid volumes, and viscosities, in accordance with the particular mode of administration selected.

Methods for preparing administrable (e.g., parenterally administrable) compositions are known or apparent to those skilled in the art and are described in more detail in, for example, *Remington: The Science and Practice of Pharmacy*, Lippincott Williams & Wilkins; 21st ed. (May 1, 2005).

The following formulations for oral, aerosol, parenteral (e.g., subcutaneous, intravenous, intraarterial, intramuscular, intradermal, interperitoneal, and intrathecal), and topical administration are merely exemplary and are in no way limiting. More than one route can be used to administer the inventive anti-CD276 materials, and in certain instances, a particular route can provide a more immediate and more effective response than another route.

Formulations suitable for oral administration can comprise or consist of (a) liquid solutions, such as an effective amount of the inventive anti-CD276 material dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard or softshelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the inventive anti-CD276 material in a flavor, usually sucrose and acacia or tragacanth, as well as pastilles comprising the inventive anti-CD276 material in an inert base, such as gelatin and glycerin, or sucrose and acacia, emulsions, gels, and the like containing, in addition to, such excipients as are known in the art.

Formulations suitable for parenteral administration include aqueous and nonaqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inventive anti-CD276 material can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain, for example, from about 0.5% to about 25% by weight of the inventive anti-CD276 material in solution. Preservatives and buffers may be used. In order to minimize or eliminate irritation at the site of injection, such compositions may contain one or more nonionic surfactants having, for example, a hydrophile-lipophile balance (HLB) of from about 12 to about 17. The quantity of surfactant in such formulations will typically range, for example, from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Injectable formulations are in accordance with an embodiment of the invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Toissel, 4th ed., pages 622-630 (1986)).

Topical formulations, including those that are useful for transdermal drug release, are well known to those of skill in the art and are suitable in the context of embodiments of the invention for application to skin. The inventive anti-CD276 material, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

An "effective amount" or "an amount effective to treat" refers to a dose that is adequate to prevent or treat cancer in an individual. Amounts effective for a therapeutic or prophylactic use will depend on, for example, the stage and severity of the disease or disorder being treated, the age, weight, and general state of health of the patient, and the judgment of the prescribing physician. The size of the dose will also be determined by the active selected, method of administration, timing and frequency of administration, the existence, nature, and extent of any adverse side-effects that might accompany the administration of a particular active, and the desired physiological effect. It will be appreciated by one of skill in the art that various diseases or disorders could require prolonged treatment involving multiple administrations, perhaps using the inventive anti-CD276 materials in each or various rounds of administration. By way of example and not intending to limit the invention, the dose of the inventive anti-CD276 material can be about 0.001 to about 1000 mg/kg body weight of the subject being treated/day, from about 0.01 to about 10 mg/kg body weight/day, about 0.01 mg to about 1 mg/kg body weight/day. When the inventive anti-CD276 material is a host cell, an exemplary dose of host cells may be a minimum of one million cells (1 mg cells/dose). When the inventive anti-CD276 material is a nucleic acid packaged in a virus, an exemplary dose of virus may be 1 ng/dose.

For purposes of the invention, the amount or dose of the inventive anti-CD276 material administered should be sufficient to effect a therapeutic or prophylactic response in the subject or animal over a reasonable time frame. For example, the dose of the inventive anti-CD276 material should be sufficient to bind to antigen, or detect, treat or prevent disease in a period of from about 2 hours or longer, e.g., about 12 to about 24 or more hours, from the time of administration. In certain embodiments, the time period could be even longer. The dose will be determined by the efficacy of the particular inventive anti-CD276 material and the condition of the animal (e.g., human), as well as the body weight of the animal (e.g., human) to be treated.

For purposes of the invention, an assay, which comprises, for example, comparing the extent to which target cells are lysed and/or IFN-γ is secreted by T cells expressing the inventive anti-CD276 material upon administration of a given dose of such T cells to a mammal, among a set of mammals of which is each given a different dose of the T cells, could be used to determine a starting dose to be administered to a mammal. The extent to which target cells are lysed and/or IFN-γ is secreted upon administration of a certain dose can be assayed by methods known in the art.

In addition to the aforedescribed pharmaceutical compositions, the inventive anti-CD276 materials can be formulated as inclusion complexes, such as cyclodextrin inclusion complexes, or liposomes. Liposomes can serve to target the inventive anti-CD276 materials to a particular tissue. Liposomes also can be used to increase the half-life of the inventive anti-CD276 materials. Many methods are available for preparing liposomes, as described in, for example, Szoka et al., *Ann. Rev. Biophys. Bioeng.*, 9, 467 (1980) and U.S. Pat. Nos. 4,235,871, 4,501,728, 4,837,028, and 5,019,369.

The delivery systems useful in the context of embodiments of the invention may include time-released, delayed release, and sustained release delivery systems such that the delivery of the inventive composition occurs prior to, and with sufficient time to cause, sensitization of the site to be treated. The inventive composition can be used in conjunction with other therapeutic agents or therapies. Such systems can avoid repeated administrations of the inventive composition, thereby increasing convenience to the subject and the physician, and may be particularly suitable for certain composition embodiments of the invention.

Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

One of ordinary skill in the art will readily appreciate that the inventive anti-CD276 materials of the invention can be modified in any number of ways, such that the therapeutic or prophylactic efficacy of the inventive anti-CD276 materials is increased through the modification. For instance, the inventive anti-CD276 materials can be conjugated either directly or indirectly through a bridge to a targeting moiety. The practice of conjugating compounds, e.g., inventive anti-CD276 materials, to targeting moieties is known in the art. See, for instance, Wadwa et al., *J. Drug Targeting* 3: 111 (1995) and U.S. Pat. No. 5,087,616.

Alternatively, the inventive anti-CD276 materials can be modified into a depot form, such that the manner in which the inventive anti-CD276 materials is released into the body to which it is administered is controlled with respect to time and location within the body (see, for example, U.S. Pat. No. 4,450,150). Depot forms of inventive anti-CD276 materials can be, for example, an implantable composition comprising the inventive anti-CD276 materials and a porous or non-porous material, such as a polymer, wherein the inventive anti-CD276 materials are encapsulated by or diffused throughout the material and/or degradation of the non-porous material. The depot is then implanted into the desired location within the body and the inventive anti-CD276 materials are released from the implant at a predetermined rate.

When the inventive anti-CD276 materials are administered with one or more additional therapeutic agents, one or more additional therapeutic agents can be coadministered to the mammal. By "coadministering" is meant administering one or more additional therapeutic agents and the inventive CAR materials sufficiently close in time such that the inventive anti-CD276 materials can enhance the effect of one or more additional therapeutic agents, or vice versa. In this regard, the inventive anti-CD276 materials can be administered first and the one or more additional therapeutic agents can be administered second, or vice versa. Alternatively, the inventive anti-CD276 materials and the one or more additional therapeutic agents can be administered simultaneously. An exemplary therapeutic agent that can be co-administered with the anti-CD276 materials is IL-2. It is believed that IL-2 enhances the therapeutic effect of the inventive anti-CD276 materials. For purposes of the inventive methods, wherein host cells or populations of cells are administered to the mammal, the cells can be cells that are allogeneic or autologous to the mammal.

It is contemplated that the inventive anti-CD276 materials and pharmaceutical compositions can be used in methods of treating or preventing a disease in a mammal. Without being bound to a particular theory or mechanism, the inventive anti-CD276 materials have biological activity, e.g., ability to recognize antigen, e.g., CD276, such that the anti-CD276 material, when expressed by a cell, is able to mediate an immune response against the cell expressing the antigen, e.g., CD276, for which the anti-CD276 material is specific. In this regard, an embodiment of the invention provides a method of treating or preventing cancer in a mammal, comprising administering to the mammal any of the polypeptides, proteins, CARs, functional portions, functional variants, nucleic acids, recombinant expression vectors, host cells, population of cells, anti-CD276 binding moieties, conjugates, and/or the pharmaceutical compositions of the invention in an amount effective to treat or prevent cancer in the mammal.

An embodiment of the invention further comprises lymphodepleting the mammal prior to administering the inventive anti-CD276 materials. Examples of lymphodepletion include, but may not be limited to, nonmyeloablative lymphodepleting chemotherapy, myeloablative lymphodepleting chemotherapy, total body irradiation, etc.

For purposes of the inventive methods, wherein host cells or populations of cells are administered, the cells can be cells that are allogeneic or autologous to the mammal. Preferably, the cells are autologous to the mammal.

The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the inventive methods, the cancer can be any cancer, including any of acute lymphocytic cancer, acute myeloid leukemia, rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, Ewing's sarcoma, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma), lymphoma, malignant mesothelioma, mastocytoma, melanoma, multiple myeloma, nasopharynx cancer, neuroblastoma, non-Hodgkin lymphoma, B-chronic lymphocytic leukemia, hairy cell leukemia, acute lymphocytic leukemia (ALL), and Burkitt's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, stomach cancer, testicular cancer, thyroid cancer, and ureter cancer. Preferably, the cancer is a pediatric solid tumor, adult carcinoma, neuroblastoma, Ewing's sarcoma, rhabdomyosarcoma, and prostate, ovarian, colorectal, or lung cancer. Preferably, the cancer is characterized by the expression or overexpression of CD276.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

Another embodiment of the invention provides a use of any of the polypeptides, proteins, CARs, functional portions, functional variants, nucleic acids, recombinant expression vectors, host cells, population of cells, anti-CD276 binding moieties, conjugates, or pharmaceutical compositions of the invention for the treatment or prevention of cancer in a mammal.

Another embodiment of the invention provides a method of detecting the presence of cancer in a mammal, comprising: (a) contacting a sample comprising one or more cells from the mammal with any of the polypeptides, proteins, CARs, functional portions, functional variants, nucleic acids, recombinant expression vectors, host cells, population of cells, anti-CD276 binding moieties, or conjugates of the invention, thereby forming a complex, (b) and detecting the complex, wherein detection of the complex is indicative of the presence of cancer in the mammal.

The sample may be obtained by any suitable method, e.g., biopsy or necropsy. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer.

With respect to an embodiment of the inventive method of detecting the presence of cancer in a mammal, the sample comprising cells of the mammal can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the mammal, e.g., the cells of any organ or tissue, including blood cells or endothelial cells.

For purposes of the inventive detecting method, the contacting can take place in vitro or in vivo with respect to the mammal. Preferably, the contacting is in vitro.

Also, detection of the complex can occur through any number of ways known in the art. For instance, the inventive CARs, polypeptides, proteins, functional portions, functional variants, nucleic acids, recombinant expression vectors, host cells, populations of cells, anti-CD276 binding moieties, or conjugates, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

Methods of testing an anti-CD276 material for the ability to recognize target cells and for antigen specificity are known in the art. For instance, Clay et al., *J. Immunol.*, 163: 507-513 (1999), teaches methods of measuring the release of cytokines (e.g., interferon-γ, granulocyte/monocyte colony stimulating factor (GM-CSF), tumor necrosis factor a (TNF-α) or interleukin 2 (IL-2)). In addition, anti-CD276 material function can be evaluated by measurement of cellular cytotoxicity, as described in Zhao et al., *J. Immunol.*, 174: 4415-4423 (2005).

The following examples further illustrate the invention but, of course, should not be construed as in any way limiting its scope.

EXAMPLE 1

This example demonstrates the identification, purification, and characterization of anti-CD276 binding domains.
Yeast Display Naïve Human Antibody Library, Antibodies, Biotinylation Kit, Cells A large yeast display naïve single chain variable fragment (scFv) human antibody library was constructed using a collection of human antibody gene repertoires, including the genes used for the construction of a phage display Fab library (Zhu et al., *Methods Mol. Biol.*, 525: 129-142, xv (2009)).

Mouse monoclonal anti-c-Myc antibody was purchased from Roche (Pleasanton, Calif.). PE-conjugated streptavidin and Alexa-488 conjugated goat anti-mouse antibody were purchased from Invitrogen (Carlsbad, Calif.). Protein G columns were purchased from GE healthcare (Waukesha, Wis.). Avi-tag specific biotinylation kits were purchased from Avidity (Aurora, Colo.). Yeast plasmid extraction kits were purchased from Zymo Research (Irvine, Calif.). 293 free style protein expression kits were purchased from Invitrogen. An AutoMACS System was purchased from Miltenyi Biotec (Cologne, Germany).
MACS Sorting Downsize of the Initial Yeast Display Human Antibody Library Biotinylated human and mouse CD276 extracellular domain was used as the target for three rounds of sorting to downsize the initial yeast display naïve human antibody library. Approximately 1010 cells from the initial naïve antibody library and 10 µg of biotinylated CD276 ectodomain were incubated in 50 ml PBSA (phosphate-buffered saline containing 0.1% bovine serum albumin) at room temperature (RT) for 2 hr with rotation. The mixture of biotinylated CD276 ecto-domain bound to displayed antibody on cells from the library was washed three times with PBSA and incubated with 100 µl of streptavidin conjugated microbeads at RT from Miltenyi Biotec. The resultant mixture was washed once with PBSA and loaded onto the AutoMACS system for the first round of sorting. The sorted cells were amplified in SDCAA media (20 g dextrose, 6.7 g DIFCO yeast nitrogen base without (w/o) amino acids, 5 g BACTO casamino acids, 5.4 g $Na_2HPO_4$ and 8.56 g $NaH_2PO_4.H_2O$ in 1 liter water) at 30° C. and 250 revolutions per minute (rpm) for 24 hours (hr). The culture was then induced in SGCAA media (20 g galactose, 20 g raffinose, 1 g dextrose, 6.7 g DIFCO yeast nitrogen base w/o amino acids, 5 g BACTO casamino acids, 5.4 g $Na_2HPO_4$ and 8.56 g $NaH_2PO_4.H_2O$ in 1 liter water) at 20° C. and 250 rpm for 16-18 hr.

The same amounts of antigen and incubation volume were used for the next two rounds of sorting. The cell numbers used for these two rounds of sorting were set at 100 times the size of the sorted pool from the previous round of sorting to keep the diversity of each sorted pool.
Expression and Purification of scFv-Fc Proteins Plasmids were extracted from the identified yeast clones using yeast plasmid extraction kits (Zymo Research, Irvine, Calif.), following the manufacturer's instructions. Extracted plasmids were transformed into 10G chemical competent *E. coli* (Lucigen, Middleton, Wis.) for further amplification. Plasmids extracted from the bacteria were used for DNA sequencing to obtain the nucleic acid sequences encoding the positive binder antibodies.

Three anti-CD276 antibodies were identified, each comprising heavy and light chain amino acid sequences as follows: (1) Clone CD276.1 (m851) (comprising a heavy chain comprising SEQ ID NO: 17 and a light chain comprising SEQ ID NO: 18), (2) Clone CD276.6 (m856) (comprising a heavy chain comprising SEQ ID NO: 7 and a light chain comprising SEQ ID NO: 8), and (3) Clone CD276.17 (m8517) (comprising a heavy chain comprising SEQ ID NO: 26 and a light chain comprising SEQ ID NO: 27).

Figure 6:
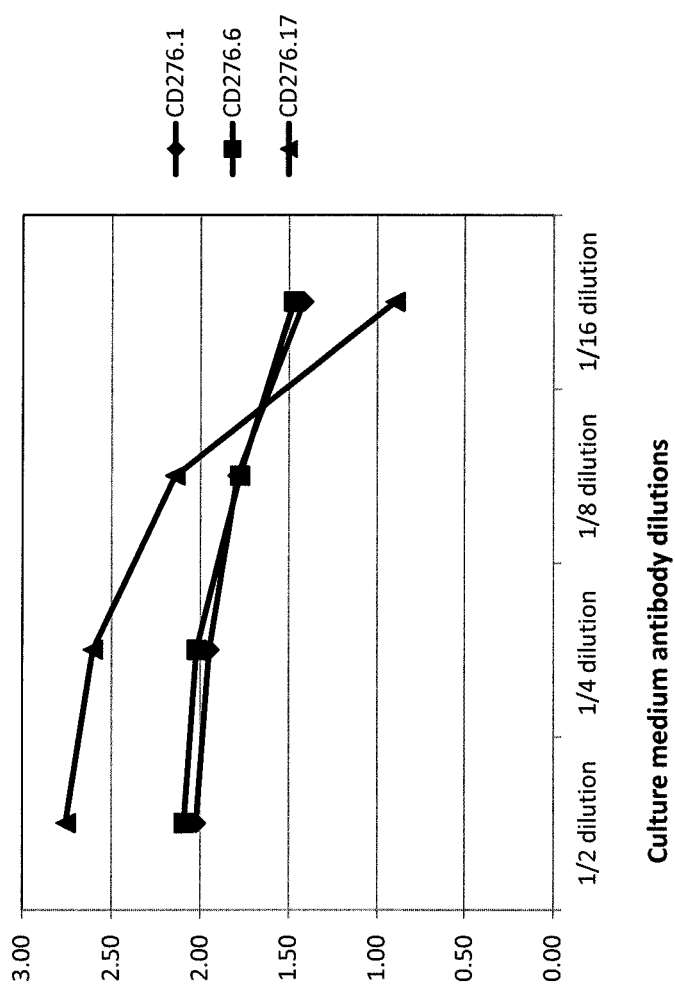
FIGS. 6 and 7 are graphs showing the optical density (OD) reading at 450 nm as measured in an ELISA binding assay for scFv-Fc fusion proteins comprising heavy and light chain amino acid sequences as follows: (1) Clone CD276.1 (m851) (comprising a heavy chain comprising SEQ ID NO: 17 and a light chain comprising SEQ ID NO: 18) (diamonds), (2) Clone CD276.6 (m856) (comprising a heavy chain comprising SEQ ID NO: 7 and a light chain comprising SEQ ID NO: 8) (squares), or (3) Clone CD276.17 (m8517) (comprising a heavy chain comprising SEQ ID NO: 26 and a light chain comprising SEQ ID NO: 27) (triangles), incubated with human (FIG. 6) or mouse (FIG. 7) CD276 at the dilutions indicated.
Figure 7:
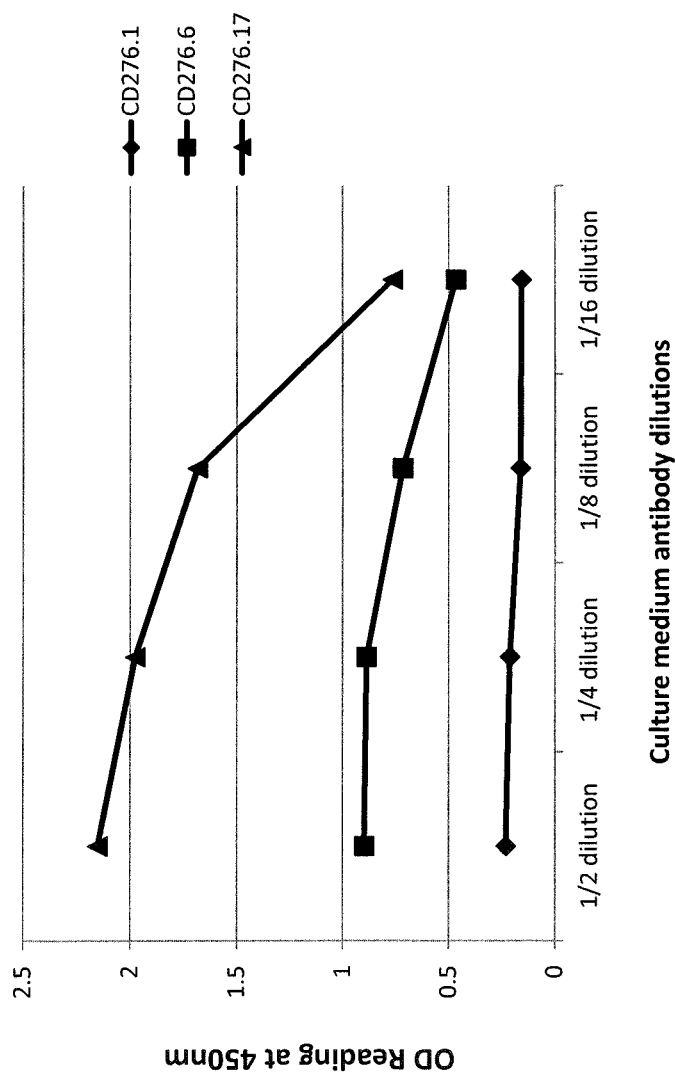
Figure 8:
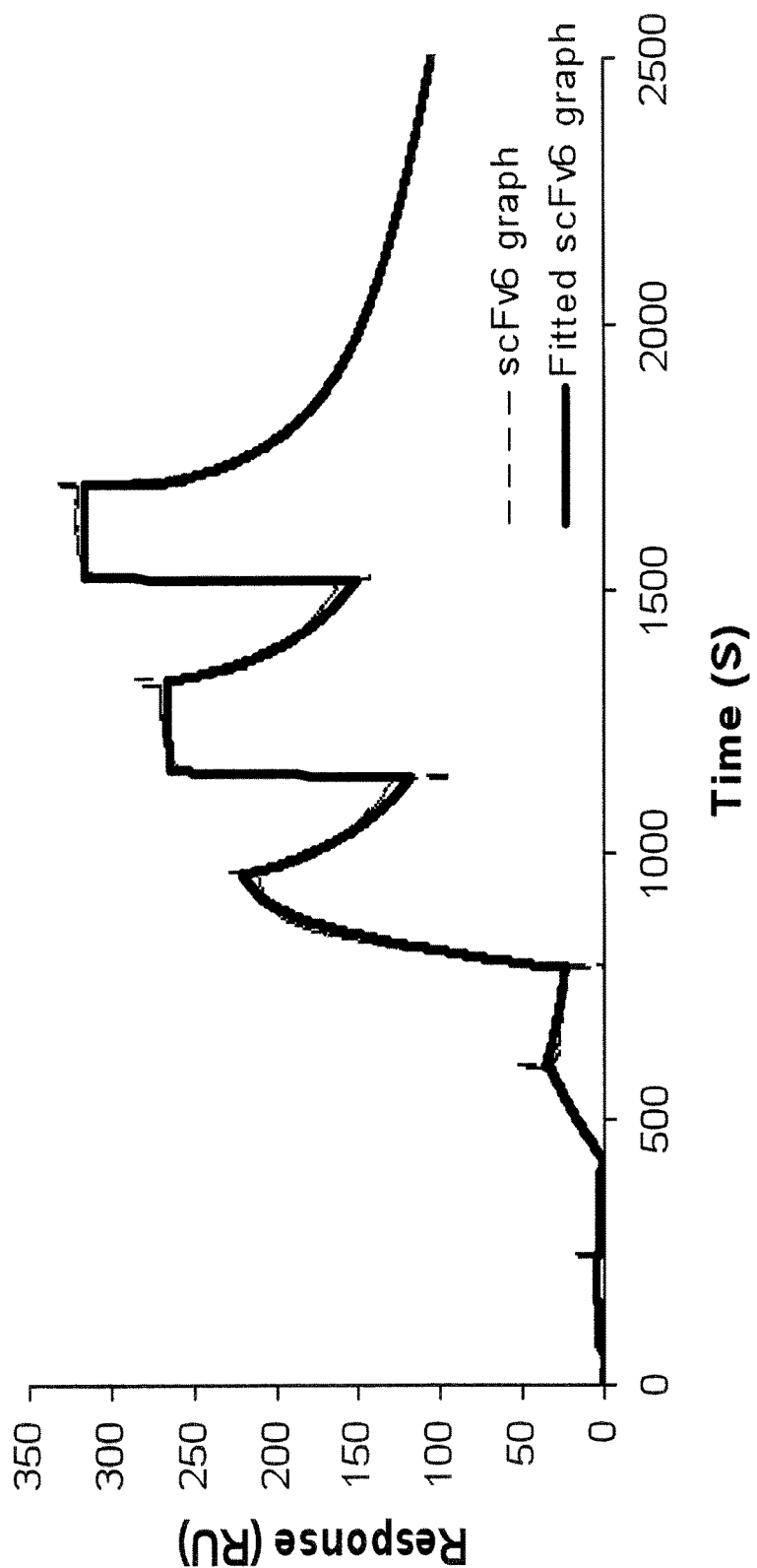
FIG. 8 is a graph showing the binding affinity (response, (RU)) of Clone CD276.6 (m856) (comprising a heavy chain comprising SEQ ID NO: 7 and a light chain comprising SEQ ID NO: 8) to human CD276 over time (s) as measured by surface plasmon resonance at KD=$1.3 \times 10^{-9}$ M. The dotted line corresponds to the raw data and the solid line corresponds to the line generated by the software when the fitting was performed to calculate the KD.

The scFv-encoding inserts of the unique clones were digested with SfiI and ligated into modified pSecTag bearing the same set of SfiI sites and Fc-Avi tag for soluble expression. These constructs were transfected into 293T cells for expression following the manufacturer's protocol. After 72 hr of growth, the scFv-Fc fusion proteins in the culture medium were used for the ELISA binding assay.
ELISA Binding Assay 50 µl of the diluted mouse or human CD276-AP fusion protein in PBS at 2 µg/ml was coated in a 96-well plate at 4° C. overnight. Transiently expressed scFv-Fc fusion protein in the culture medium was serially diluted and added into the target protein coated wells. After washing, a 1:3000 diluted horseradish peroxidase (HRP) conjugated goat anti-human IgG antibody was added for 1 hr at RT. After washing, 3, 3, 5, 5'-Tetramethylbenzidine (TMB) substrate was added, and the optical density (O.D.) was read at 450 nm. The results are shown in FIGS. 6 and 7. As shown in FIG. 6, scFv-Fc fusion proteins comprising heavy and light chain amino acid sequences as follows: (1) Clone CD276.1 (m851) (comprising a heavy chain comprising SEQ ID NO: 17 and a light chain comprising SEQ ID NO: 18), (2) Clone CD276.6 (m856) (comprising a heavy chain comprising SEQ ID NO: 7 and a light chain comprising SEQ ID NO: 8), and (3) Clone CD276.17 (m8517) (comprising a heavy chain comprising SEQ ID NO: 26 and a light chain comprising SEQ ID NO: 27) bound to human CD276. As shown in FIG. 7, all the clones except for m851 (CD276.1) showed cross reactivity to both human and mouse CD276, while m851 (CD276.1) is human CD276-specific.
Affinity Determination by Surface Plasmon Resonance Binding affinities of human anti-CD276 scFv CD276.6 to human CD276 Ecto-domain were analyzed by surface plasmon resonance technology using a Biacore X100 instrument (GE healthcare). The human CD276 soluble extracellular domain was covalently immobilized onto a sensor chip (CM5) using carbodiimide coupling chemistry. A control reference surface was prepared for nonspecific binding and refractive index changes. For analysis of the kinetics of interactions, varying concentrations of antigens were injected at a flow rate of 30 µl/min using running buffer containing 10 mM HEPES, 150 mM NaCl, 3 mM EDTA, and 0.05% Surfactant P-20 (pH 7.4). The association and dissociation phase data were fitted simultaneously to a 1:1 Langumir global model, using the nonlinear data analysis program BIAevaluation 3.2. All of the experiments were done at 25° C. The affinity of the antibody CD276.6 (m856) (comprising a heavy chain comprising SEQ ID NO: 7 and a light chain comprising SEQ ID NO: 8) is shown in FIG. 8.

EXAMPLE 2

This example demonstrates the activity of chimeric antigen receptors (CARs) comprising anti-CD276 binding domains identified in Example 1.

Chimeric antigen receptors (CARs) (second generation-version 1) were produced including single chain variable fragments comprising the anti-CD276 binding domains identified in Example 1. In addition to the anti-CD276 binding domains, the CARs also included an immunoglobulin domain comprising an immunoglobulin CH2 and CH3 immunoglobulin G (IgG1) domain sequence (CH2CH3), a CD28 transmembrane domain, a CD28 intracellular T cell signaling domain, and a CD3ζ intracellular T cell signaling domain. The full length sequences of these CARs comprised SEQ ID NO: 39 (CD276.6 second generation, version 1), SEQ ID NO: 42 (CD276.1 second generation, version 1), or SEQ ID NO: 45 (CD276.17 second generation, version 1).

These CARs were tested against tumor cell lines expressing CD276 as well as a laboratory cell line, CHO, that was transfected to permanently express either CD276 or a control vector, serving as a positive control (CHO-276) and a negative control (CHO), respectively, in assays of immunological function of CAR-transduced T cells. To test CAR activity, human T cells were activated with anti-CD3/CD28 beads in the presence of interleukin (IL)-2. These T cells were then transduced with retroviral CAR expression vectors and tested for activity against tumor cell lines in a chromium release assay. The transduced T cells (effectors) were cultured with chromium-labeled target cells CHO or CHO-276 at the effector to target ratios (number of effector T cells per target cell in the assay well) shown in FIG. 1. The percentage of target cells that were lysed was measured. The results are shown in FIG. 1. The activities of cells expressing SEQ ID NO: 42 (CD276.1 second generation, version 1) or SEQ ID NO: 45 (CD276.17 second generation, version 1) are shown in FIG. 1.

As shown in FIG. 1, while both the CAR comprising SEQ ID NO: 42 (CD276.1 second generation, version 1) and the CAR comprising SEQ ID NO: 45 (CD276.17 second generation, version 1) were active against CHO-276 (the CD276-expressing, positive control cell line), the CAR comprising SEQ ID NO: 45 (CD276.17 second generation, version 1) showed very low activity against the control cell line, indicating a high degree of specific lytic activity.

Figure 2:
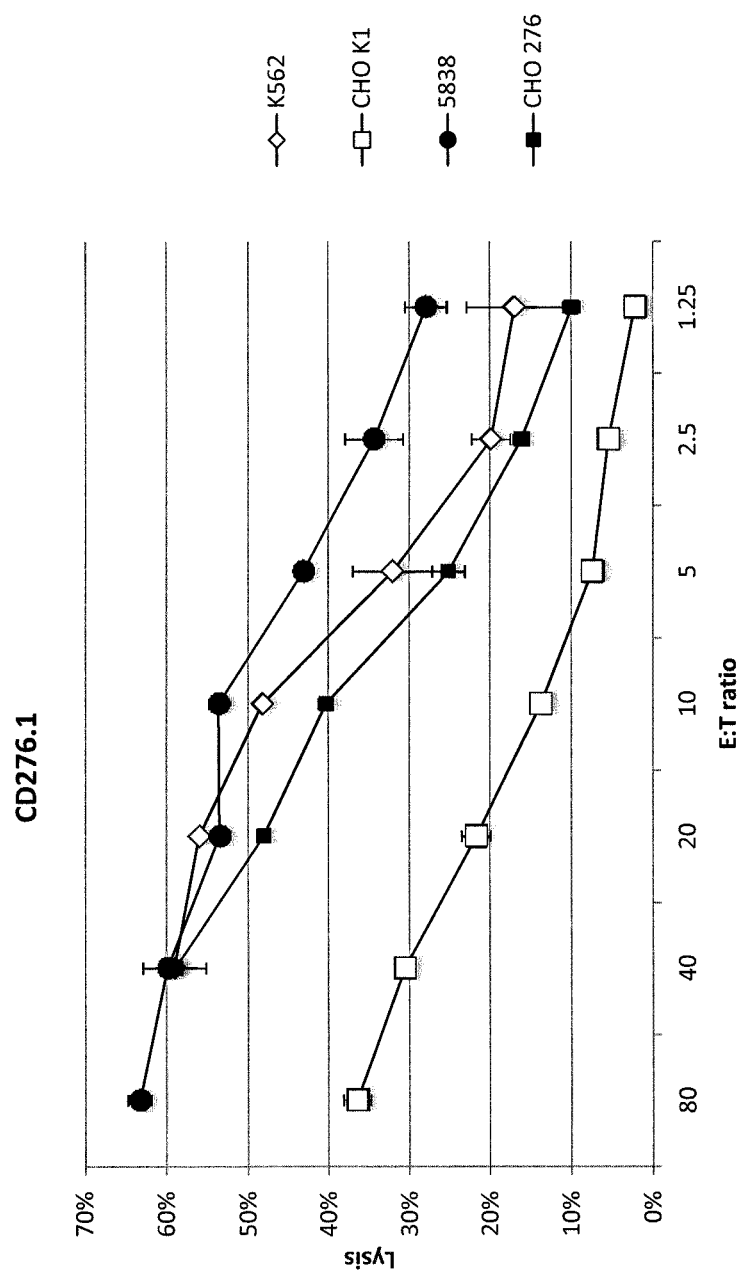
FIG. 2 is a graph showing percent lysis of target cells CHO K1 (open squares), 5838 (closed circles), CHO 276 (closed squares), or K562 (diamonds) by effector human cells transduced with a nucleotide sequence encoding a CAR comprising SEQ ID NO: 42 (CD276.1 second generation, version 1) at the indicated effector to target ratios.
Figure 3:
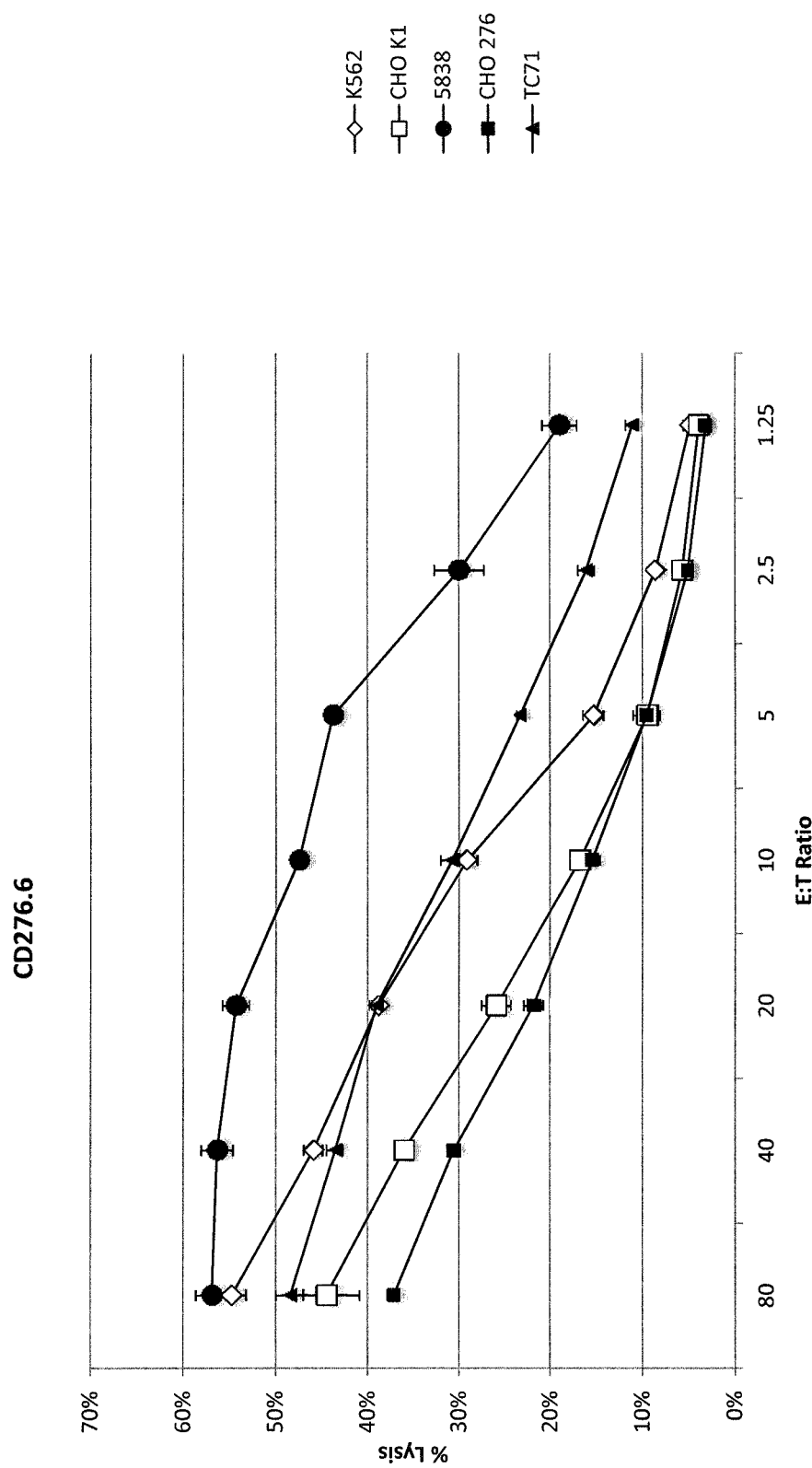
FIG. 3 is a graph showing percent lysis of target cells CHO K1 (open squares), 5838 (closed circles), CHO 276 (closed squares), K562 (diamonds), or TC71 (triangles) by effector human cells transduced with a nucleotide sequence encoding a CAR comprising SEQ ID NO: 39 (CD276.6 second generation, version 1) at the indicated effector to target ratios.
Figure 4:
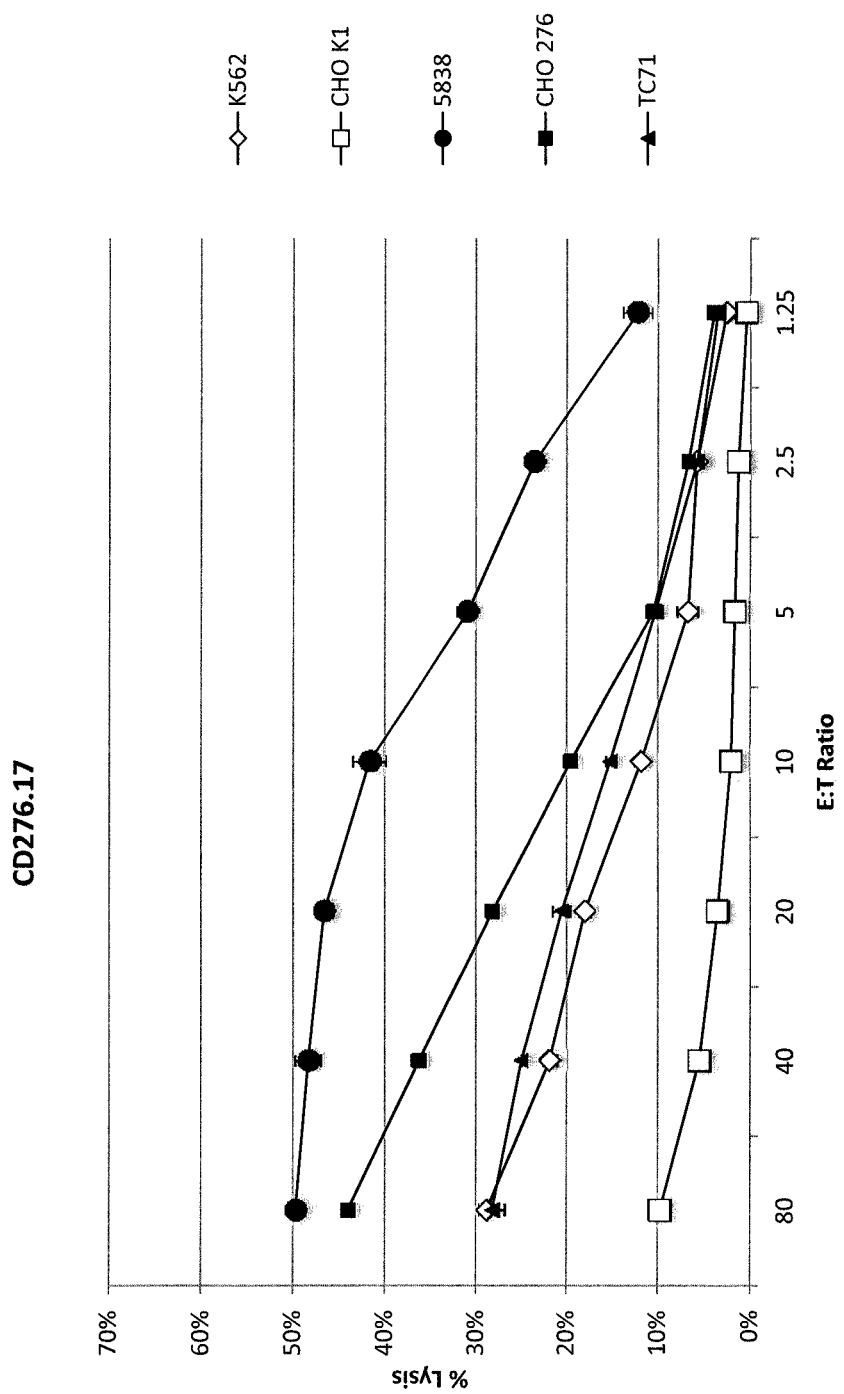
FIG. 4 is a graph showing percent lysis of target cells CHO K1 (open squares), 5838 (closed circles), CHO 276 (closed squares), K562 (diamonds), or TC71 (triangles) by effector human cells transduced with a nucleotide sequence encoding a CAR comprising SEQ ID NO: 45 (CD276.17 second generation, version 1) at the indicated effector to target ratios.

Human cells transduced with nucleotide sequences encoding SEQ ID NO: 39 (CD276.6 second generation, version 1), SEQ ID NO: 42 (CD276.1 second generation, version 1), or SEQ ID NO: 45 (CD276.17 second generation, version 1) CARs (effectors) were co-cultured with chromium-labeled target CHO K1 cells (negative control), positive control CHO-276 cells, or one of the CD276$^+$ tumor cell lines K562 (leukemia cell line), 5838 (patient-derived sarcoma cell line), and TC71 (patient-derived sarcoma cell line) at the effector to target ratios shown in FIGS. 2-4. The percentage of target cells that were lysed was measured. The results are shown in FIGS. 2-4.

As shown in FIGS. 2-4, all CARs were active against CHO-276 (the positive control) and the 5838 Ewing sarcoma cell line. However, CARs differed in their reactivity to the control cell line, with SEQ ID NO: 42 (CD276.1 second generation, version 1) and SEQ ID NO: 39 (CD276.6 second generation, version 1) showing moderate reactivity to CHO-K1, and SEQ ID NO: 45 (CD276.17 second generation, version 1) showing very low activity. Thus, the CD276.17 second generation, version 1 CAR has the highest degree of specific lytic activity.

Figure 5:
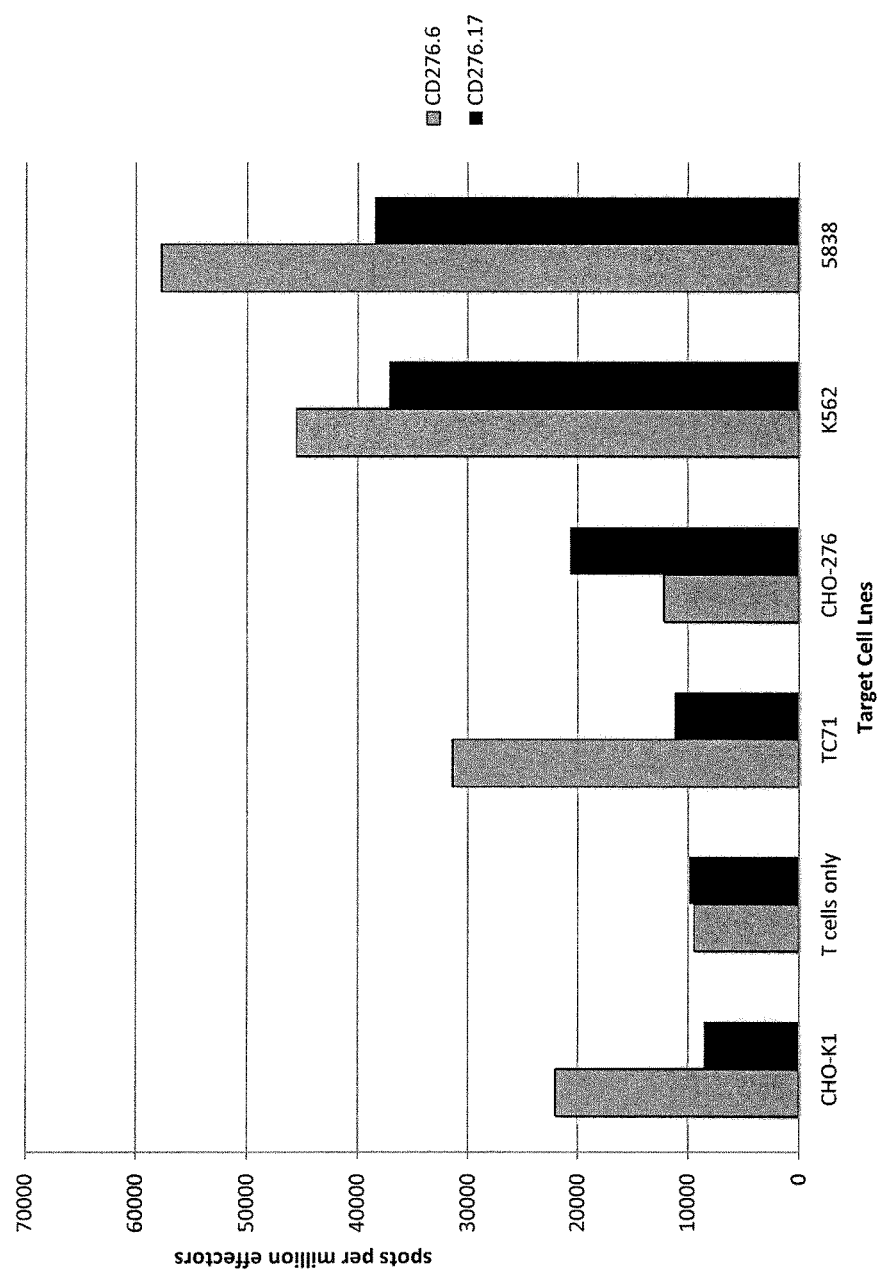
FIG. 5 is a graph showing the number of spots measured by interferon (IFN)-gamma ELISPOT assay per million effector T cells cultured alone (T cells only) or co-cultured with CHO-K1, TC71, CHO-276, K562, or 5838 cells. The effector T cells were transduced with a nucleotide sequence encoding a CAR comprising SEQ ID NO: 39 (CD276.6 second generation, version 1) (grey bars) or SEQ ID NO: 45 (CD276.17 second generation, version 1) (black bars).

The production of interferon (IFN)-gamma was tested in an enzyme-linked immunosorbent spot (ELISPOT) assay. In the ELISPOT assay, CAR-transduced T cells were co-incubated with tumor cells for 24 hours and the number of IFN-gamma producing cells was enumerated by the capture of IFN-gamma on the micro-well filter upon which the assay was performed. Thus, the ELISPOT assay both verifies the production of IFN-gamma by CAR-expressing T cells and quantifies the number of T cells in the culture that are able to express IFN-gamma. The results obtained for cells transduced with nucleotide sequences encoding SEQ ID NO: 45 (CD276.17 second generation, version 1) or SEQ ID NO: 39 (CD276.6 second generation, version 1) are shown in FIG. 5. As shown in FIG. 5, the CD276.17 second generation, version 1 CAR showed a high degree of specific activity in that the greatest number of spots was seen when CAR-transduced T cells were incubated with the CD276-positive cells lines K562 and 5838 and the positive control cell line, CHO-CD276. Low numbers of spots were seen with the negative control cell line or when T cells were incubated alone. Lower levels of activity were seen against the TC71 tumor cell line. As in the tumor lysis assay, the CD276.6 second generation, version 1 CAR T cells had high levels of lysis against CD276-expressing targets, but also a higher level of activity against the negative control cell line.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A polypeptide comprising
a heavy and light chain comprising (i) SEQ ID NOs: 1-6;
a heavy and light chain comprising (ii) SEQ ID NOs: 11-16; or
a heavy and light chain comprising (iii) SEQ ID NOs: 20-25;
wherein the heavy and light chains of (i), (ii), or (iii) bind to CD276, and are linked to one or more of the immunoglobulin constant domains CH2 and/or CH3.

2. The polypeptide according to claim 1, wherein the one or more immunoglobulin constant domains comprise SEQ ID NO: 71.

3. The polypeptide according to claim 1, wherein the heavy and light chains of (i), (ii), or (iii) and the one or more immunoglobulin constant domains comprise SEQ ID NO: 80, SEQ ID NO: 82, or SEQ ID NO: 84.

4. A protein comprising:
a first polypeptide chain comprising
   (i) a heavy chain comprising SEQ ID NOs: 1-3,
   (ii) a heavy chain comprising SEQ ID NOs: 11-13, or
   (iii) a heavy chain comprising SEQ ID NOs: 20-22; and
a second polypeptide chain comprising
   (iv) a light chain comprising SEQ ID NOs: 4-6,
   (v) a light chain comprising SEQ ID NOs: 14-16, or
   (vi) a light chain comprising SEQ ID NOs: 23-25,
wherein the first polypeptide of (i), (ii), or (iii) and the second polypeptide of (iv), (v), or (vi) bind to CD276 and are linked to one or more of the immunoglobulin constant domains CH2 and/or CH3.

5. The protein according to claim 4, wherein the one or more immunoglobulin constant domains comprise SEQ ID NO: 71.

6. The protein according to claim 4, wherein the first polypeptide chain, second polypeptide chain, and one or more immunoglobulin constant domains comprise SEQ ID NO: 80, SEQ ID NO: 82, or SEQ ID NO: 84.

7. The polypeptide according to claim 1, further comprising a linker amino acid sequence.

8. The polypeptide according to claim 7, wherein the linker comprises SEQ ID NO: 115.

9. The polypeptide according to claim 1, comprising SEQ ID NO 10, SEQ ID NO: 19, or SEQ ID NO: 28.

10. A chimeric antigen receptor (CAR) comprising
(a) an antigen binding domain formed by a heavy and light chain comprising (i) SEQ ID NOs: 1-6, a heavy and light chain comprising (ii) SEQ ID NOs: 11-16, or a heavy and light chain comprising (iii) SEQ ID NOs: 20-25, wherein the heavy and light chains of (i), (ii), or (iii) bind to CD276;
(b) an immunoglobulin constant domain;
(c) a transmembrane domain, and
(d) an intracellular T cell signaling domain.

11. The CAR according to claim 10, wherein the immunoglobulin constant domain comprises one or more of CH2 and/or CH3 and is effective to extend the antigen binding domain away from a membrane of a CAR expressing cell.

12. The CAR according to claim 10, wherein the immunoglobulin constant domain comprises SEQ ID NO: 71.

13. The CAR according to claim 10, wherein the transmembrane domain comprises CD8 and CD28.

14. The CAR according to claim 10, wherein the transmembrane domain comprises any one or more of a CD8 amino acid sequence comprising SEQ ID NO: 29, a CD28 amino acid sequence comprising SEQ ID NO: 30, and a CD8 amino acid sequence comprising SEQ ID NO: 31.

15. The CAR according to claim 10, wherein the intracellular T cell signaling domain comprises one or more of i) CD28, ii) CD137, and iii) CD3 zeta.

16. The CAR according to claim 10, wherein the intracellular T cell signaling domain comprises a CD28 amino acid sequence comprising SEQ ID NO: 32 and/or SEQ ID NO: 35.

17. The CAR according to claim 10, wherein the intracellular T cell signaling domain comprises a CD137 amino acid sequence comprising SEQ ID NO: 33 and/or SEQ ID NO: 37.

18. A nucleic acid comprising a nucleotide sequence encoding the polypeptide of claim 1.

19. A recombinant expression vector comprising the nucleic acid of claim 18.

20. An isolated host cell comprising the recombinant expression vector of claim 19.

21. A population of cells comprising at least one isolated host cell of claim 20.

22. The polypeptide of claim 1 expressed in one or more host cells for use in treating cancer in a mammal.

* * * * *